United States Patent [19]
Frank et al.

[11] Patent Number: 5,927,230
[45] Date of Patent: Jul. 27, 1999

[54] ECTOPARASITE SALIVA PROTEINS AND APPARATUS TO COLLECT SUCH PROTEINS

[75] Inventors: Glenn R. Frank, Wellington; Shirley Wu Hunter; Lynda Wallenfels, both of Ft. Collins, all of Colo.

[73] Assignee: Heska Corporation, Ft. Collins, Colo.

[21] Appl. No.: 08/711,905

[22] Filed: Sep. 12, 1996

Related U.S. Application Data

[62] Division of application No. 08/319,590, Oct. 7, 1994, Pat. No. 5,646,115.

[51] Int. Cl.$^6$ ..................................................... A01K 67/00
[52] U.S. Cl. ............................................................ 119/6.5
[58] Field of Search ................................ 119/6.5, 6.6, 6.7

[56] References Cited

U.S. PATENT DOCUMENTS 5,356,622  10/1994  Heath .................................. 424/265.1

FOREIGN PATENT DOCUMENTS

WO 93/18788  9/1993  WIPO .
WO 96/11271  4/1996  WIPO .
WO 96/14089  5/1996  WIPO .

OTHER PUBLICATIONS

Benjamini et al., "Allergy to Flea Bites. IV. In Vitro Collection and Antigenic Properties of the Oral Secretion of the Cat Flea, *Ctenocephalides felis felis* (Bouché)", pp. 143–154, 1963, *Exp. Parasitol.*, vol. 13.

Benjamini et al., "Allergy to Flea Bites. III. The Experimental Induction of Flea Bite Sensitivity in Guinea Pigs by Exposure to Flea Bites and by Antigen Prepared from Whole Flea Extracts of *Ctenocephalides felis felis*", pp. 214–222, 1960, *Exp. Parasitol.*, vol. 10.

Greene et al., "Characterization of Allergens of the Cat Flea, *Ctenocephalides felis*: Detection and Frequency of IgE Antibodies in Canine Sera", pp. 69–74, 1993, *Parasite Immunol.*, vol. 15.

Halliwell et al., "The Role of Basophils in the Immunopathogenesis of Hypersensitivity to Fleas (*Ctenocephalides felis*) in Dogs", pp. 203–213, 1987, Vet. *Immunol. Immunopathol.*, vol. 15.

Keep et al., "Whole Flea Extract as a Desensitising Agent in Canine Summer Dermatitis", pp. 425–426, 1967, *Austral. Vet. J.*, vol. 43.

Kristensen et al., "A Study of Skin Diseases in Dogs and Cats. V. The Intradermal Test in the Diagnosis of Flea Allergy in Dogs and Cats", pp. 414–423, 1978, *Nord. Vet.–Med.*, vol. 30.

Michaeli et al., "In Vitro Studies on the Role of Collagen in the Induction of Hypersensitivity to Flea Bites", pp. 402–406, 1966, *J. Immunol.*, vol. 97, No. 3.

Michaeli et al., "The Role of Collagen in the Induction of Flea Bite Hypersensitivity", pp. 162–170, 1965, *J. Immunol.*, vol. 95, No. 1.

(List continued on next page.)

*Primary Examiner*—Thomas Price
*Attorney, Agent, or Firm*—Sheridan Ross, P.C.

[57] ABSTRACT

The present invention is directed to a novel product and method for isolating ectoparasite saliva proteins, and a novel product and method for detecting and/or treating allergic dermatitis in an animal. The present invention includes a saliva protein collection apparatus capable of collecting ectoparasite saliva proteins substantially free of contaminating material. The present invention also relates to ectoparasite saliva proteins, nucleic acid molecules having sequences that encode such proteins, and antibodies raised against such proteins. The present invention also includes methods to obtain such proteins and to use such proteins to identify animals susceptible to or having allergic dermatitis. The present invention also includes therapeutic compositions comprising such proteins and their use to treat animals susceptible to or having allergic dermatitis.

11 Claims, 12 Drawing Sheets

OTHER PUBLICATIONS

Van Winkle, "An Evaluation of Flea Antigens Used in Intradermal Skin Testing for Flea Allergy in the Canine", pp. 343–354, 1981, *J. Amer. Anim. Hosp. Assoc.,* vol. 17.

Wade et al., "Survival and Reproduction of Artificially Fed Cat Fleas, *Ctenocephalides felis* Bouché (Siphonaptera: Pulicidae)", pp. 186–189, 1988, *J. Med. Entomol.,* vol. 25, No. 3.

Young et al., Allergy to Flea Bites. V. Preliminary Results of Fractionation, Characterization, and Assay for Allergenic Activity of Material Derived from the Oral Secretion of the Cat Flea, *Ctenocephalides felis felis,* pp. 155–166, 1963, *Exp. Parasitol.,* vol. 13.

Baker et al., 1975, *J. Small Anim. Pract.,* 16 (5):317–327.

Greene et al., 1993, *Vet Immunol. & Immunopathol.,* 37 (1):15–23.

Halliwell, et al., 1985, *Vet. Immunol. & Immunopath,* 8 (3):215–23.

Kunkle et al., 1985, *J. Amer. Vet. Medical Assn.,* 186 (7):677–80.

McKeon et al., 1994, *Int. J. Parasitol.,* 24 (2):259–63.

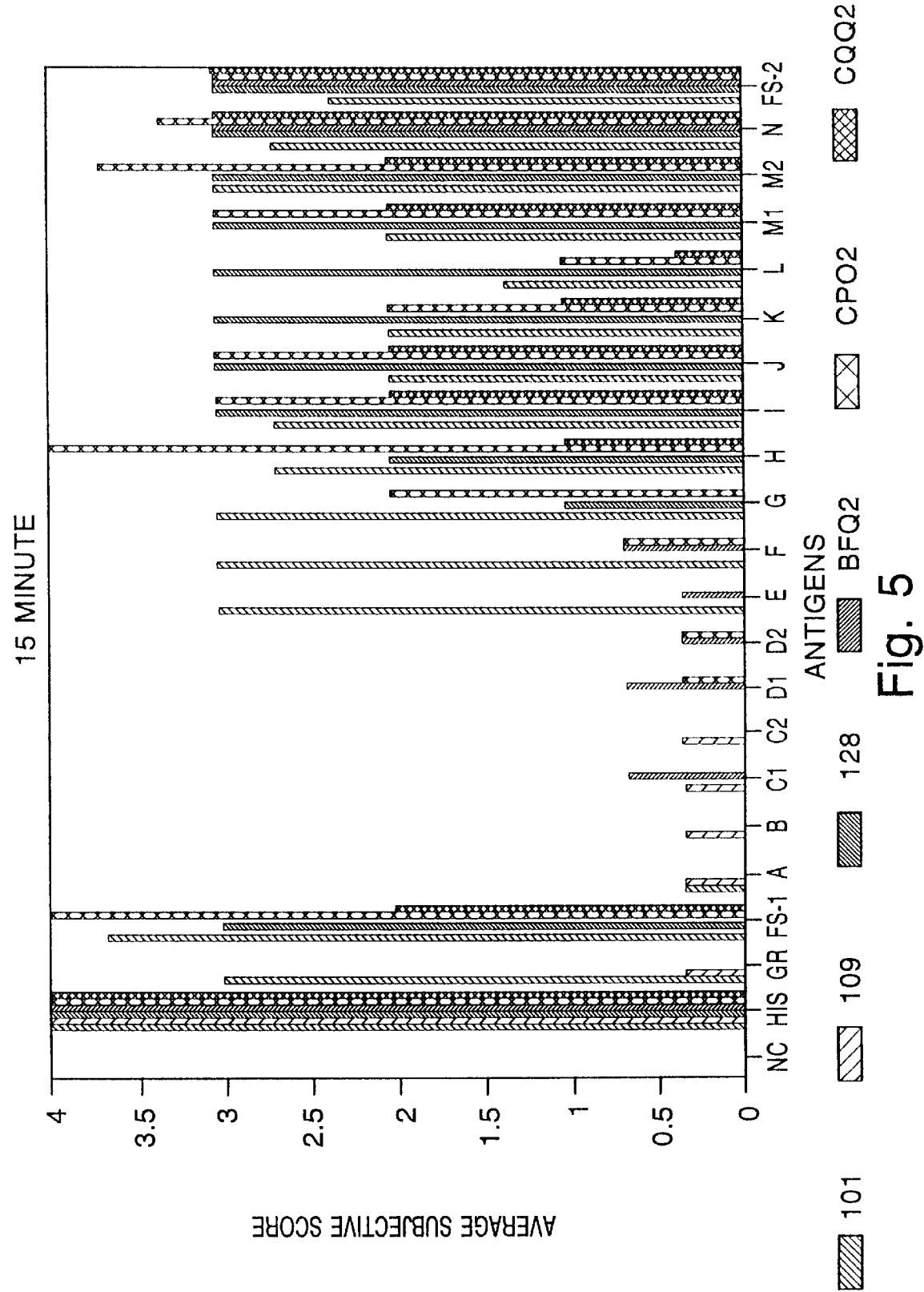

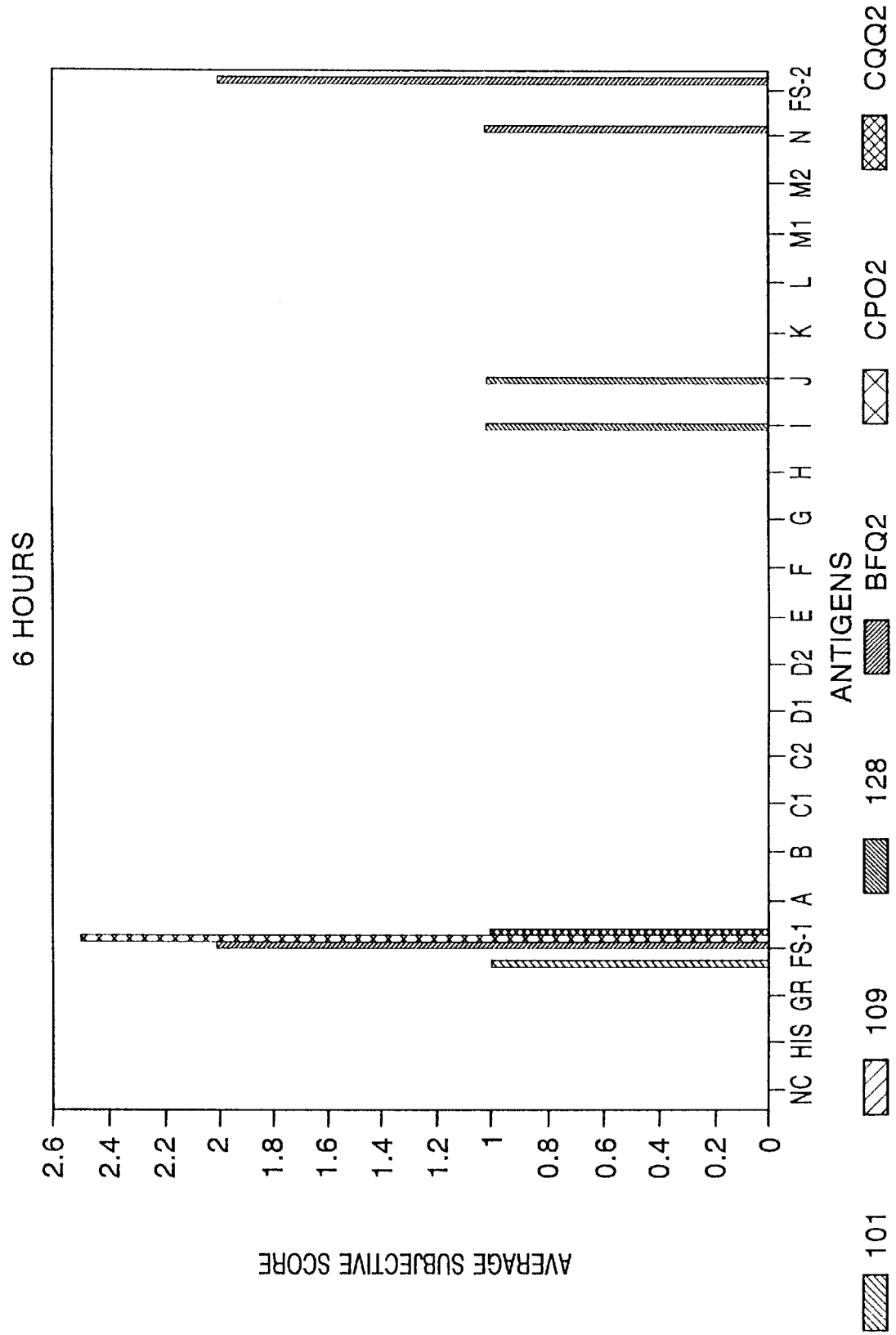

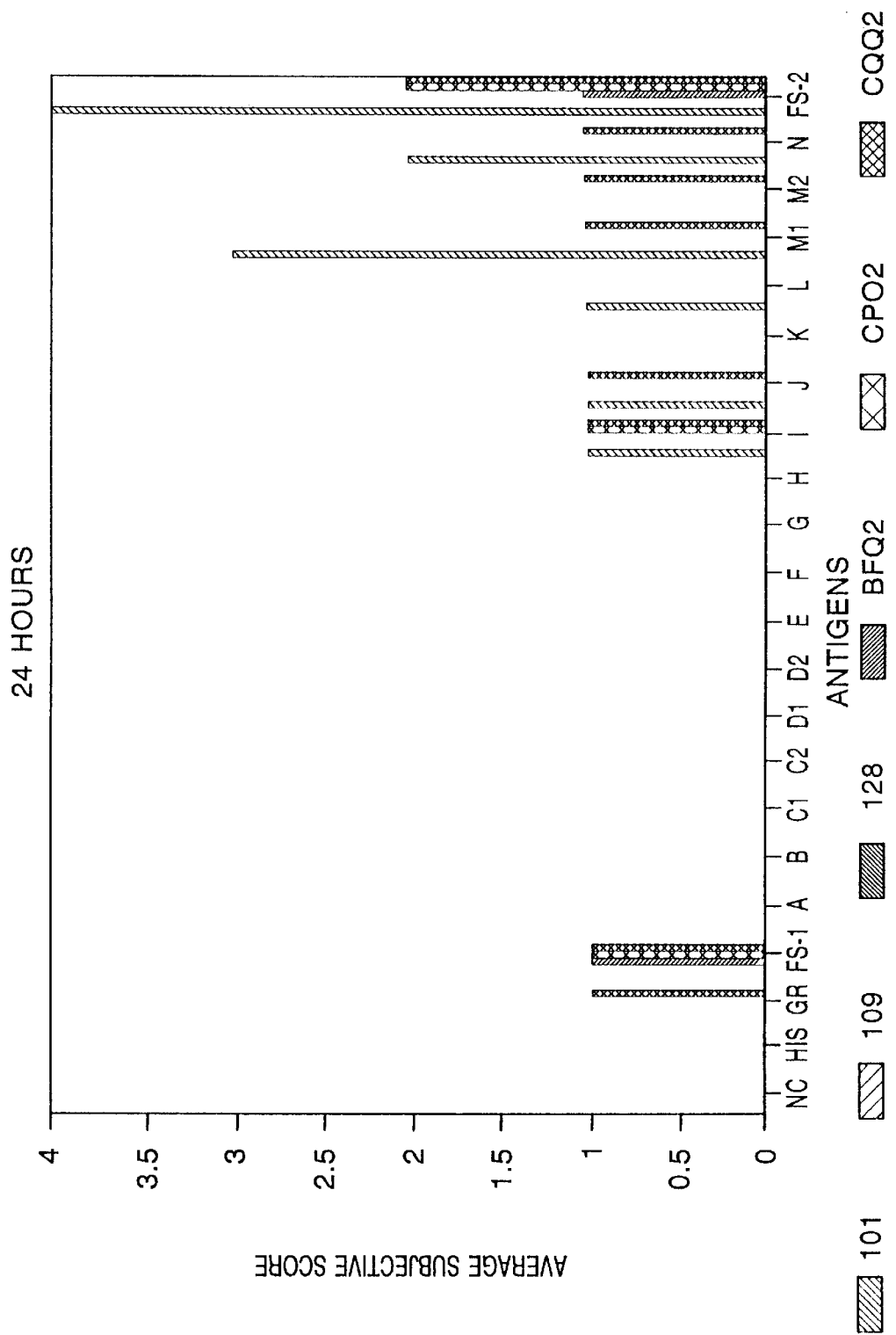

ECTOPARASITE SALIVA PROTEINS AND APPARATUS TO COLLECT SUCH PROTEINS

This is a divisional of application Ser. No. 08/319,590, filed Oct. 7, 1994, now U.S. Pat. No. 5,646,115.

FIELD OF THE INVENTION

The present invention relates to a novel product and method for isolating ectoparasite saliva proteins, and a novel product and method for detecting and/or treating allergic dermatitis in an animal.

BACKGROUND OF THE INVENTION

Bites from ectoparasites, in particular fleas, can cause a hypersensitive response in animals. In particular, hypersensitive responses to fleabites is manifested in a disease called flea allergy dermatitis (FAD). Hypersensitivity refers to a state of altered reactivity in which an animal, having been previously exposed to a compound, exhibits an allergic response to the compound upon subsequent exposures. Hypersensitive responses include Type I, Type II, Type III and Type IV hypersensitivities. Type I hypersensitivity is described as IgE-mediated hypersensitivity in which an allergen induces cross-linkage of IgE bound to Fc receptors on the surface of mast cells. This cross-linkage results in the degranulation of the mast cells. Type II hypersensitivity is described as antibody-mediated cytotoxic hypersensitivity in which antibodies bind to cell surface allergens resulting in cell destruction via complement activation. Type III hypersensitivity is described as immune complex-mediated hypersensitivity in which allergen-antibody complexes deposit in various tissues and induce inflammatory responses. A delayed hypersensitive reaction includes Type IV hypersensitivity which is described as a cell-mediated hypersensitivity in which T lymphocytes (i.e., T cells) release cytokines that activate macrophages or cytotoxic T cells which mediate cellular destruction.

A Type I hypersensitive response usually occurs within about 2 to 30 minutes following exposure to an allergenic compound, which is usually a soluble allergen. Type II and III responses can occur from about 2 to 8 hours following exposure to an allergenic compound. Alternatively, in a delayed hypersensitivity response, the allergic response by an animal to an allergenic compound typically is manifested from about 24 to about 72 hours after exposure to the compound. During the 24-hour delay, mononuclear cells infiltrate the area where the agent is located. The infiltrate can include lymphocytes, monocytes, macrophages and basophils. Lymphokines (e.g., interferon-γ) are produced which activate monocytes or macrophages to secrete enzymes (e.g., proteases) which cause tissue damage.

Foreign compounds that induce symptoms of immediate and/or delayed hypersensitivity are herein referred to as allergens. The term "allergen" primarily refers to foreign compounds capable of causing an allergic response. The term can be used interchangeably with the term "antigen," especially with respect to a foreign compound capable of inducing symptoms of immediate and/or delayed hypersensitivity. Factors that influence an animal's susceptibility to an allergen can include a genetic component and/or environmental exposure to an allergen. Animals can be de-sensitized to an allergen by repeated injections of the allergen to which an animal is hypersensitive.

FAD can have manifestations of both immediate and delayed-type hypersensitivity. Typically, an immediate hypersensitive response in an animal susceptible to FAD includes wheal formation at the site of a fleabite. Such wheals can develop into a papule with a crust, representative of delayed-type hypersensitivity. Hypersensitive reactions to fleabites can occur in genetically pre-disposed animals as well as in animals sensitized by previous exposure to fleabites.

Effective treatment of FAD has been difficult if not impossible to achieve. FAD afflicts about 15% of cats and dogs in flea endemic areas and the frequency is increasing each year. In a geographical area, effective flea control requires treatment of all animals. One treatment investigators have proposed includes desensitization of animals using flea allergens. However, reliable, defined preparations of flea allergens are needed for such treatments.

Until the discovery of the novel formulations of the present invention, flea allergens responsible for FAD had not been clearly defined. Whole flea antigen preparations have been used to diagnose and desensitize animals with FAD (Benjamini et al., 1960, pp. 214–222, *Experimental Parasitology*, Vol. 10; Keep et al., 1967, pp. 425–426, *Australian Veterinary Journal*, Vol. 43; Kristensen et al., 1978, pp. 414–423, Nord. Vet-Med, Vol. 30; Van Winkle, 1981, pp. 343–354, *J. Amer. Animal Hosp. Assoc.*, Vol. 17; Haliwell et al., 1987, pp. 203–213, *Veterinary Immunology and Immunopathology*, Vol. 15; Greene et al., 1993, pp. 69–74, *Parasite Immunology*, Vol. 15); PCT Publication No. WO 93/18788 by Opdebeeck et al.; and Van Winkle, pp. 343–354, 1981, *J. Am. Anim. Hosp. Assoc.*, vol. 32. Available commercial whole flea extracts, however, are unpredictable and, therefore, have limited usefulness.

Prior investigators have suggested that products contained in flea saliva might be involved in FAD and have also suggested methods to isolate such products: Benjamini et al., 1963, pp. 143–154, *Experimental Parasitology*, Vol. 13; Young et al., 1963, pp. 155–166, *Experimental Parasitology* 13, Vol. 13; Michaeli et al., 1965, pp. 162–170, *J. Immunol.*, Vol. 95; and Michaeli et al., 1996, pp. 402–406, *J. Immunol.*, Vol. 97. These investigators, however, have characterized the allergenic factors of flea saliva as being haptens having molecular weights of less than 6 kilodaltons (kD). That they are not proteins is also supported by the finding that they are not susceptible to degradation when exposed to strong acids (e.g., 6N hydrochloric acid) or heat. Some of the particular low molecular weight allergenic factors have also been characterized as being a highly fluorescent aromatic fraction (Young et al., ibid.). In addition, studies by such investigators have indicated that in order to be allergenic, such factors need to be associated with adjuvants and/or carriers, such as collagen or portions of the membrane used to collect the oral secretions. Moreover, the methods described to collect flea saliva factors were difficult and unpredictable. Furthermore the factors isolated by these methods were typically contaminated with material from the fleas, their culture medium or the skin-based membranes used to allow the fleas to feed.

Thus, there remains a need to more clearly define flea saliva allergens capable of inducing a hypersensitive response in animals. In addition, there remains a need to develop a method to collect substantially pure flea saliva allergens which provide predictable and less expensive preparations of allergens useful for desensitizing animals subject to, or having, FAD.

SUMMARY OF THE INVENTION

The present invention relates to, in one embodiment, a formulation comprising at least one isolated ectoparasite saliva protein, in which the ectoparasite saliva protein comprises at least a portion of an amino acid sequence, in which the portion is encoded by a nucleic acid molecule capable of hybridizing under stringent conditions with a nucleic acid molecule that encodes a flea saliva protein present in flea saliva extract FS-1 and/or FS-2. Preferred flea saliva proteins include fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and/or fspN3. In addition, the flea saliva protein of the formulation can include at least a portion of an amino acid sequence represented by SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25 and/or SEQ ID NO:26.

Another embodiment of the present invention includes a formulation comprising at least one isolated ectoparasite saliva protein, in which the ectoparasite saliva protein comprises at least a portion of an amino acid sequence, in which the portion is encoded by a nucleic acid molecule capable of hybridizing under stringent conditions with a nucleic acid molecule that encodes a flea saliva protein represented as a protein peak in FIG. 2.

One aspect of the present invention includes a formulation comprising an ectoparasite saliva product, in which the formulation, when submitted to Tris glycine SDS-PAGE, comprises a fractionation profile as depicted in a FIG. 1B, lane 13 and/or FIG. 1B, lane 14.

Yet another embodiment of the present invention includes a formulation comprising at least one isolated ectoparasite saliva product substantially free of contaminating material, the formulation being produced by a process comprising: (a) collecting ectoparasite saliva products on a collection means within a saliva collection apparatus containing ectoparasites, the apparatus comprising (i) a housing operatively connected to a chamber, the chamber having an ambient temperature warmer than the housing thereby forming a temperature differential between the housing and the chamber, the housing being capable of retaining ectoparasites, and (ii) an interface between the housing and the chamber, the interface comprising ((a)) a means capable of collecting at least a portion of saliva products deposited by ectoparasites retained in the apparatus and ((b)) a barrier means capable of substantially preventing contaminating material from contacting the collection means, in which the temperature differential attracts ectoparasites retained in the housing to attempt to feed through the barrier means and collection means and, thereby, deposit saliva products on the collection means; and (b) extracting the saliva products from the collection means to obtain the formulation. Also included in the present invention is such an apparatus and use such an apparatus to produce formulaitons comprising flea saliva products substantially free of contaminating material.

Another aspect of the present invention includes an isolated nucleic acid molecule capable of hybridizing under stringent conditions with a gene encoding a flea saliva protein present in flea saliva extract FS-1 and/or FS-2 including, but not limited to fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and/or fspN3. In particular, the nucleic acid molecule is capable of hybridizing under stringent conditions with nucleic acid sequence SEQ ID NO:20 and/or SEQ ID NO:24. Also included in the present invention are recombinant molecules and recombinant cells having a nucleic acid molecule of the present invention.

Also included in the present invention is a method for producing at least one ectoparasite saliva protein, comprising: (a) culturing a cell transformed with at least one nucleic acid capable of hybridizing under stringent conditions with a gene encoding a flea saliva protein present in flea saliva extract FS-1 and/or FS-2 to produce the protein; and (b) recovering the ectoparasite saliva proteins.

Another aspect of the present invention includes an antibody capable of selectively binding to an ectoparasite saliva product, or mimetope thereof.

Yet another aspect of the present invention includes a therapeutic composition for treating allergic dermatitis comprising any of the formulations disclosed herein. In particular, the therapeutic composition is useful for treating flea allergy dermatitis, mosquito allergy dermatitis and/or Culicoides allergy dermatitis. Moreover, particular flea saliva proteins to include in a therapeutic composition include at least a portion of at least one of the following flea saliva proteins: fspE, fspF, fspG, fspH, fspI, fspJ1, fspJ2, fspK, fspL1, fspL2, fspM1, fspM2, fspN1, fspN2 and/or fspN3. The present invention also includes a method to desensitize a host animal to allergic dermatitis, comprising administering to the animal a therapeutic composition.

The present invention further relates to an assay kit for testing if an animal is susceptible to or has allergic dermatitis, the kit comprising: (a) a formulation as disclosed herein; and (b) a means for determining if the animal is susceptible to or has allergic dermatitis, in which the means comprises use of the formulation to identify animals susceptible to or having allergic dermatitis.

According to the present invention, a method can be used to identify an animal susceptible to or having allergic dermatitis, the method comprising: (a) administering to a site on the animal a formulation of the present invention and administering to a different site on the animal a control solution selected from the group consisting of positive control solutions and negative control solutions; and (b) comparing a reaction resulting from administration of the formulation with a reaction resulting from administration of the control solution. The animal is determined to be susceptible to or to have allergic dermatitis if the reaction to the formulation is at least as large as the reaction to the positive control solution. The animal is determined not to be susceptible to or not to have allergic dermatitis if the reaction to the formulation is about the same size as the reaction to the negative control solution. In particular, the method can detect immediate hypersensitivity and/or delayed hypersensitivity.

Also according to the present invention, a method can be used to identify an animal susceptible to or having allergic dermatitis by measuring the presence of antibodies indicative of allergic dermatitis in the animal, the method comprising: (a) contacting a formulation of the present invention with a body fluid from the animal under conditions sufficient for formation of an immunocomplex between the formulation and the antibodies, if present, in the body fluid; and (b) determining the amount of immunocomplex formed, in which formation of the immunocomplex indicates that the animal is susceptible to or has allergic dermatitis. In particular, the method can be used to detect IgE antibodies as an indicator of immediate hypersensitivity in the animal.

The present invention also includes a method for prescribing treatment for allergic dermatitis, comprising: (a) identifying an animal that is susceptible to or has allergic dermatitis by an in vivo or in vitro assay comprising a formulation of the present invention; and (b) prescribing a treatment comprising administering formulation of the present invention to the animal.

BRIEF DESCRIPTION OF THE DRAWINGS

FIG. 5 illustrates the relative size of wheals produced 15 minutes after injection of various flea saliva protein formulations into flea-sensitized dogs.

FIG. 6 illustrates the relative induration of wheals 6 hours after injection of various flea saliva protein formulations into flea-sensitized dogs.

FIG. 9 illustrates the relative erythema of wheals 24 hours after injection of various flea saliva protein formulations into flea-sensitized dogs.

DETAILED DESCRIPTION OF THE INVENTION

Figure 1A:
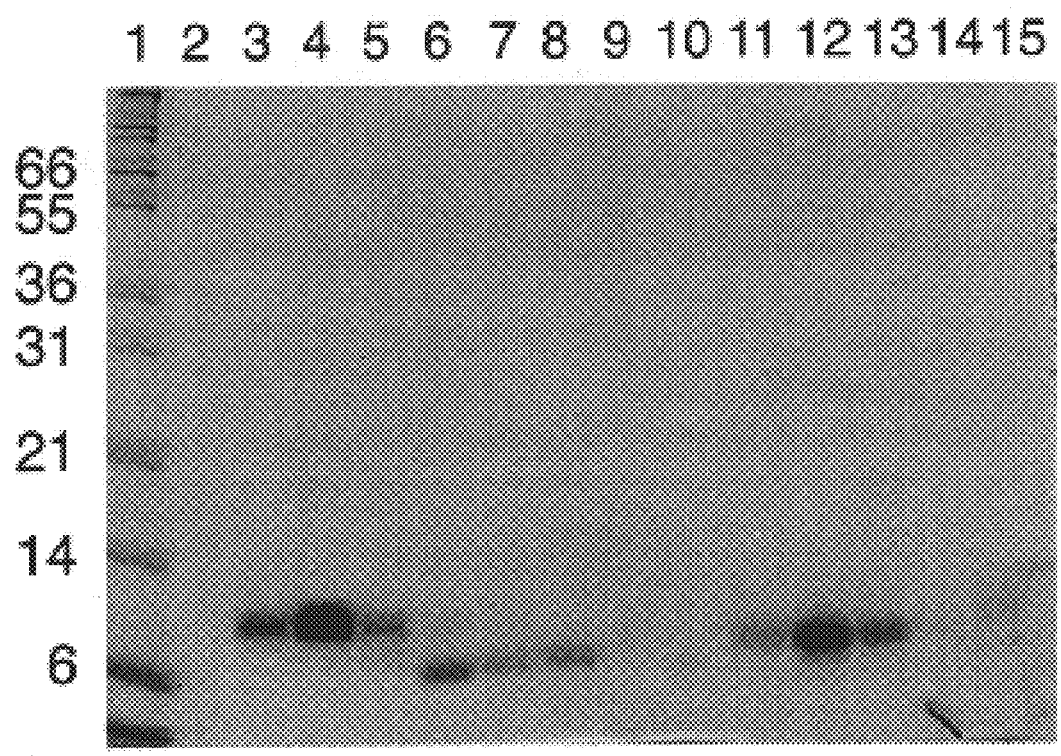
FIG. 1A illustrates the resolution of flea saliva proteins by reducing 16% Tris glycine SDS-PAGE.

The present invention includes a novel product and method for diagnosing and treating allergic dermatitis of animals to ectoparasites. The invention is particularly advantageous in that it provides for a unique formulation of ectoparasite saliva products sufficiently free of contaminants such as blood proteins, fecal material and larval culture medium, to be useful in diagnosis and therapy of allergies caused by ectoparasites. In addition, the present invention includes ectoparasite saliva products having other activities, important, for example, in a flea's ability to feed and/or counteract a host's resistance to fleas, such as products having clotting, anti-coagulant, protease, phospholipase, prostaglandin, anti-complement, other immunosuppressant, apyrase, vasoactive, and/or anti-inflammatory activities.

The invention is also particularly advantageous in that it provides an apparatus and method for reproducibly and efficiently isolating ectoparasite saliva products substantially free of contaminating material.

According to the present invention, ectoparasites are external living parasites that attach and feed through the skin of a host animal. Ectoparasites include parasites that live on a host animal and parasites that attach temporarily to an animal in order to feed. Also, according to the present invention, ectoparasite saliva refers to the material released from the mouth of an ectoparasite when the ectoparasite attempts to feed in response to a temperature differential, such as exists in an apparatus of the present invention.

Ectoparasite saliva includes ectoparasite saliva products. Ectoparasite saliva products of the present invention comprise the portion of ectoparasite saliva bound to a collecting means of the present invention (described in detail below), herein referred to as ectoparasite saliva components. As such, ectoparasite saliva products also include the portion of ectoparasite saliva extracted from a collecting means of the present invention, herein referred to as ectoparasite saliva extract. Included in ectoparasite saliva extracts are ectoparasite saliva proteins which can be isolated using, for example, any method described herein. Ectoparasite saliva extracts of the present invention can also include other ectoparasite saliva products, such as, prostaglandins and other pharmacologically active molecules.

One embodiment of the present invention is a formulation that contains ectoparasite saliva products that can be used to diagnose and/or treat animals susceptible to or having (i.e., suffering from) allergic dermatitis. Preferred types of allergic dermatitis to diagnose and/or treat using ectoparasite saliva products of the present invention include flea allergy dermatitis, Culicoides allergy dermatitis and mosquito allergy dermatitis. A preferred type of allergic dermatitis to diagnose and/or treat using ectoparasite saliva products of the present invention is flea allergy dermatitis. As used herein, an animal that is susceptible to allergic dermatitis refers to an animal that is genetically pre-disposed to developing allergic dermatitis and/or to an animal that has been primed with an antigen in such a manner that re-exposure to the antigen results in symptoms of allergy that can be perceived by, for example, observing the animal or measuring antibody production by the animal to the antigen. As such, animals susceptible to allergic dermatitis can include animals having sub-clinical allergic dermatitis. Sub-clinical allergic dermatitis refers to a condition in which allergy symptoms cannot be detected by simply observing an animal (i.e., manifestation of the disease can include the presence of anti-ectoparasite saliva protein antibodies within an affected animal but no dermatitis). For example, sub-clinical allergic dermatitis can be detected using in vivo or in vitro assays of the present invention, as described in detail below. Reference to animals having allergic dermatitis includes animals that do display allergy symptoms that can be detected by simply observing an animal and/or by using in vivo or in vitro assays of the present invention, as described in detail below.

One embodiment of the present invention is a formulation that includes one or more isolated ectoparasite saliva proteins. According to the present invention, an isolated protein is a protein that has been removed from its natural milieu. An isolated ectoparasite saliva protein can, for example, be obtained from its natural source, be produced using recombinant DNA technology, or be synthesized chemically. As used herein, an isolated ectoparasite saliva protein can be a full-length ectoparasite saliva protein or any homologue of such a protein, such as an ectoparasite saliva protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitation, amidation and/or addition of glycosylphosphatidyl inositol). A homologue of an ectoparasite saliva protein is a protein having an amino acid sequence that is sufficiently similar to a natural ectoparasite saliva protein amino acid sequence that a nucleic acid sequence encoding the homologue is capable of hybridizing under stringent conditions to (i.e., with) a nucleic acid sequence encoding the natural ectoparasite saliva protein amino acid sequence.

As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989. The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an ectoparasite saliva protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of an ectoparasite saliva protein homologue of the present invention is from about 4 to about 6 amino acids in length, with preferred sizes depending on whether a full-length, multivalent (i.e., fusion protein having more than one domain each of which has a function), or functional portions of such proteins are desired.

Ectoparasite saliva protein homologues can be the result of allelic variation of a natural gene encoding an ectoparasite saliva protein. A natural gene refers to the form of the gene found most often in nature. Ectoparasite saliva protein homologues can be produced using techniques known in the art including, but not limited to, direct modifications to a gene encoding a protein using, for example, classic or recombinant DNA techniques to effect random or targeted mutagenesis.

Preferred ectoparasite saliva proteins of the present invention, including homologues thereof, are capable of detecting and/or treating allergic dermatitis resulting from the bites of ectoparasites. A preferred ectoparasite saliva protein homologue includes at least one epitope capable of eliciting a hypersensitive response to the natural ectoparasite saliva protein counterpart. An ectoparasite saliva protein homologue can also include an epitope capable of hyposensitizing an animal to the natural form of the protein. The ability of an ectoparasite saliva protein homologue to detect and/or treat (i.e., immunomodulate or regulate by, for example, desensitizing) the hypersensitivity of an animal susceptible to or having allergic dermatitis, can be tested using techniques known to those skilled in the art. Such techniques include skin tests and immunoabsorbent assays as described in detail below. Additional preferred ectoparasite saliva proteins of the present invention have other activities that include activities important for feeding and survival of the ectoparasite.

In one embodiment, a formulation of the present invention can comprise a protein having at least a portion of an isolated ectoparasite saliva protein. According to the present invention, "at least a portion of an ectoparasite saliva protein" refers to a portion of an ectoparasite saliva protein encoded by a nucleic acid molecule that is capable of hybridizing, under stringent conditions, with a nucleic acid encoding a full-length ectoparasite saliva protein of the present invention. Preferred portions of ectoparasite saliva proteins are useful for detecting and/or treating allergic dermatitis resulting from the bites of ectoparasites. Additional preferred portions have activities important for flea feeding and survival. Suitable sizes for portions of an ectoparasite saliva protein of the present invention are as disclosed for saliva protein homologues of the present invention.

As will be apparent to one of skill in the art, the present invention is intended to apply to all ectoparasites. A formulation of the present invention can include saliva products from any ectoparasites. A preferred ectoparasite of the present invention from which to isolate saliva products (including proteins), and/or from which to identify proteins that can then be produced recombinantly or synthetically, include arachnids, insects and leeches. More preferred ectoparasites from which to obtain saliva products include fleas; ticks, including both hard ticks of the family Ixodidae (e.g., Ixodes and Amblyomma) and soft ticks of the family Argasidae (e.g., Ornithodoros, such as O. parkeri and O. turicata); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Even more preferred ectoparasite saliva products include those from fleas, mosquitos, midges, sandflies, blackflies, ticks and Rhodnius, with products from fleas, mosquitos and Culicoides being even more preferred.

A particularly preferred formulation of the present invention includes flea saliva proteins. Preferred flea saliva products include those from Ctenocephalides, Xenopsylla, Pulex, Tunga, Nosopsyllus, Diamanus, Ctopsyllus and Echidnophaga fleas, with saliva products from *Ctenocephalides canis* and *Ctenocephalides felis* fleas being even more preferred. For the purposes of illustration, many of the following embodiments discuss flea saliva proteins. Such discussion of flea saliva proteins is not intended, in any way, to limit the scope of the present invention.

In one embodiment, a formulation of the present invention is substantially free from contaminating material. Contaminating material can include, for example, ectoparasite fecal material, blood proteins from previous meals taken by an ectoparasite (e.g., fetuin, ferritin, albumin, hemoglobin and other large blood proteins), ectoparasite cuticular debris, and ectoparasite larval culture medium (e.g., blood, mouse food and sand). As used herein, a formulation that is substantially free of contaminants is a formulation that without further purification can be used as a diagnostic or therapeutic agent without causing undesired side effects. Preferably, a formulation substantially free from contaminating material comprises less than about 50 percent contaminating material, more preferably less than about 10 percent contaminating material, and even more preferably less than about 5 percent contaminating material. As such, a formulation of the present invention preferably comprises at least about 50 percent flea saliva products, more preferably at least about 90 percent flea saliva products, and even more preferably at least about 95 percent flea saliva products. A formulation of the present invention substantially free of contaminating material can include a formulation not having any blood contaminants or flea midgut contents. A formulation substantially free of contaminating material can be obtained using a saliva collection apparatus of the present invention as described in detail below.

A formulation that is substantially free of contaminating material can be identified by typical methods known to those of skill in the art. For example, the presence of contaminants can be identified by: (1) overloading and resolving a formulation by sodium dodecyl sulfate polyacrylamide gel electrophoresis (SDS-PAGE); (2) resolving a formulation by a variety of chromatography techniques; (3) screening a formulation with antibodies capable of binding to specific contaminants using, for example, immunoblot or enzyme-linked immunoassay techniques; (4) resolving a formulation by capillary electrophoresis; or (5) screening a formulation using an assay to detect hemoglobin.

One embodiment of a formulation of the present invention includes at least one or more flea saliva proteins having molecular weights ranging from about 6 kD to about 65 kD as determined by Tris-glycine SDS-PAGE, preferably using a 14% polyacrylamide gel and resolved using methods standard in the art. A preferred formulation includes one or more flea saliva proteins having molecular weights ranging from about 6 kD to about 55 kD. A more preferred formulation includes one or more proteins having elution (or migration) patterns as shown in FIG. 1.

In another embodiment, a formulation of the present invention includes at least one or more flea saliva proteins having molecular weights ranging from about 40 kD to about 300 kD as determined by Tris-glycine SDS-PAGE and resolved using methods standard in the art. Greater than 50% of the flea saliva proteins contained in such a formulation have a molecular weights ranging from about 40 kD to about 55 kD, and appear to be similar to fspN. A more preferred formulation includes one or more proteins having elution (or migration) patterns as shown in FIG. 1.

In another embodiment, a formulation of the present invention includes one or more flea saliva proteins having basic isoelectric points, or pI values. An isoelectric pH, or pI, value refers to the pH value at which a molecule has no net electric charge and fails to move in an electric field. A preferred formulation of the present invention includes proteins having a pI value of at least about pI 8.5, and more preferably of at least about pI 9.0. Flea saliva protein fspH, for example, has pI values ranging from about pI 8.5 to about pI 9.6, which may represent heterogeneity in the proteins due to allelic variation in the flea population from which the flea saliva proteins were collected.

In yet another embodiment, a formulation of the present invention includes at least a portion of one or more flea saliva products eluted from a collection means of the present invention. Examples of such formulations include flea extracts FS-1 and FS-2. The FS-1 and FS-2 fleas saliva extracts are produced according to the method described in detail in Example 2. According to the present invention, the terms FS-1 flea saliva extract or FS-2 flea saliva extract can be used interchangeably with the terms FS-1 flea saliva product mixture or FS-2 flea saliva product mixture, respectively.

Figure 1B:
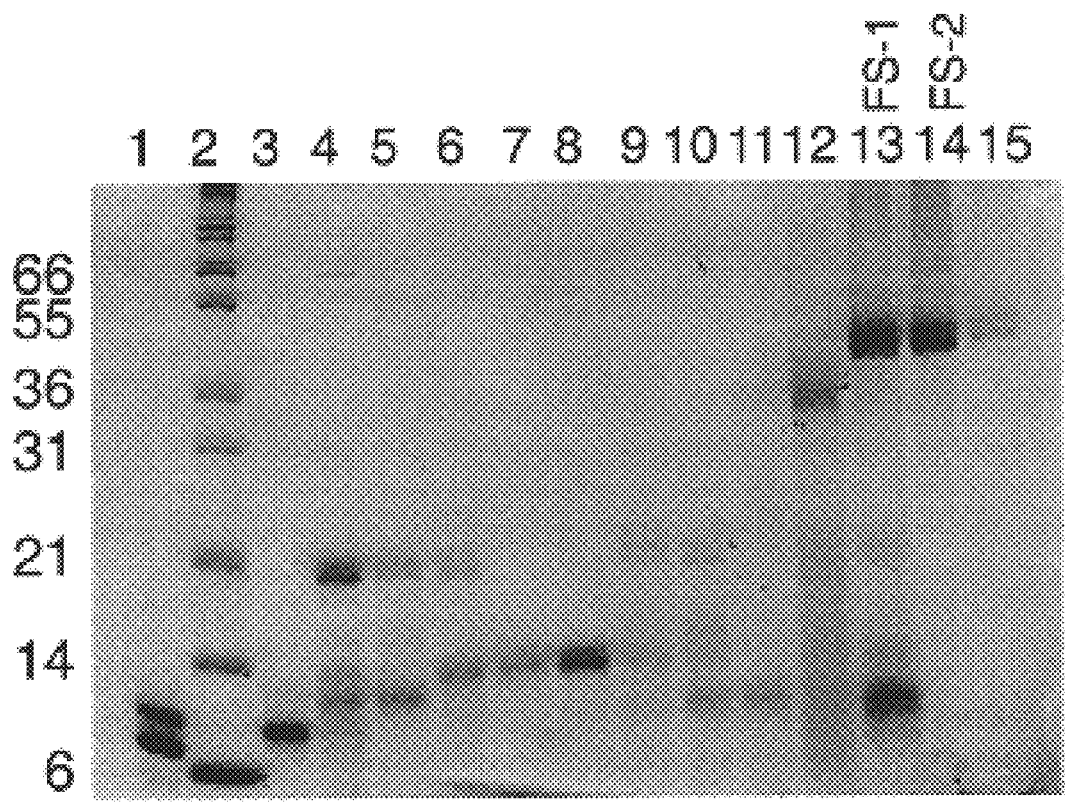
FIG. 1B illustrates the resolution of flea saliva proteins, FS-1 and FS-2 by reducing 16% Tris glycine SDS-PAGE.
Figure 2:
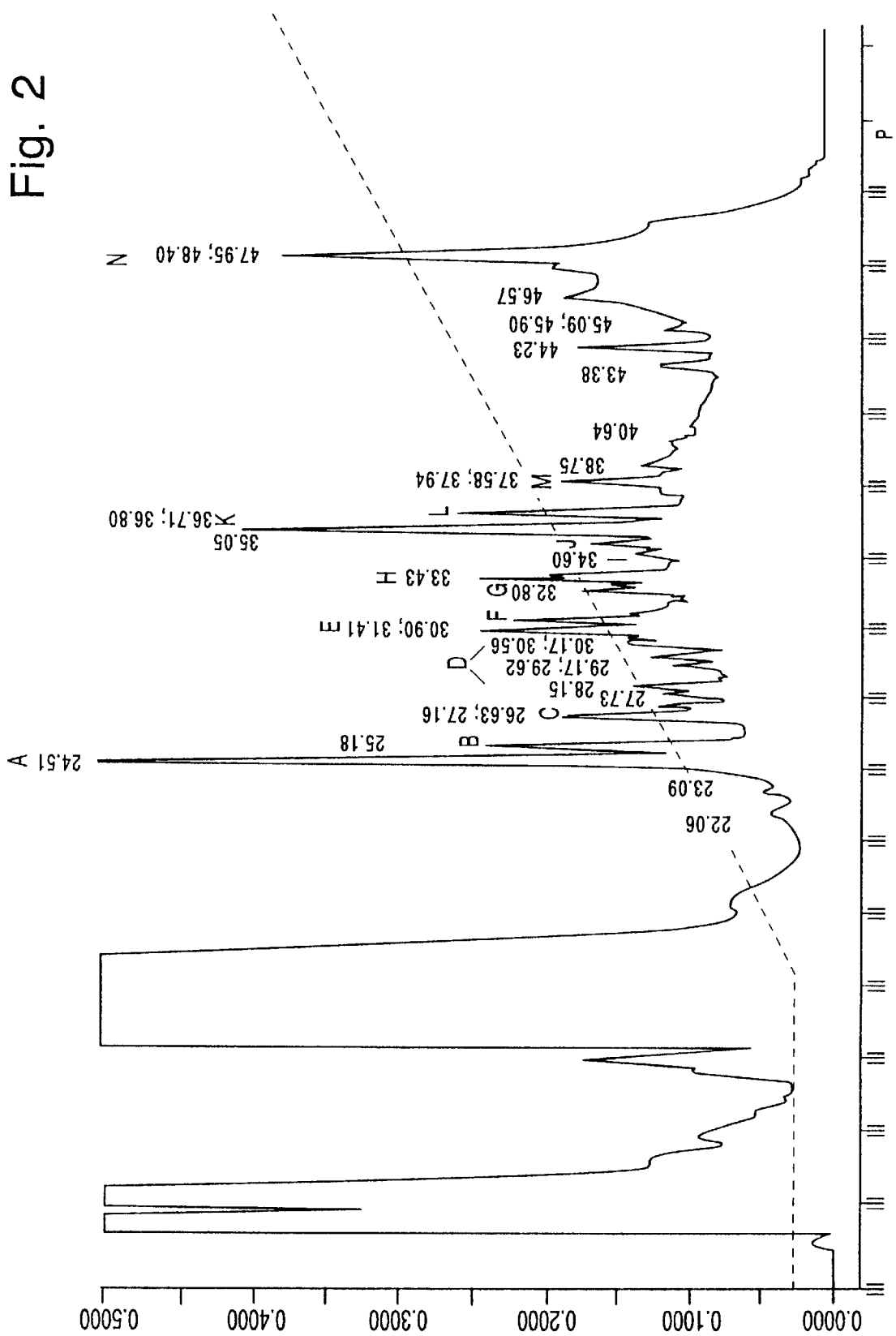
FIG. 2 illustrates the resolution of flea saliva proteins using high pressure liquid chromatography.

An FS-1 flea saliva extract includes a mixture of proteins (a) that, when submitted to reducing 16% Tris glycine SDS-PAGE, migrate as bands as are shown in FIG. 1B, lane 13; and (b) that, when submitted to reverse phase high pressure liquid chromatography (HPLC), migrate as peaks as are shown in FIG. 2. The peaks in FIG. 2 are obtained when the proteins included in FS-1 are collected using a saliva collection apparatus of the present invention as described in detail below, and further resolved into protein peaks by passing the collected proteins over a C4 HPLC column using 5% to 63% acetonitrile or 5.6% to 70% Solvent B at a flow rate of 0.8 milliliters per minute, in which Solvent A is about 0.1% TFA in water and Solvent B is about 0.085% TFA in 90% acetonitrile. Referring to FIG. 2, the peaks are referred to and depicted as peak A, peak B, peak C, peak D, peak E, peak F, peak G, peak H, peak I, peak J, peak K, peak L, peak M and peak N. Flea saliva protein contained within such peaks are referred to as fspA, fspB, fspc, fspD, fspE, fspF, fspG, fspH, fspI, fspJ, fspK, fspL, fspM and fspN. The peaks refer to the regions marked in FIG. 2 and it is to be noted that a peak does not necessarily contain just one protein. Further resolution of proteins contained within the above-referenced peaks by, for example, amino acid sequencing or SDS-PAGE gel electrophoresis, has indicated that fspC includes two proteins referred to as fspC1 and fspC2, fspD includes two proteins referred to as fspD1 and fspD2, fspj includes two proteins referred to as fspJ1 and fsJ2, fspL includes two proteins referred to as fspL1 and fspL2, fspM includes two proteins referred to as fspM1 and fspM2, and fspN includes three proteins referred to as fspN1, fspN2 and fspN3. At least partial amino acid sequence has been obtained for a number of the flea saliva proteins as represented by SEQ ID NO:1 (a partial N- (amino-) terminal amino acid sequence of fspA), SEQ ID NO:2 (an amino acid sequence, beginning at the N-terminus, that represents most of the fspH protein), SEQ ID NO:3 (a partial N-terminal amino acid sequence of an Endoproteinase Asp-N fragment of fspH, denoted fspHe), SEQ ID NO:4 (a partial N-terminal amino acid sequence of an Endoproteinase Asp-N fragment of fspH, denoted fspHh), SEQ ID NO:5 (a partial N-terminal amino acid sequence of an Endoproteinase Asp-N fragment of fspH, denoted fspHj, which also represents a partial N-terminal amino acid sequence of fspH), SEQ ID NO:6 (a partial N-terminal amino acid sequence of fspI), SEQ ID NO:7 (a partial N-terminal amino acid sequence of fspJ1), SEQ ID NO:8 (a partial N-terminal amino acid sequence of fspJ2), SEQ ID NO:9 (a partial N-terminal amino acid sequence of fspL1), SEQ ID NO:10 (a partial N-terminal amino acid sequence of fspL2), SEQ ID NO:11 (a partial N-terminal amino acid sequence of fspN1), SEQ ID NO:12 (a partial N-terminal amino acid sequence of fspN2), SEQ ID NO:13 (a partial N-terminal amino acid sequence of fspN3), SEQ ID NO:14 (a partial N-terminal amino acid sequence of fspH), SEQ ID NO:25 (a translation of the nucleic acid sequence represented by SEQ ID NO:24, corresponding to fspI), and SEQ ID NO:26 (an apparent full-length translation product of fspI). The details of how each protein was characterized is described in Examples 2 and 3.

An FS-2 flea saliva extract includes a mixture of proteins that, when submitted to reducing 16% Tris glycine SDS-PAGE, migrate as bands as are shown in FIG. 1B, lanes 14 and 15.

It is within the scope of the present invention that additional flea saliva products of interest remain on a collection means following the elution protocols to obtain FS-1 and FS-2 flea saliva extracts. It is also within the scope of the invention that a formulation of the present invention can include flea saliva products removed from a collection means by eluting with, for example, concentrations of acetonitrile higher than 50% or with other eluants.

In another embodiment, a formulation of the present invention includes at least a portion of an ectoparasite saliva protein homologue preferably having at least about 50 percent, more preferably at least about 75 percent, and even more preferably at least about 85 percent amino acid homology (identity within comparable regions) with at least a portion of at least one product contained in the saliva extracts FS-1 or FS-2. Preferred homologues include at least a portion of an ectoparasite saliva product having at least about 50 percent, more preferably at least about 75 percent, and even more preferably at least about 85 percent amino acid homology with at least a portion of one or more of the proteins fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and fspN3. As such, also included are proteins having at least a portion of one of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25 and/or SEQ ID NO:26.

In a preferred embodiment, a formulation of the present invention includes at least a portion of an ectoparasite saliva product homologue of the present invention that is encoded by a nucleic acid molecule having at least about 50 percent, more preferably at least about 75 percent, and even more preferably at least about 85 percent homology with a nucleic acid molecule encoding at least a portion of a product contained in the saliva extracts FS-1 or FS-2. A preferred ectoparasite saliva product homologue is encoded by a nucleic acid molecule having at least about 50 percent, more preferably at least about 75 percent, and even more preferably at least about 85 percent, homology with a nucleic acid molecule encoding at least a portion of one or more of the proteins fspA, fspB, fspC1, fspC2, fspD1, fspD2, fspE, fspF, fspG, fspH, fspI, fspjl, fspJ2, fspK, fspL1, fspL2, fspM1, fspM2, fspN1, fspN2 and fspN3.

Figure 3:
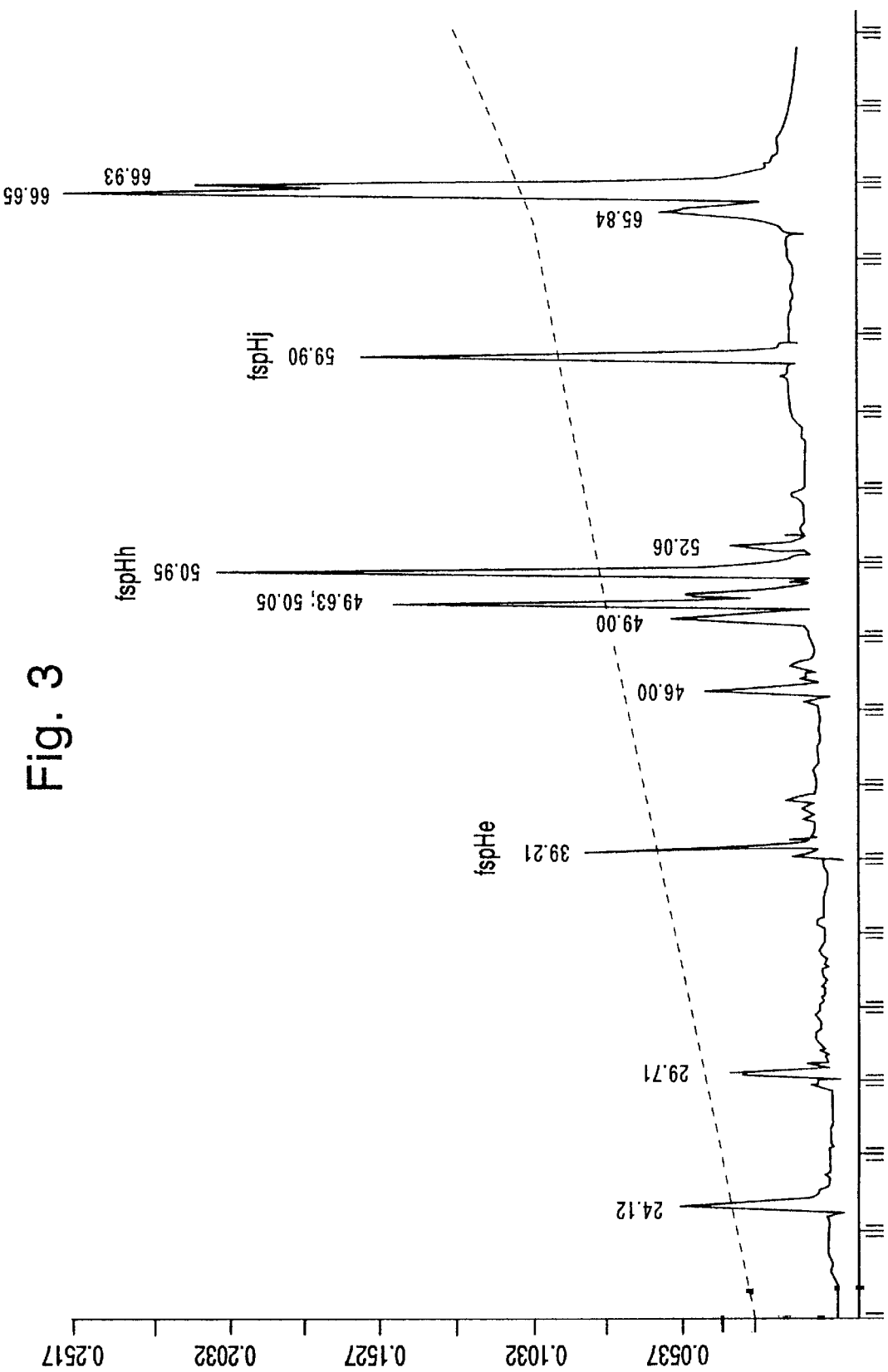
FIG. 3 illustrates the peaks obtained from reverse phase HPLC resolution of proteolytic fragments of fspH protein digested with Endoproteinase Asp-N.

In yet another embodiment, a formulation of the present invention includes a protein which, when digested with Endoproteinase Asp-N, generates proteolytic fragments that, when subjected to reverse phase HPLC, migrate with peaks as depicted in FIG. 3. The reverse phase HPLC was performed using the methods disclosed by Stone et al., Enzymatic Digestion of Proteins and HPLC Peptide Isolation, in A Practical Guide to Protein and Peptide Purification for Microsequencing, PT Matsudaira ed., Academic Press, San Diego, Calif. (i.e., Narrowbore procedure: vydac C18 reverse-phase, 300 A, 5 µm support; flow rate of 0.2 ml/min; Solvent A being 0.6% TFA in water and Solvent B being 0.052% TFA in 80% acetonitrile in water; the sample was injected at 2% B; the gradient after a hold at 2% B was 2–37.5% B over 60 min., 37.5%–75% B over 30 min., 75%–98% B over 15 min.; and detection at 214 nm). An example of such a protein is fspH, which also has the characteristics of a molecular weight of about 8613±6 daltons when determined by ESMS. A particularly preferred formulation of the present invention includes a fspH protein having the amino acid sequence represented by SEQ ID NO:2, SEQ ID NO:3, SEQ ID NO:4, SEQ ID NO:5 or SEQ ID NO:14.

In a preferred embodiment, a formulation of the present invention can include at least one isolated protein having (i.e., including) at least a portion of the amino acid sequence (using the standard one letter amino acid code):

```
Y G K Q Y S E K G G R G Q R H Q I L K K G K
Q Y S         S K     I     L   D   L
S
R
```

(SEQ ID NO:1; representing a partial N-terminal sequence of fspA).

A formulation of the present invention can also include at least one isolated protein having at least a portion of the amino acid sequence:

D R R V S K T C Q S G G K I Q S E X Q V V I K S G

Q H/Y I L E N Y X S D G R N N N P C H L F C M R

E C R S G N G G C G N G G R T R P D S K H C Y C E

A P Y S (SEQ ID NO:2), representing the N-terminal nearly complete sequence of fspH.

A formulation of the present invention can also include at least one isolated protein having at least a portion of the amino acid sequence:

D R R V S K T X Q S G G K I Q S E X Q V V I K S G

Q H/Y I L E N Y X S D G R (SEQ ID NO:14), representing a partial N-terminal sequence of fspH.

A formulation of the present invention can also include at least one isolated protein having at least a portion of the amino acid sequence:

D S K H C Y C E A P Y S (SEQ ID NO:3; representing a partial N-terminal sequence of fspHe).

A formulation of the present invention can also include at least one isolated protein having at least a portion of the amino acid sequence:

D G R N N N P C H L F C M R E C R S G N G G C G

N G G R T R P D S K H C (SEQ ID NO:4; representing a partial N-terminal sequence of fspHh).

A formulation of the present invention can also include at least one isolated protein having at least a portion of the amino acid sequence:

D R R V S K T C Q S G (SEQ ID NO:5; representing a partial N-terminal sequence of fspHj).

A formulation of the present invention can also include at least one isolated protein having at least a portion of the amino acid sequence:

E D I W K V N K K X T S G G K N Q D R K L D Q I I

Q K G Q Q V X X Q N X X K (SEQ ID NO:6; representing a partial N-terminal sequence of fspI).

A formulation of the present invention can also include at least one isolated protein having at least a portion of the amino acid sequence:

N S H E P G N T R K I R E V M D K L R K Q H P (SEQ ID NO:7; representing a partial N-terminal sequence of fspJ1).

A formulation of the present invention can also include at least one isolated protein having at least a portion of the amino acid sequence:

E I K R N S H E P G N T R K I R E V M D K L R K Q

H P (SEQ ID NO:8; representing a partial N-terminal sequence of fspJ2).

A formulation of the present invention can also include at least one isolated protein having at least a portion of the amino acid sequence:

N D K E P G N T R K I R E V M D K L R K Q A Q P R
T D G Q R P K T X I M (SEQ ID NO:9; representing a partial N-terminal sequence of fspL1).

A formulation of the present invention can also include at least one isolated protein having at least a portion of the amino acid sequence:

X L X R N D K E P G N T R K I R E V M D K (SEQ ID NO:10; representing a partial N-terminal sequence of fspL2).

A formulation of the present invention can also include at least one isolated protein having at least a portion of the amino acid sequence:

N D E L K F V F V M A K (SEQ ID NO:11; representing a partial N-terminal sequence of fspN1).

A formulation of the present invention can also include at least one isolated protein having at least a portion of the amino acid sequence:

X D E L K F V F V M A K G P S X Q A X D Y P C (SEQ ID NO:12; representing a partial N-terminal sequence of fspN2). Note that although fspN1 and fspN2 appear to have similar, if not identical, partial N-terminal sequences, the two proteins migrate differently when submitted to Tris glycine SDS-PAGE, suggesting that they are different proteins, possibly due to a carboxyl-terminal truncation of one of the proteins and/or post-translation modification, such as glycosylation.

A formulation of the present invention can also include at least one isolated protein having at least a portion of the amino acid sequence:

E L K F V F A T A R G M S H T P C D Y P (SEQ ID NO:13; representing a partial N-terminal sequence of fspN3).

It is to be appreciated that ectoparasite saliva proteins of the present invention include, but are not limited to, full-length proteins, hybrid proteins, fusion proteins, multivalent proteins, and proteins that are truncated homologues of, or are proteolytic products of, at least a portion of a protein contained in the saliva extracts FS-1 or FS-2; and preferably at least a portion of saliva protein fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and/or fspN3. As such, also included are proteins having at least a portion of one of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25 and/or SEQ ID NO:26. As used herein, the term hybrid protein refers to a single protein produced from two different proteins.

The foregoing SEQ ID NO's represent amino acid sequences deduced according to methods disclosed in the Examples. It should be noted that since amino acid sequencing technology is not entirely error-free, the foregoing SEQ ID NO's, at best, represent an apparent amino acid sequence of the ectoparasite saliva proteins of the present invention. In addition, the variation seen in the foregoing SEQ ID NO's can also be due, at least in part, to allelic variation since the proteins being sequenced were derived from populations of fleas.

According to the present invention, a formulation of the present invention can include flea saliva proteins that have undergone post-translational modification. Such modification can include, for example, glycosylation. Glycosylation can include addition of N-linked and/or O-linked oligosaccharides. It is to be appreciated that post-translational modification of a protein of the present invention can contribute to an epitope's ability to induce an allergic response against the protein in an immediate or delayed hypersensitivity response.

Another embodiment of the present invention is an isolated nucleic acid molecule capable of hybridizing, under stringent conditions, with an ectoparasite saliva protein gene encoding an ectoparasite saliva protein of the present invention. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions. An isolated nucleic acid molecule of the present invention can also be produced using recombinant DNA technology (e.g., polymerase chain reaction (PCR) amplification, cloning) or chemical synthesis. Isolated ectoparasite saliva protein nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode an ectoparasite saliva protein of the present invention or to form stable hybrids under stringent conditions with natural nucleic acid molecule isolates.

An isolated nucleic acid molecule of the present invention can include a nucleic acid sequence that encodes at least one ectoparasite saliva protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an ectoparasite saliva protein. As heretofore disclosed, ectoparasite saliva proteins of the present invention include, but are not limited to, proteins having full-length ectoparasite saliva protein coding regions, portions thereof, and other ectoparasite saliva protein homologues.

It is to be appreciated that an ectoparasite saliva protein of the present invention can be encoded by a full-length nucleic acid sequence which encodes a polyprotein. The polyprotein can be post-translationally processed into multiple proteins which are found in saliva. As used herein, an ectoparasite saliva protein gene includes all nucleic acid sequences related to a natural ectoparasite saliva protein gene such as regulatory regions that control production of an ectoparasite saliva protein encoded by that gene (such as, but not limited to, transcription, translation or post-translation control regions) as well as the coding region itself. A nucleic acid molecule of the present invention can be an isolated natural ectoparasite saliva protein nucleic acid molecule or a homologue thereof. A nucleic acid molecule of the present invention can include one or more regulatory regions, full-length or partial coding regions, or combinations thereof. The minimal size of an ectoparasite saliva protein nucleic acid molecule of the present invention is the minimal size capable of forming a stable hybrid under stringent hybridization conditions with a corresponding natural gene.

An ectoparasite saliva protein nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an allergic response in animals having allergic dermatitis or the ability of a homologue to act as an anti-coagulant) and/or by hybridization with isolated ectoparasite saliva protein nucleic acids under stringent conditions.

One embodiment of the present invention is an ectoparasite saliva protein nucleic acid molecule capable of encoding at least a portion of a flea saliva product, or a homologue thereof (e.g., saliva products of other ectoparasites), contained in the saliva extracts FS-1 or FS-2, wherein FS-1, when submitted to HPLC, resolves into peak A, peak B, peak C, peak D, peak E, peak F, peak G, peak H, peak I, peak J, peak K, peak L, peak M and/or peak N. A preferred nucleic acid molecule is capable of encoding at least a portion of one or more of the proteins fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and fspN3, or homologues thereof. As such, preferred nucleic acid molecules include, but are not limited, nucleic acid molecules that encode proteins having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25 and/or SEQ ID NO:26, or homologues thereof.

A preferred nucleic acid molecule of the present invention is capable of hybridizing under stringent conditions to a nucleic acid that encodes at least a portion of a flea saliva product, or a homologue thereof (e.g., saliva products of other ectoparasites), contained in the saliva extracts FS-1 or FS-2. Also preferred is an ectoparasite saliva protein nucleic acid molecule that includes a nucleic acid sequence having at least about 65 percent, preferably at least about 75 percent, more preferably at least about 85 percent, and even more preferably at least about 95 percent homology with the corresponding region(s) of the nucleic acid sequence encoding at least a portion of a flea saliva product, or a homologue thereof (e.g., saliva products of other ectoparasites), contained in the saliva extracts FS-1 or FS-2. A particularly preferred nucleic acid sequence is a nucleic acid sequence having at least about 65 percent, preferably at least about 75 percent, more preferably at least about 85 percent, and even more preferably at least about 95 percent homology with a nucleic acid sequence encoding at least a portion of one or more of the proteins fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and fspN3. As such, also preferred are nucleic acid molecules having at least about 65 percent, preferably at least about 75 percent, more preferably at least about 85 percent, and even more preferably at least about 95 percent homology with a nucleic acid sequence encoding at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25 and/or SEQ ID NO:26.

Such nucleic acid molecules can be a full-length gene and/or a nucleic acid molecule encoding a full-length protein, a hybrid protein, a fusion protein, a multivalent protein or a truncation fragment. More preferred nucleic acid molecules of the present invention comprise isolated nucleic acid molecules having a nucleic acid sequence as represented by SEQ ID NO:20 or SEQ ID NO:24. SEQ ID NO:20, a nucleic acid sequence that includes about 60 nucleotides of the apparent gene encoding flea saliva protein fspH, includes about 25 percent of the coding region of fspH. SEQ ID NO:24, a nucleic acid sequence that includes about 573 nucleotides of the apparent gene encoding flea saliva protein fspI, encodes a protein of about 149 amino acids, represented by SEQ ID NO:25. The entire translation product of fspi is apparently about 158 amino acids and is denoted SEQ ID NO:26.

Knowing a nucleic acid molecule of an ectoparasite saliva protein of the present invention allows one skilled in the art to make copies of that nucleic acid molecule as well as to obtain a nucleic acid molecule including additional portions of ectoparasite saliva protein-encoding genes (e.g., nucleic acid molecules that include the translation start site and/or transcription and/or translation control regions), and/or ectoparasite saliva protein nucleic acid molecule homologues. Knowing a portion of an amino acid sequence of an ectoparasite saliva protein of the present invention allows one skilled in the art to clone nucleic acid sequences encoding such an ectoparasite saliva protein. In addition, a desired ectoparasite saliva protein nucleic acid molecule can be obtained in a variety of ways including screening appropriate expression libraries with antibodies which bind to ectoparasite saliva proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or CDNA libraries can be used). To isolate flea saliva protein nucleic acid molecules, preferred cDNA libraries include cDNA libraries made from unfed whole flea, fed whole flea, fed flea midgut, unfed flea midgut, and flea salivary gland. Techniques to clone and amplify genes are disclosed, for example, in Sambrook et al., ibid. The Examples section includes examples of the isolation of cDNA sequences encoding flea saliva proteins of the present invention.

The present invention also includes nucleic acid molecules that are oligonucleotides capable of hybridizing, under stringent conditions, with complementary regions of other, preferably longer, nucleic acid molecules of the present invention that encode at least a portion of a flea saliva product, or a homologue thereof (e.g., saliva products of other ectoparasites), contained in the saliva extracts FS-1 or FS-2. A preferred oligonucleotide is capable of hybridizing, under stringent conditions, with a nucleic acid molecule that is capable of encoding at least a portion of one or more of the proteins fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and fspN3, or homologues thereof. As such, certain preferred oligonucleotides are capable of hybridizing to a nucleic acid molecule capable of encoding a protein having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12,SEQ ID NO:13, SEQ ID NO:14, SEQ ID NO:25 and/or SEQ ID NO:26, or homologues thereof. Certain preferred oligonucleotides are capable of hybridizing to nucleic acid molecules including nucleic acid sequences represented by SEQ ID NO:20, SEQ ID:24, or complements thereof.

Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of saliva proteins by ectoparasites. Such therapeutic applications include the use of such oligonucleotides in, for example, antisense-, triplex formation-, ribozyme- and/or RNA drug-based technologies. The present invention, therefore, includes such oligonucleotides and methods to interfere with the production of ectoparasite saliva proteins by use of one or more of such technologies.

The present invention also includes a recombinant vector, which includes an ectoparasite saliva protein nucleic acid molecule of the present invention inserted into any vector capable of delivering the nucleic acid molecule into a host cell. Such a vector contains heterologous nucleic acid sequences, that is nucleic acid sequences that are not naturally found adjacent to ectoparasite saliva protein nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of ectoparasite saliva protein nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

A preferred nucleic acid molecule to include in a recombinant vector of the present invention is a nucleic acid molecule that encodes at least a portion of at least one flea saliva product, or a homologue thereof (e.g., saliva products of other ectoparasites), contained in the saliva extracts FS-1 or FS-2. A particularly preferred nucleic acid molecule to include in a recombinant vector is capable of encoding at least a portion of one or more of the proteins fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and fspN3, or homologues thereof. As such, also included are nucleic acid molecules that encode a protein having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 and/or SEQ ID NO:26, or homologues thereof, and nucleic acid molecules including at least a portion of a nucleic acid sequence represented by SEQ ID NO:21 and/or SEQ ID NO:25.

In one embodiment, an isolated ectoparasite saliva protein of the present invention is produced by culturing a cell capable of expressing the protein under conditions effective to produce the protein, and recovering the protein. A preferred cell to culture is a recombinant cell that is capable of expressing the ectoparasite saliva protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell include nucleic acid molecules that encode at least a portion of a flea saliva product, or a homologue thereof (e.g., saliva products of other ectoparasites), contained in the saliva extracts FS-1 or FS-2. Particularly preferred nucleic acid molecules with which to transform a host cell are as disclosed herein for including in recombinant vectors of the present invention.

Suitable host cells to transform include any cell that can be transformed and that can express the introduced ectoparasite saliva protein. Such cells are, therefore, capable of producing ectoparasite saliva proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., *E. coli*) and insect (e.g., Spodoptera) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda ($\lambda$) (such as $\lambda.p_L$ and $\lambda.p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, Heliothis zea insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an ectoparasite saliva protein.

Expression vectors of the present invention may also contain secretory signals (i.e., signal segment nucleic acid sequences) to enable an expressed ectoparasite saliva protein to be secreted from the cell that produces the protein. Suitable signal segments include an ectoparasite saliva protein signal segment or any heterologous signal segment capable of directing the secretion of an ectoparasite saliva protein, including fusion proteins, of the present invention. Preferred signal segments include, but are not limited to, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of an ectoparasite nucleic acid molecule of the present invention can enhance the stability during production, storage and/or use of the protein encoded by the nucleic acid molecule. Furthermore, a fusion segment can function as a tool to simplify purification of an ectoparasite saliva protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of an ectoparasite saliva protein. Linkages between fusion segments and ectoparasite saliva proteins can be constructed to be susceptible to cleavage to enable straight-forward recovery of the ectoparasite saliva proteins. Fusion proteins are preferably produced by culturing a recombinant cell transformed with a fusion nucleic acid sequence that encodes a protein including the fusion segment attached to either the carboxyl and/or amino terminal end of an ectoparasite saliva protein.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. A preferred recombinant molecule includes one or more nucleic acid molecules that encode at least a portion of a flea saliva product, or a homologue thereof (e.g., saliva products of other ectoparasites), contained in the saliva extracts FS-1 or FS-2. Particularly preferred nucleic acid molecules to include in a recombinant molecule are as disclosed herein for including in a recombinant vector of the present invention.

A recombinant cell of the present invention includes any cells transformed with at least one of any nucleic acid molecule of the present invention. A preferred recombinant cell is a cell transformed with at least one nucleic acid molecule that encodes at least a portion of a flea saliva product, or a homologue thereof (e.g., saliva products of other ectoparasites), contained in the saliva extracts FS-1 or FS-2. A preferred recombinant cell is transformed with at least one nucleic acid molecule that is capable of encoding at least a portion of one or more of the proteins fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and fspN3, or homologues thereof. As such, also included are nucleic acid molecules that encode a protein having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25 and/or SEQ ID NO:26, or homologues thereof, and nucleic acid molecules including at least a portion of a nucleic acid sequence represented by SEQ ID NO:20 and/or SEQ ID NO:24. Particularly preferred recombinant cells include *E. coli* transformed with at least one of the aforementioned nucleic acid molecules.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce an ectoparasite saliva protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an ectoparasite saliva protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant ectoparasite saliva proteins may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein" refers simply to collecting the whole fermentation medium containing the protein and need not imply additional steps of separation or purification. Ectoparasite saliva proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

Ectoparasite saliva proteins are preferably retrieved in "substantially pure" form. As used herein, "substantially pure" refers to a purity that allows for the effective use of the protein as a therapeutic composition or diagnostic. For example, an animal being administered dosages of ectoparasite saliva protein isolated from a recombinant cell of the present invention should exhibit no substantial toxicity from contaminants mixed with the protein.

Ectoparasite saliva products substantially free of contaminating material can be isolated using a saliva collection apparatus of the present invention. A saliva collection apparatus of the present invention is designed to stimulate (i.e., cause) ectoparasites retained in the container to feed, and thereby to release saliva, which is collected separate from contaminating material.

Ectoparasites attach and feed from warm-blooded host animals. A host animal, as used herein, refers to an animal that ectoparasites can feed from or on. Without being bound by theory, it is believed that ectoparasites, such as fleas, possess heat receptors which enables the ectoparasite to sense a temperature differential between the warm skin of the host and the ambient air. The temperature differential stimulates (i.e., causes) the ectoparasite to feed from the warm surface (i.e., from the warm animal skin). It is also believed that motion, vibration and darkness can be sensed by ectoparasites, thereby encouraging them to feed. An ectoparasite feeds by penetrating the dermis of an animal with its mouthparts, the mouthparts remaining in that position while the ectoparasite secretes saliva to enhance feeding. During feeding, an ectoparasite can release contaminants such as blood proteins and fecal material.

A saliva collection apparatus of the present invention includes a chamber and housing such that a temperature differential between the chamber and housing of the apparatus is maintained which causes or promotes ectoparasites retained in the housing to attempt to feed from the chamber. When ectoparasites housed in such an apparatus attempt to feed in accordance with the present invention, the arthropods release saliva which is collected in such a manner that proteins, and other products, in the saliva are isolated substantially free of contaminating material. In order to collect saliva substantially free of contaminating material, an apparatus of the present invention also includes a collection means to capture saliva on a surface separate from the surface which captures the contaminating material.

A saliva collection apparatus of the present invention can be used to collect saliva from any ectoparasite such as those disclosed herein. Ectoparasites of the present invention can feed on any animal susceptible to ectoparasite infestation (i.e., a host animal), including but not limited to, a wide variety of vertebrates. Preferred host animals include mammals and birds. More preferred host animals include cats, dogs, humans, horses, rabbits, sheep, cattle, swine, goats, raccoons, ferrets, rats and opossums as well as other pets, economic food animals and animals that are hosts for fleas that infest pets and economic food animals. Particularly preferred host animals are cats and dogs.

Particularly preferred ectoparasites of the present invention from which to collect saliva include any suitable species of flea. Preferred fleas include fleas capable of infesting cats and dogs. Newly hatched fleas (i.e., recently emerged from a pupal state) that have not had a first blood meal are preferred for the following reasons: Because newly emerged fleas have not had a first blood meal, such fleas attempt to feed. Since newly emerged fleas have not had a blood meal, they also do not release as much contaminating material as do fed fleas. Newly emerged fleas live longer without a blood meal than do fleas which have had at least one blood meal. It should be noted that fed fleas can also be used with an apparatus of the present invention.

It will be obvious to one of skill in the art that a saliva collection apparatus of the present invention is useful for collecting saliva from any ectoparasite. For the purpose of illustration, a flea saliva collection apparatus of the present invention is described in detail below. Such description is not intended, in any way, to limit the scope of the present invention. It is within the skill of one in the art to collect saliva from other ectoparasites in a straightforward manner based on methods to collect saliva from fleas.

One embodiment of the present invention is a saliva collection apparatus that includes a chamber and a housing operatively connected to an interface (38) in such a manner that a temperature differential is maintained between the chamber and the housing. The interface includes a collection means and a barrier means positioned such that, in order to attempt to feed, flea mouthparts penetrate the barrier means prior to the collection means. The temperature differential between the chamber and the housing is a difference in temperature suitable to attract fleas retained in the housing to attempt to feed through the interface and, thereby deposit saliva products on the collection means. Due to the relative positioning of the collection means and the barrier means, contaminating material is deposited on the barrier means.

A flea saliva collection apparatus of the present invention includes a housing. A housing can comprise any material capable of retaining fleas that provides structural support and that can be connected to a retaining means. The housing is preferably made of a material capable of withstanding cleaning and/or sterilization procedures commonly used by those skilled in the art. As such, the housing can be reused. Preferred housing materials of the present invention include, but are not limited to, plastic, metal, rubber, wood and glass materials and combinations of such materials. More preferred housing materials include plastic and metal materials with plastic materials being even more preferred. Preferred plastic materials include plexiglass, teflon, nylon and polycarbonate. A particularly preferred plastic material is plexiglass, or other durable, break-resistant plastic, preferably clear so as to allow viewing of fleas inside the container.

In accordance with the present invention, the size of a housing of the present invention is such that the housing can support a desired number of fleas without overcrowding. Both surface area and the volume of the housing can be important. The size of the housing can vary according to the number of fleas to be retained in the housing. Preferably, the size of the housing is sufficient to maintain from about 1,000 fleas to about 6,000 fleas per housing for about 72 hours, more preferably from about 2,000 fleas to about 5,000 fleas per housing for about 72 hours, and even more preferably from about 3,000 fleas to about 4,000 fleas per housing for about 72 hours.

A suitable height for a housing of the present invention is a height that is sufficiently high to allow room for fleas to move about while feeding. The height of a housing for fleas is preferably from about 1.0 centimeters (cm) to about 3.0 cm, more preferably from about 1.5 cm to about 2.5 cm, and even more preferably from about 1.8 cm to about 2.2 cm.

The shape of a housing of the present invention can be any shape having at least one flat surface suitable for feeding by fleas contained within the housing. A housing of the present invention is preferably shaped as a cylinder, a box having four or more sides, a half-dome, or a half cylinder. A particularly preferred shape is a short cylinder.

The diameter of a preferred housing of the present invention can vary widely. Different diameter containers can be used according to, for example, the number of fleas to be placed into the housing without overcrowding. The interior diameter of a rounded housing of the present invention is preferably from about 4.0 cm to about 5.5 cm, more preferably from about 4.5 cm to about 5.5 cm, and even more preferably about 5.0 cm.

According to the present invention, the size, shape, height, and diameter of the housing can vary for different ectoparasites depending upon the size and number of arthropods retained in the housing.

In accordance with the present invention, a housing is operatively connected to a retaining means and an exchange means. As used herein, "operatively connected" refers to combining portions of a saliva collection apparatus of the present invention in such a manner that fleas can be retained within the apparatus and can deposit saliva on the collection means. A retaining means of the present invention is penetrable by the mouthparts of fleas. A retaining means of the present invention can comprise any material or combination of materials that is suitable for retaining fleas and through which fleas can feed (i.e., the retaining means is penetrable by flea mouthparts). As such, the retaining means may comprise a material having openings sufficiently large (i.e., large enough) for flea mouthparts to penetrate, but sufficiently small (i.e., small enough) so as to effectively prevent loss of any fleas retained therein. Preferred retaining means comprise a material having openings of from about 0.25 millimeters (mm) to about 0.50 mm, more preferably having openings of from about 0.30 mm to about 0.50 mm, and even more preferably having openings of from about 0.35 mm to about 0.45 mm. One of skill in the art will recognize that the size of the openings can vary according to the type of ectoparasite retained in the housing of an apparatus. For example, maintenance of particularly small ectoparasites such as, but not limited to, lice may require retaining means having smaller openings. Conversely, a retaining means for hard ticks, which are ectoparasites that cement their mouthparts into the host animal, require larger openings, preferably in the range of about 1 mm.

Preferred materials for use as retaining means include, but are not limited to, metallic mesh, nylon mesh, plastic film, cloth and combinations of such materials. More preferred retaining means include nylon mesh and metal mesh, and an even more preferred retaining means includes nylon mesh. The collection apparatus can be retrofitted with a variety of retaining means. Preferred retaining means are reusable.

An exchange means of the present invention can comprise any material or combination of materials capable of maintaining a permissive environment for fleas within the housing by allowing the exchange of gas, humidity and heat between the interior environment of the housing and the environment exterior to the housing. The housing can be retrofitted with different exchange means having different gas, humidity and heat permeabilities. As used herein, the term gas refers to any atmospheric gases required for flea survival, including, but not limited to, carbon dioxide, oxygen, and nitrogen. Gas can also refer to gaseous products produced by fleas while maintained in a housing of the present invention, such as gaseous products of metabolism including expirations or gases from feces.

Exchange means of the present invention are comprised of materials having openings that are sufficiently large to allow gas, heat and humidity to escape, but sufficiently small so as to effectively prevent loss of fleas. Preferred exchange means comprise a material having openings of from about 0.10 millimeters (mm) to about 0.45 mm, more preferably having openings of from about 0.10 mm to about 0.30 mm, and even more preferably having openings of from about 0.13 mm to about 0.15 mm.

Preferred materials to use as an exchange means include, but are not limited to, metallic mesh, nylon mesh, plastic, cloth and combinations of such materials. More preferred exchange means include nylon mesh, metal mesh, and combinations of such materials and an even more preferred exchange means includes nylon mesh. Preferred exchange materials are reusable.

In accordance with the present invention, an apparatus includes a chamber operatively connected to a housing. A chamber of the present invention is capable of maintaining an internal temperature suitable to create a temperature differential between a housing and a chamber of an apparatus which promotes deposition of saliva by fleas retained in the housing on a collection means of an apparatus. A preferred chamber is also capable of maintaining an internal humidity level suitable for the survival of ectoparasites contained in the apparatus (e.g., suitable to prevent desiccation of the ectoparasites). A chamber of the present invention is also capable of being attached to an artificial feeding system as described in detail in the Examples. A chamber can comprise any material capable of maintaining suitable temperature and humidity levels within the chamber. A chamber is preferably made of a material capable of withstanding cleaning or sterilization procedures commonly used by those skilled in the art. As such, a chamber can be reused. Preferred chamber materials of the present invention include, but are not limited to, glass, plastic, metal, rubber, and wood materials and combinations of such materials. More preferred chamber materials include glass and plastic materials with glass materials being even more preferred.

In accordance with the present invention, the size of a chamber of the present invention is such that the chamber can maintain a suitable temperature level to stimulate fleas to. deposit saliva on the collection means of the apparatus. The size of the chamber can vary according to the amount of blotting material (as described in detail below) to be placed in the chamber, the diameter of the collection means to be attached to the chamber or whether the chamber is to be attached to an artificial feeding system as described in detail in the Examples. Preferably, the height of a chamber of the present invention is high enough to allow a suitable amount of blotting material to be placed in the chamber, such that the blotting material maintains a humidity level in the chamber suitable for flea survival. The height of a chamber is preferably from about 1.0 cm to about 7.0 cm, more preferably from about 2.0 cm to about 6.0 cm, and even more preferably from about 3.0 cm to about 5.0 cm.

In accordance with the present invention, the shape of a chamber can be any shape having at least one open end to which an interface of the present invention can be attached. A chamber of the present invention is preferably shaped as a cylinder open at both ends or a cylinder open at one end. A particularly preferred shape is a cylinder open at both ends.

The diameter of a preferred chamber of the present invention can vary widely. Different diameter chambers can be used according to, for example, the diameter of the interface to be attached to the chamber or the diameter of the housing to be attached to the chamber. The interior diameter of a chamber of the present invention is preferably from about 2.0 cm to about 6.5 cm, more preferably from about 3.0 cm to about 5.5 cm, and even more preferably from about 4.0 cm to about 4.5 cm.

A chamber of the present invention can contain a blotting means suitable for maintaining a humidity level in the chamber suitable for flea survival. Methods for maintaining suitable humidity levels are described in detail below. A chamber of the present invention can contain food or water, but preferably is humid (i.e., damp but not wet) and does not contain food.

A saliva collection apparatus of the present invention includes an interface. An interface of the present invention includes means capable of collecting saliva products substantially free of contaminating material. As such, an interface of the present invention is penetrable by flea mouthparts but capable of keeping contaminating material, such as blood and fecal material, separate from flea saliva products secreted by fleas as they attempt to feed. An interface of the present invention comprises a means for collecting saliva products and a means for creating a barrier between contaminating material and collected saliva products.

A collection means of the present invention can be of any material capable of collecting (i.e., adsorbing) at least a portion of saliva proteins deposited (i.e., secreted) by retained fleas that are attempting to feed through the interface. In addition, a collection means of the present invention is capable of collecting saliva components other than saliva proteins deposited by fleas attempting to feed through the interface. The collection means is such that saliva products not only can bind to the collection means but also can be eluted (i.e., extracted) therefrom upon exposure to a suitable eluent (i.e., extractant). As such, preferred collection means materials of the present invention include materials that are hydrophobic and have a low binding capacity since saliva components are easily eluted from such material. The material of a collection means of the present invention is also capable of being penetrated by the mouthparts of fleas. Preferred collection means materials of the present invention include, but are not limited to, nylon, nitrocellulose, CM-derivatized, diethylaminoethyl (DEAE)-derivatized, paper, polysulfone, cellulose ester, polytetrafluoroethylene (PTFE) and polyvinylidene fluoride (PVDF) membranes. More preferred collection means materials include PVDF. A preferred PVDF collection means material includes Durapore™.

The shape of a collection means of the present invention can vary according to the shape of the chamber to which the collection means is to be attached. A preferred shape of a collection means includes, but is not limited to, a round shape or a box-like shape having four or more sides, with a round shape being more preferred.

The size of a collection means of the present invention can also vary according to the size of the chamber to which the collection means is to be attached. The size of a collection means is preferably larger than the open end of a chamber, thereby preventing the collection means from passing into the chamber. The size of a collection means is preferably from about 2.2 cm to about 6.5 cm in diameter, more preferably from about 3.2 cm to about 5.7 cm, and even more preferably from about 4.2 cm to about 4.7 cm.

A saliva collection apparatus of the present invention provides for a novel barrier means which enables collection of ectoparasite saliva substantially free of contaminating material. A barrier means of the present invention can be any material capable of substantially preventing contaminating material from contacting the collection means (i.e., substantially prevents the passage of contaminating material such as flea fecal material and blood products through the collection means), but is also capable of being penetrated by the mouthparts of fleas and of allowing the passage of saliva through the barrier means. Preferably, the thickness of a barrier means material of the present invention is microns thick. Preferred barrier means materials of the present invention include, but are not limited to, very thin plastic, teflon, cloth, paper, paraffin and wax materials. More preferred barrier means materials of the present invention include stretched plastic, with Saran Wrap™ and particularly Parafilm™, stretched very thin (i.e., as thin as can be stretched by machine and/or hand), being even more preferred.

The size of a barrier means of the present invention can vary according to the size of the chamber to which the barrier means is to be attached. The size of the barrier means preferably is sufficiently large that the barrier means can extend up the sides of a chamber of the present invention, thereby enabling the barrier means to be secured to the chamber. The size of the barrier means is sufficiently small such that the barrier means does not interfere with, for example, the ability of the saliva collection apparatus containing the chamber to be attached to an artificial feeding system.

According to the present invention, a collection means and a barrier means are operatively connected to a chamber of a saliva collection apparatus in such a manner that fleas retained in the housing of such apparatus are capable of penetrating both the barrier means and the collection means to deposit saliva on the collection means. A collection means of the present invention preferably is removably attached to a site on a chamber by a barrier means. A preferred site of attachment of a collection means and a barrier means is the portion of a chamber designed to interface with a housing. A more preferred site of attachment of a collection means and a barrier means is the open end of a chamber.

A saliva collection apparatus of the present invention can also include a blotting means. A blotting means of the present invention is capable of maintaining a humidity within the apparatus suitable for flea survival and, as such, is capable of retaining liquid for the period of time fleas are retained in the apparatus. As such, a blotting means can be any suitable absorbent material. Preferred blotting means include natural and synthetic sponges, foam, paper, cloth, and agarose. More preferred blotting means material include sponges and paper, with filter paper being even more preferred. In a particularly preferred embodiment, one or more pieces of VWR Blotting Pads #320 (available from VWR Scientific, Denver, Colo.) comprise a blotting means.

As stated above, a saliva collection apparatus of the present invention is capable of maintaining a temperature differential between a housing and a chamber of the apparatus. A suitable temperature differential within an apparatus of the present invention includes a temperature differential which stimulates fleas retained in the apparatus to penetrate the interface of the apparatus and deposit saliva on the collecting means. Preferred temperatures in a chamber of the present invention range from about 20° C. to about 45° C., whereas preferred temperatures in a housing of the present invention range from about 5° C. to about 35° C. In a preferred embodiment, the temperature in the chamber ranges from about 35° C. to about 40° C. and the temperature in the housing ranges from about 10° C. to about 30° C. A particularly preferred chamber temperature ranges from about 35° C. to about 37° C.; and a particularly preferred housing chamber temperature is from about 20° C. to about 27° C.

The survival of ectoparasites can be affected by humidity. As such, the humidity level in a housing of an apparatus of the present invention is suitable for maintaining the survival of ectoparasites retained therein. Suitable relative humidity levels within an apparatus of the present invention can vary depending upon the ectoparasite contained within the apparatus. As used herein, relative humidity refers to the degree of atmospheric water vapor relative to the maximum degree of atmospheric water vapor that results in precipitation. Thus, relative humidity is expressed in percent humidity, wherein 100% humidity represents saturation of atmospheric water vapor. Preferred humidity levels in a chamber of the present invention range from about 50% to about 100%, whereas preferred humidity levels in a housing of the present invention range from about 40% to about 60%. In a preferred embodiment, the humidity levels in the chamber ranges from about 50% to about 94% and the humidity level in the housing is about 50%.

Another embodiment of the present invention is the use of contrasting colors to attract fleas. For example, at least one surface of a collection apparatus of the present invention can be of a color sufficiently dark to attract fleas to penetrate the interface of the apparatus. Without being bound by theory, it is believed that fleas are capable of sensing light from dark and preferably tend to feed towards a dark surface. Therefore, according to the present invention, a chamber can be darker than a housing, thereby attracting fleas to the interface between the chamber and the housing. Suitable dark colors include colors ranging from black to light brown, preferably black.

Figure 4A:
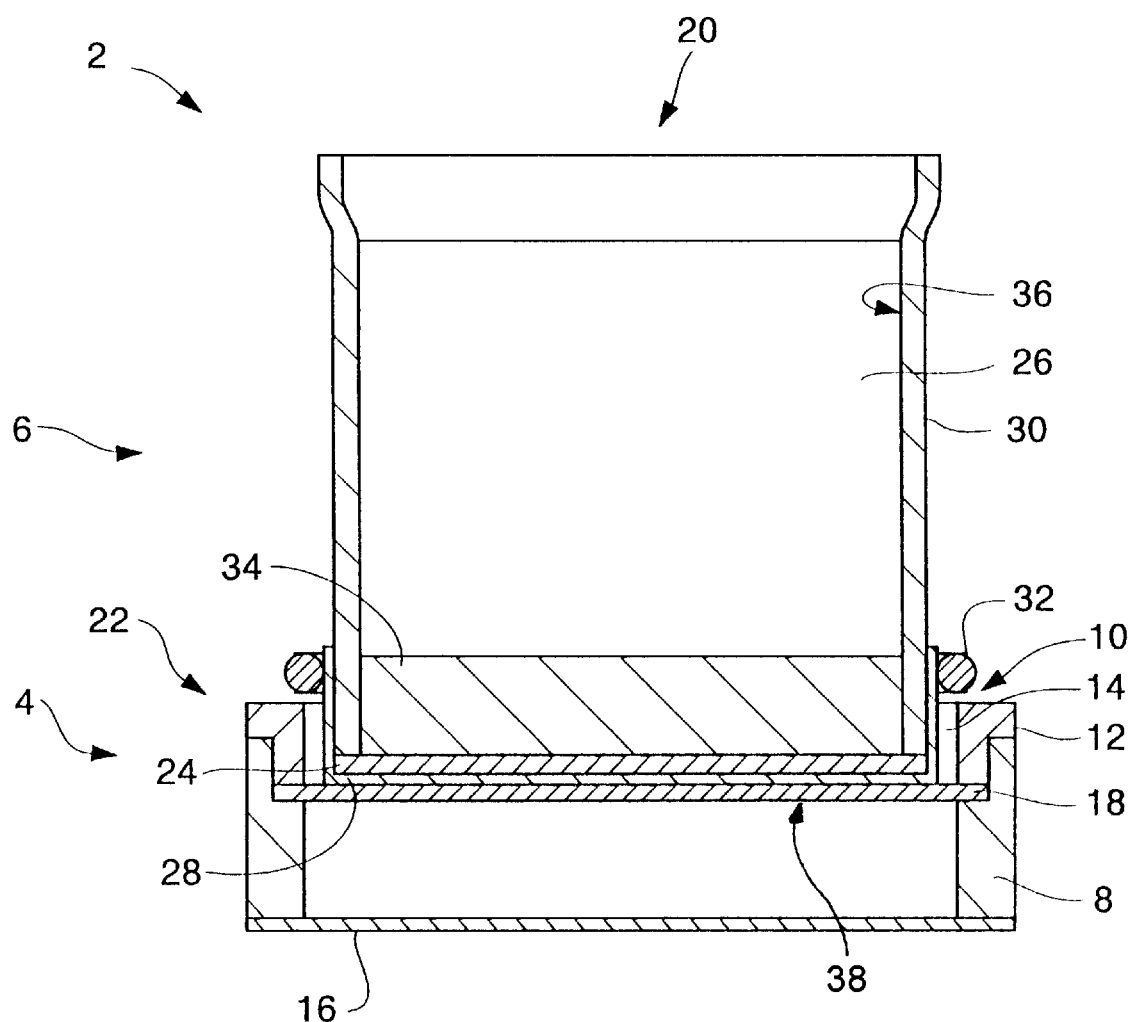
FIG. 4a illustrates a cross-section of a flea saliva collection apparatus of the present invention.
Figure 4B:
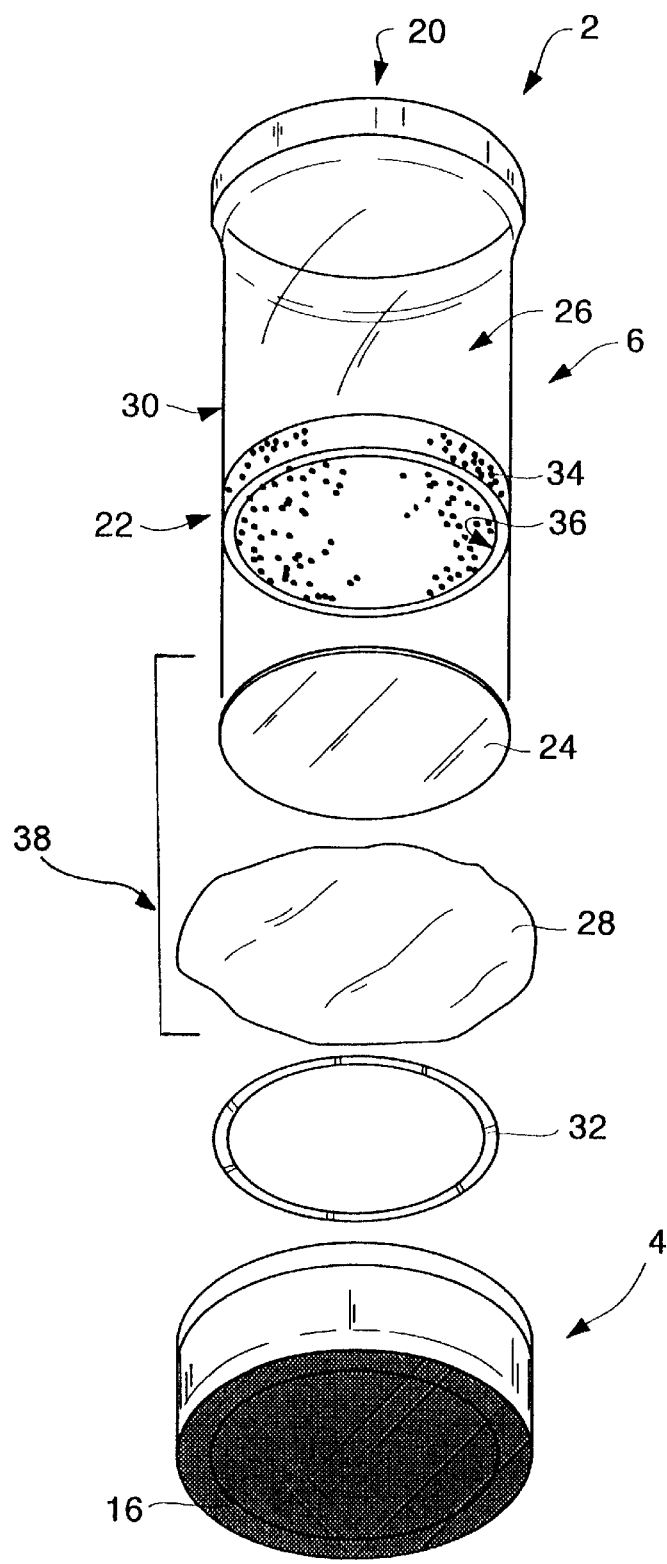
FIG. 4b illustrates a blow-out of a flea saliva collection apparatus of the present invention.

A preferred embodiment of a collection apparatus of the present invention is depicted in FIGS. 4A and 4B. A saliva collection apparatus (2) is separable into a housing (4) and a chamber (6). A cross-section of a saliva collection apparatus of the present invention (2) is shown in FIG. 4A. Referring to FIGS. 4A and 4B, the housing (4) has an open-ended cylinder having a first portion (8) and a second portion (10). The second portion (10) of the housing (4) has an outer diameter (12) and an inner diameter (14). An exchange means (16) is operatively attached to one end of the first portion (8) of the housing (4) and a retaining means (18) is attached at the opposite end of the first portion (8), between the first portion (8), and the outer diameter (12) and inner diameter (14) of the second portion (10). The exchange means (16) and retaining means (18) are attached in a manner that prevents fleas from escaping. Means of attaching an exchange means (16) and a retaining means (18) to the first portion (8) of the housing (4) include, but are not limited to, rubber cement, glue, tape, solder and araldite. A preferred means of attachment is rubber cement.

The chamber (6) of the saliva collection apparatus (2) has an open ended cylinder having a top end (20) and a bottom end (22). The top end (20) has a suitable diameter to enable the attachment of the chamber (6) to an artificial feeding system such as that described in detail in the Examples. The bottom end (22) has a suitable diameter such that the bottom end (22) can be reversibly attached to the housing (4) in such a manner as to provide a sliding fit. An interface (38) is provided between the housing (4) and the chamber (6). The interface (38) includes a collection means (24) and a barrier means (28). The bottom end (22) is covered by a collection means (24). The collection means (24) has a larger diameter than the inner circumference of the bottom end (22) of the chamber (6), thereby preventing the collection means (24) from passing into the inner space (26) of the chamber (6). Preferably, the diameter of the collection means (24) is not greater than the outer circumference of the bottom end (22) of the chamber (6). The collection means (24) can be connected to the bottom end (22) in order to provide a detachable connection, thereby facilitating removal of the collection means (24) from the saliva collecting apparatus (2) to recover saliva products from the collection means (24).

A collection means (24) attached to the bottom end (22) of a chamber (6) is covered by a barrier means (28). The barrier means (28) is operatively connected to a chamber (6) in such a manner that a seal is formed preventing contact of the collection means (24) by contaminating material deposited by fleas. The barrier means (28) can be connected to the chamber (6) in order to provide a detachable connection. Preferably, the barrier means (28) comprises a stretchable plastic material, such as Parafilm™, which is stretched as thin as possible across a collection means (24) contacting the bottom end (22) of a chamber (6) and further stretched along the sidewall (30) of the chamber (6) towards the top end (20) of the chamber (6). The barrier means (28) can be further secured to the sidewall (30) of the chamber (6) using a rubber seal (32). The rubber seal (32) detachably connects the portion of the barrier means (28) which meets the sidewall (30) of the chamber (6), thereby further securing the collection means (24) to the chamber (6) and seal in the chamber (6) environment.

Blotting (absorbent) material can be placed in the inner space (26) at the bottom end (22) of a chamber (6) to form a blotting means (34). The blotting means (34) can comprise one or more individual blotting pads (e.g., pieces of blotting material). Preferably, the blotting means (34) is from about 2.0 mm thick to about 15.0 mm thick (when dry) when placed in a 47 cm high chamber (6), more preferably is from about 2.2 mm thick to about 12.5 mm thick (when dry) when placed in a 47 mm high chamber (6), and even more preferably is from about 2.45 mm thick to about 10.0 mm thick (when dry) when placed in a 47 mm high chamber (6). In a particularly preferred embodiment, the blotting means (34) comprises from about 2 to 6 pieces of VWR Blotting Pads #320, and preferably from about 3 to 5 pieces of VWR Blotting Pads #320. The diameter of the blotting means (34) is selected to contact the inner sidewall (36) of the chamber (6). The blotting means (34) is preferably sufficiently pre-wetted to provide humidity to the chamber (6) but not so wet that liquid drips from the blotting means (34). The blotting means (34) is juxtaposed to the side of the collection means (24) facing the top end (20) of the chamber (6). The blotting means (34) can directly contact the collection means (24) in a detachable manner.

The chamber (6) is reversibly separable from the housing (4). The chamber (6) can be interconnected to the housing (4) in any reversibly secure manner such as sliding, snapping or screwing together. Preferably, the chamber (6) slides into the housing (4) and is secured using rubber bands.

The relative height dimensions of the chamber (6) can vary relative to the housing (4). Typically, the height dimension of the chamber (6) is greater than the housing (4). Preferably, the height of the chamber (6) ranges from about 1.0 cm to about 7.0 cm, more preferably from about 2.0 cm to about 6.0 cm, and even more preferably the from about 3.0 cm to about 5.0 cm. The height of the housing (4) preferably ranges from about 1.0 cm to about 3.0 cm, more preferably from about 1.5 cm to about 2.5 cm, and even more preferably from about 1.8 cm to about 2.2 cm.

One embodiment of the present invention is a method to collect saliva products from ectoparasites using an apparatus of the present invention. Such a method is particularly advantageous because it enables isolation of ectoparasite saliva, including saliva proteins, substantially free of contaminating material. As such, the method can be used, for example, to characterize ectoparasite saliva proteins and to isolate ectoparasite saliva proteins for diagnostic and therapeutic use.

One embodiment of the present method includes the steps of: (a) collecting ectoparasite saliva products on a collection means within a saliva collection apparatus which contains ectoparasites in the housing of the apparatus; and (b) extracting (i.e., eluting) the collected ectoparasite saliva products from the collection means with a solution to form an extracted product-containing solution. Such an extracted solution can be used directly as a formulation of the present invention or can be submitted to further steps of fractionation and/or purification as described in detail herein, to form additional formulations of the present invention. Examples of such extracted solutions include FS-1 and FS-2.

In accordance with the present invention, a saliva collection apparatus containing the ectoparasites has an interface between the chamber and the housing comprising a collection means capable of collecting at least a portion of saliva products deposited by ectoparasite retained in the apparatus and a barrier means capable of substantially preventing contaminating material from contacting the collection means. The ectoparasites contained in the apparatus are maintained under conditions such that there is a temperature differential between the chamber and the housing; that is, the chamber of the apparatus has a temperature warmer than the temperature of the housing containing the ectoparasite, such that the warmer temperature in the chamber attracts the ectoparasites retained in the housing to attempt to penetrate the barrier means and collection means, thereby depositing saliva products on the collection means.

In one embodiment, the method of collecting saliva products includes pre-wetting a collection means of the present invention prior to positioning the collection means in an apparatus of the present invention. A pre-wetting solution suitable for the present invention is capable of facilitating the adsorption (i.e., collection) of saliva products in such a manner that the products can also be extracted during an extraction step (i.e., when exposed to an appropriate solvent). A suitable pre-wetting solution of the present invention includes any buffer that is non-toxic to ectoparasites and has a physiological pH. Examples of suitable buffers include, phosphate buffered saline, water, phosphate buffer, HEPES buffer (N-2-hydroxyethylpiperazine-N'-2-ethanesulfonic acid buffered saline), TES buffer (Tris-EDTA buffered saline), Tris buffer and TAE buffer (Tris-acetate-EDTA). A preferred prewetting solution includes sterile water containing 50 U/ml penicillin and 50 $\lambda$.g/ml streptomycin.

When an apparatus used to collect saliva products includes a blotting means, that blotting means should be moistened either prior to or following placement of the blotting means into the chamber. Preferred moistening solutions include, but are not limited to, water, phosphate buffered saline, phosphate buffer, tris buffer, HEPES buffer, TEA buffer and TES buffer. More preferred moistening solutions include water and 50 U/ml penicillin and 50 $\mu$g/ml streptomycin. According to the present invention, a blotting means is sufficiently moistened to produce humidity in a chamber but not to drip liquid from which ectoparasites retained in the apparatus can drink. In a preferred embodiment, a blotting means which is about 4.0 cm in diameter and about 2.5 mm thick is moistened with about 2.3 milliliters (ml) of moistening solution.

In one embodiment, a pre-determined number of ectoparasites are introduced into the housing of an apparatus of the present invention. The number of ectoparasites to be introduced into a housing can vary with the size of the housing and should be a number that will not hinder the ability of an ectoparasite to deposit saliva on a collection means of the present invention.

In a preferred embodiment of the present invention, fleas are added to an apparatus of the present invention. Suitable and preferred numbers of fleas to introduce into a housing are heretofore disclosed. In particular, fleas newly emerged from the pupal stage are used. Such fleas can be raised as described in Wade et al., pp 186–190, 1988, *J.Med Entomol.*, vol 25. Preferably, such fleas have not had a blood meal. Fleas can be loaded into an apparatus by placing the fleas in an aquarium and aspirating them into the housing under vacuum. Additional optional components suitable for the maintenance of fleas can be added to the container, such as animal hair, and dry tissue.

In a preferred embodiment, at least one apparatus of the present invention having fleas contained in the housing of the apparatus is attached to an artificial feeding system such as disclosed herein. The apparatus can remain attached to the feeding system as long as fleas continue to release saliva while penetrating a collection means. Preferably, fleas are maintained in the apparatus attached to the feeding system from about 12 hours to about 120 hours, more preferably from about 24 hours to about 96 hours, and even more preferably for about 72 hours since fleas essentially stop secreting saliva by about that time. In accordance with the method of the present invention, preferably at least about 80 micrograms ($\mu$g), more preferably at least about 90 $\mu$g and even more preferably at least about 200 $\mu$g, of flea saliva protein can be collected from about $10^6$ flea-hour when measured using a Bio-Rad Bradford assay (available from Bio-Rad, Hercules, Calif.).

According to the present invention, ectoparasite saliva products can be extracted using a solvent capable of extracting saliva products from a collection means of the present invention, preferably in a form such that the functional activities of the eluted products are maintained. If functional activity of flea saliva proteins, for example is not maintained, it is within the scope of the invention to refold proteins to regain functionality using techniques known to those of skill in the art. Suitable extraction solvents include, but are not limited to, phosphate buffered saline, TFA in acetonitrile, chaotropic agents, detergents, organics, salts or combinations thereof. Preferred extraction solvents include phosphate buffered saline, acetonitrile and TFA in acetonitrile. More preferred extraction solvents include 0.1% TFA in 50% acetonitrile, 1% TFA in 50% acetonitrile, 12.8% acetonitrile and 50% acetonitrile. Suitable extraction times for eluting proteins and other products from a collection means are described in detail in the Examples.

Further purifications of saliva proteins extracted from a collection means of the present invention can be performed by fractionating the extracted product-containing solution to obtain separated peak fractions and recovering at least one of the peak fractions substantially free of the remaining fractions to obtain a formulation of ectoparasite saliva proteins. In a preferred embodiment, proteins contained in extracted saliva products of the present invention are further resolved by submitting the extract to HPLC purification to obtain peak fractions. In a particularly preferred embodiment, extracted saliva proteins of the present invention are further resolved by HPLC to obtain the peak fractions shown in FIG. 2. Details regarding the extraction and resolution of such proteins are presented in the Examples.

According to the present invention, a formulation comprising at least one ectoparasite saliva product of the present invention or a mimetope thereof, can be used to identify animals that are susceptible to or have allergic dermatitis.

In accordance with the present invention, a "mimetope" refers to any compound that is able to mimic the ability of an isolated ectoparasite saliva product of the present invention to carry out its function (e.g., anti-coagulation, anti-complement, vasodialators, proteases, or detecting and/or treating the hypersensitivity of an animal susceptible to or having allergic dermatitis). A mimetope can be a peptide that has been modified to decrease its susceptibility to degradation but that still retains the desired activity. Other examples of mimetopes include, but are not limited to, carbohydrate-based compounds, lipid-based compounds, nucleic acid-based compounds, natural organic compounds, synthetically derived organic compounds, anti-idiotypic antibodies and/or catalytic antibodies, or fragments thereof. Mimetopes of the present invention can also include non-proteinaceous portions of ectoparasite saliva products having allergenic and/or antigenic activity (e.g., carbohydrate moieties associated with ectoparasite saliva proteins). A mimetope can be obtained by, for example, screening libraries of synthetic compounds for compounds capable of altering the ability of ectoparasites to feed, or of detecting and/or treating allergic dermatitis resulting from the bites of ectoparasites. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

One embodiment of the present invention is an in vivo test that is capable of detecting whether an animal is hypersensitive to ectoparasite saliva products. An in vivo test of the present invention can initially be used to determine if an animal is hypersensitive to ectoparasite saliva products and then used to determine if an animal is hypersensitive to a particular ectoparasite saliva component, in particular to an ectoparasite saliva protein. An in vivo hypersensitivity test of the present invention is particularly useful for identifying animals susceptible to or having allergic dermatitis. An in vivo hypersensitivity test of the present invention is even more useful for identifying animals susceptible to or having FAD. A suitable in vivo hypersensitivity test of the present invention can be, but is not limited to, a skin test comprising administering (e.g., intradermally injecting or superficial scratching) an effective amount of a formulation containing at least one ectoparasite saliva product, or a mimetope thereof. Methods to conduct skin tests of the present invention are known to those of skill in the art and are briefly disclosed herein.

Suitable formulations to use in an in vivo skin test include ectoparasite saliva components (i.e., saliva products collected on, and remaining absorbed to, a collection means of the present invention, ectoparasite saliva extracts, and one or more isolated ectoparasite saliva proteins). A preferred formulation includes extracts and one or more isolated proteins.

A suitable amount of ectoparasite saliva product for use in a skin test of the present invention can vary widely depending on the allergenicity of the product used in the test and on the site at which the product is delivered. Suitable amounts of ectoparasite saliva products for use in a skin test of the present invention include an amount capable of forming reaction, such as a detectable wheal or induration (hardness) resulting from an allergic reaction to the product. Preferred amounts of ectoparasite saliva extracts or proteins for use in a skin test of the present invention range from about 1 nanogram (ng) to about 500 micrograms ($\mu$g), more preferably from about 5 ng to about 300 $\mu$g, and even more preferably from about 10 ng to about 50 $\mu$g of ectoparasite saliva extracts or proteins. It is to be appreciated by those of skill in the art that such amounts will vary depending upon the allergenicity of the extracts and/or protein(s) being administered.

According to the present invention, _ectoparasite saliva products of the present invention can be combined with an immunopotentiator (e.g., carriers or adjuvants of the present invention as defined in detail below). A novel aspect, however, of the present invention is that an ectoparasite saliva product of the present invention can induce a hypersensitive response in the absence of an immunopotentiator.

A skin test of the present invention further comprises administering a control solution to an animal. A control solution can include a negative control solution and/or a positive control solution. A positive control solution of the present invention contains an effective amount of at least one compound known to induce a hypersensitive response when administered to an animal. A preferred compound for use as positive control solution includes, but is not limited to, histamine. A negative control solution of the present invention can comprise a solution that is known not to induce a hypersensitive response when administered to an animal. As such, a negative control solution can comprise a solution having compounds essentially incapable of inducing a hypersensitive response or simply a buffer used to prepare the formulation, such as saline. An example of a preferred negative control solution is phenolated phosphate buffered saline (available from Greer Laboratories, Inc., Lenoir, N.C.).

Hypersensitivity of an animal to one or more formulations of the present invention can be evaluated by measuring reactions (e.g., wheal size, induration or hardness; using techniques known to those skilled in the art) resulting from administration of one or more experimental sample(s) and control sample(s) into an animal and comparing the reactions to the experimental sample(s) with reactions resulting from administration of one or more control solution. Preferred devices for intradermal injections include individual syringes. Preferred devices for scratching include devices that permit the administration of a number of samples at one time. The hypersensitivity of an animal can be evaluated by determining if the reaction resulting from administration of a formulation of the present invention is larger than the reaction resulting from administration of a negative control, and/or by determining if the reaction resulting from administration of the formulation is at least about the same size as the reaction resulting from administration of a positive control solution. As such, if an experimental sample produces a reaction greater than or equal to the size of a wheal produced by administration of a positive control sample to an animal, then that animal is hypersensitive to the experimental sample. Conversely, if an experimental sample produces a reaction similar to the reaction produced by administration of a negative control sample to an animal, then that animal is not hypersensitive to the experimental sample.

Preferred wheal sizes for evaluation of the hypersensitivity of an animal range from about 16 mm to about 8 mm, more preferably from about 15 mm to about 9 mm, and even more preferably from about 14 mm to about 10 mm in diameter.

Preferably, the ability or inability of an animal to exhibit an immediate hypersensitive response to a formulation of the present invention is determined by measuring wheal sizes from about 2 minutes to about 30 minutes after administration of a sample, more preferably from about 10 minutes to about 25 minutes after administration of a sample, and even more preferably about 15 minutes after administration of a sample.

Preferably, the ability or inability of an animal to exhibit a delayed hypersensitive response to a formulation of the present invention is determined by measuring induration and/or erythema from about 18 hours to about 30 hours after administration of a sample, more preferably from about 20 hours to about 28 hours after administration of a sample, and even more preferably at about 24 hours after administration of a sample. A delayed hypersensitivity response can also be measured using other techniques such as by determining, using techniques known to those of skill in the art, the extent of cell infiltrate at the site of administration during the time periods defined directly above.

In a preferred embodiment, a skin test of the present invention comprises intradermally injecting into an animal at a given site an effective amount of a formulation that includes flea saliva extracts (i.e., flea saliva products extracted from a collection means of the present invention) or at least one flea saliva protein of the present invention, and intradermally injecting an effective amount of a control solution into the same animal at a different site. It is within the scope of one of skill in the art to use devices capable of delivering multiple samples simultaneously at a number of sites, preferably enabling concurrent evaluation of numerous formulations. One preferred formulation comprises flea saliva products collected in accordance with the present invention. Also preferred are formulations comprising one or more recombinantly produced flea saliva proteins.

Suitable flea saliva products for use with a skin test of the present invention include FS-1 and/or FS-2 as well as at least a portion of at least one flea saliva product that can be isolated from FS-1 and/or FS-2. A preferred flea saliva product for use with a skin test includes FS-1, FS-2, and/or at least a portion of one or more of the proteins fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and fspN3, or homologues thereof. A more preferred flea saliva product for use with a skin test includes FS-1, FS-2, and/or at least a portion of one or more of the proteins fspE, fspF, fspG, fspH, fspI, fspJ1, fspJ2, fspK, fspL1, fspL2, fspM1, fspM2, fspN1, fspN2 and fspN3. Such formulations are shown in the Examples section as being able to induce FAD in dogs. A preferred positive control sample can be a sample comprising histamine. A preferred negative control sample can be a sample comprising diluent.

Animals suitable and preferred to test for hypersensitivity to ectoparasite saliva proteins using a skin test of the present invention are disclosed herein. Particularly preferred animals to test with a skin test of the present invention include dogs, cats and horses, with dogs and cats being even more preferred.

Another embodiment of the present invention is an in vitro immunoabsorbent test that is capable of detecting the presence of an antibody capable of binding to one or more ectoparasite saliva products of the present invention by contacting a putative antibody-containing solution with a solution containing ectoparasite saliva products in such a manner that immunocomplexes can form and be detected. Thus, an in vitro immunoabsorbent test of the present invention is particularly useful for identifying animals susceptible to or having allergic dermatitis by demonstrating that an animal has been previously exposed to an ectoparasite saliva antigen and, therefore may be hypersensitive to further exposure to an ectoparasite saliva antigen.

According to the present invention, an in vitro hypersensitivity test of the present invention can be, but is not limited to, an immunoabsorbent test comprising: (a) contacting a formulation of the present invention with a body fluid from an animal under conditions sufficient for formation of an immunocomplex between the formulation and antibodies, if present, in the body fluid; and (b) determining the amount of immunocomplex formed, wherein formation of the immunocomplex indicates that the animal is susceptible to or has allergic dermatitis. The immunoabsorbent test is particularly useful for the detection of IgE antibodies in the body fluid, thereby indicating immediate hypersensitivity in the animal. Determining the amount of immunocomplex formed can include the step of separating depending on the mode of detection. Immunoabsorbent assays can be a variety of protocols and can be set-up by those of skill in the art.

A preferred immunoabsorbent test of the present invention comprises a first step of coating one or more portions of a solid substrate with a suitable amount of one or more ectoparasite saliva products of the present invention or a mimetope thereof, and of coating one or more other portions of the (or another) solid substrate with a suitable amount of positive and/or negative control solutions of the present invention. A preferred solid substrate of the present invention can include, but is not limited to, an ELISA plate, a dipstick, a radioimmunoassay plate, agarose beads, plastic beads, immunoblot membranes and paper; a more preferred solid substrate includes an ELISA plate, a dipstick or a radioimmunoassay plate, with an ELISA plate and a dipstick being even more preferred. As used herein, a dipstick refers to any solid material having a surface to which antibodies can be bound, such solid material having a stick-like shape capable if being inserted into a test tube. Suitable and preferred flea saliva products for use with an in vitro hypersensitivity test of the present invention are as disclosed for a skin test of the present invention.

A second step of a preferred in vitro hypersensitivity test of the present invention comprises contacting the coated substrate with a body fluid, such as serum, plasma or whole blood, from an animal susceptible to allergic dermatitis in such a manner as to allow antibodies contained in the body fluid that are capable of binding to ectoparasite saliva products to bind to such products bound to the substrate to form immunocomplexes. Excess body fluid and antibodies are then washed from the substrate.

A third step of a preferred in vitro hypersensitivity test of the present invention comprises contacting the immunocomplexes bound to the substrate with a compound capable of binding to the immunocomplexes, such as a secondary antibody or other compound that is capable of binding to the heavy chain of allergy-related antibodies produced by animals allergic to ectoparasites, in such a manner that the compound(s) can bind to the immunocomplexes. Preferred binding compounds include, but are not limited to, secondary antibodies capable of binding to the heavy chain of IgE antibodies. Preferred animals to test are disclosed herein. Compounds capable of binding to immunocomplexes are usually tagged with a label which enables the amount of compound bound to the antibody from the body fluid to be measured. Such labels include, but are not limited to, a radioactive label, an enzyme capable of producing a color reaction upon contact with a substrate, a fluorescent label, a chemiluminescent label, a chromophoric label or a compound capable of being bound by another compound. Preferred labels include, but are not limited to, fluorescein, radioisotopes, alkaline phosphatases, biotin, avidin, or peroxidases.

A fourth step of a preferred in vitro hypersensitivity test of the present invention comprises measuring the amount of detectable label bound to the solid substrate using techniques known to those of skill in the art. It is within the scope of the present invention that the amount of antibody from the body fluid bound to the substrate can be determined using one or more layers of secondary antibodies or other binding compounds. For example, an untagged secondary antibody can be bound to a serum antibody and the untagged secondary antibody can then be bound by a tagged tertiary antibody.

A hypersensitive animal is identified by comparing the level of immunocomplex formation using samples of body fluid with the level of immunocomplex formation using control samples. An immunocomplex refers to a complex comprising an antibody and its ligand (i.e., antigen). As such, immunocomplexes form using positive control samples and do not form using negative control samples. As such, if a body fluid sample results in immunocomplex formation greater than or equal to immunocomplex formation using a positive control sample, then the animal from which the fluid was taken is hypersensitive to the ectoparasite saliva product bound to the substrate. Conversely, if a body fluid sample results in immunocomplex formation similar to immunocomplex formation using a negative control sample, then the animal from which the fluid was taken is not hypersensitive to the ectoparasite saliva product bound to the substrate.

One embodiment of the present invention is a kit useful for identification of an animal susceptible to or having allergic dermatitis. As used herein, a suspect animal is an animal to be tested. A kit of the present invention comprises a formulation of the present invention and a means for determining if an animal is susceptible to or has allergic dermatitis, in which the formulation is used to identify animals susceptible to or having allergic dermatitis. A means for determining if an animal is susceptible to or has allergic dermatitis can include an in vivo or in vitro hypersensitivity test of the present invention as described in detail above. A kit of the present invention further comprises at least one control solution such as those disclosed herein.

A preferred kit of the present invention comprises the elements useful for performing an immunoassay. A kit of the present invention can comprise one or more experimental samples (i.e., formulations of the present invention) and one or more control samples bound to at least one pre-packed dipstick, and the necessary means for detecting immunocomplex formation (e.g., labelled secondary antibodies or other binding compounds and any necessary solutions needed to resolve such labels, as described in detail above) between antibodies contained in the bodily fluid of the animal being tested and the proteins bound to the dipstick. It is within the scope of the invention that the kit can comprise simply a formulation of the present invention and that the detecting means can be provided in another way.

An alternative preferred kit of the present invention comprises elements useful for performing a skin test. A kit of the present invention can comprise at least one pre-packed syringe and needle apparatus containing one or more experimental samples and/or one or more control samples.

It is within the scope of the present invention that two or more different in vivo and/or in vitro tests can be used in combination for diagnostic purposes. For example, the immediate hypersensitivity of an animal to an ectoparasite saliva allergen can be tested using an in vitro immunoabsorbent test capable of detecting IgE antibodies specific for an ectoparasite saliva allergen in the animal's bodily fluid. While most animals that display delayed hypersensitivity to an ectoparasite saliva allergen also display immediate hypersensitivity to the allergen, a small number of animals that display delayed hypersensitivity to an allergen do not display immediate hypersensitivity to the allergen. In such cases, following negative results from the IgE-specific in vitro test, the delayed hypersensitivity of the animal to an ectoparasite saliva allergen can be tested using an in vivo test of the present invention.

Another aspect of the present invention includes treating animals susceptible to or having allergic dermatitis, with a formulation of the present invention. According to the present invention, the term treatment can refer to the regulation of a hypersensitive response by an animal to bites from ectoparasites. Regulation can include, for example, immunomodulation of cells involved in the animal's hypersensitive response or alteration of the ability of an ectoparasite to introduce allergens into an animal, for example by inhibiting the anti-coagulation activity of a saliva enzyme, thereby impairing the ability of the arthropod to penetrate the dermis of an animal and feed. Immunomodulation can include modulating the activity of molecules typically involved in an immune response (e.g., antibodies, antigens, major histocompatibility molecules (MHC) and molecules co-reactive with MHC molecules). In particular, immunomodulation refers to modulation of antigen:antibody interactions resulting in inflammatory responses, immunosuppression, and immunotolerization of cells involved in a hypersensitive response. Immunosuppression refers to inhibiting an immune response by, for example, killing particular cells involved in the immune response. Immunotolerization refers to inhibiting an immune response by anergizing (i.e., diminishing reactivity of a T cell to an antigen) particular cells involved in the immune response. Suitable and preferred ectoparasites against which to treat an animal are disclosed herein. A particularly preferred formulation of the present invention is used to treat FAD.

One embodiment of the present invention is a therapeutic composition that, when administered to an animal in an effective manner, is useful for immunomodulating the immune response of the animal (i.e., immunomodulating the animal) so as to block (i.e., to inhibit, reduce or substantially prevent) a hypersensitive response by the animal upon subsequent exposure to allergenic components transmitted through bites from ectoparasites. Such a therapeutic composition is useful for immunomodulating animals known to be hypersensitive to ectoparasite saliva products and animals susceptible to hypersensitive responses against ectoparasite saliva products.

One embodiment of the present invention is a therapeutic composition that includes de-sensitizing compounds capable of inhibiting an immune response to an ectoparasite saliva product of the present invention. Such de-sensitizing compounds include blocking compounds, toleragens and/or suppressor compounds. Blocking compounds comprise compounds capable of modulating antigen:antibody interactions that can result in inflammatory responses, toleragens are compounds capable of immunotolerizing an animal, and suppressor compounds are capable of immunosuppressing an animal. A de-sensitizing compound of the present invention can be soluble or membrane-bound. Membrane-bound de-sensitizing compounds can be associated with biomembranes, including cells, liposomes, planar membranes or micelles. A soluble de-sensitizing compound of the present invention is useful for: (1) inhibiting a Type I hypersensitivity reaction by blocking IgE:antigen mediated de-granulation of mast cells; (2) inhibiting a Type III hypersensitivity reaction by blocking IgG:antigen complex formation leading to complement destruction of cells; and (3) inhibiting a Type IV hypersensitivity reaction by blocking T helper cell stimulation of cytokine secretion by macrophages. A membrane-bound de-sensitizing compound of the present invention is useful for: (1) inhibiting a Type II hypersensitivity reaction by blocking IgG:antigen complex formation on the surface of cells leading to complement destruction of cells; (2) inhibiting a Type II hypersensitivity reaction by blocking IgG regulated signal transduction in immune cells; and (3) inhibiting a Type IV hypersensitivity reaction by blocking T cytotoxic cell killing of antigen-bearing cells.

A de-sensitizing compound of the present invention can also be covalently linked to a ligand molecule capable of targeting the de-sensitizing compound to a specific cell involved in a hypersensitive response to ectoparasite saliva products. Appropriate ligands with which to link a de-sensitizing compound include, for example, at least a portion of an immunoglobulin molecule, cytokines, lectins, heterologous allergens, CD8 molecules or major histocompatibility molecules (e.g., MHC class I or MHC class II molecules). Preferred portions of immunoglobulin molecules to link to a de-sensitizing compound include variable regions capable of binding to immune cell specific surface molecules and constant regions capable of binding to Fc receptors on immune cells, in particular IgE constant regions. Preferred CD8 molecules include at least the extracellular functional domains of the a chain of CD8. An immune cell refers to a cell involved in an immune response, in particular, cells having MHC class I or MHC class II molecules. Preferred immune cells include antigen presenting cells, T cells and B cells.

In one embodiment, a therapeutic composition of the present invention includes ectoparasite saliva products of the present invention, or mimetopes thereof. Preferred therapeutic compositions include formulations comprising ectoparasite saliva extracts or at least one ectoparasite saliva product (preferably protein) of the present invention or mimetopes thereof.

Suitable therapeutic compositions of the present invention for treating flea allergy dermatitis include flea saliva extracts and other formulations including at least one flea saliva product, preferably a protein, or a mimetope thereof. Preferred therapeutic compositions include FS-1 and/or FS-2 as well as at least a portion of at least one flea saliva product that can be isolated from FS-1 and/or FS-2. As such, preferred formulations for use as therapeutic compositions include FS-1, FS-2, and/or at least a portion of one or more of the proteins fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and fspN3, or homologues thereof. A more preferred flea saliva extract for use as a therapeutic compositions includes FS-1, FS-2, and/or at least a portion of one or more of the proteins fspE, fspF, fspG, fspH, fspI, fspJ1, fspJ2, fspK, fspL1, fspL2, fspM1, fspM2, fspN1, fspN2 and fspN3.

In another embodiment, a therapeutic composition can include ectoparasite products of the present invention associated with a suitable excipient. A therapeutic composition of the present invention can be formulated in an excipient that the animal to be treated can tolerate. Preferred excipients are capable of maintaining a product of the present invention in a form that is capable of being bound by cells involved in an allergic response in an animal such that the cells are stimulated to initiate or enhance an immune response. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In another embodiment, a therapeutic composition of the present invention can also comprise a carrier or adjuvant, although it is to be appreciated that an advantage of saliva products of the present invention is that adjuvants and/or carriers are not required for administration. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark).

Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a therapeutic composition of the present invention into the bloodstream of an animal. Suitable controlled release formulations include, but are not limited to, biocompatible (including biodegradable) polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ.

The present invention also includes a recombinant virus particle therapeutic composition. Such a composition includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. Preferred recombinant particle viruses are those based on alphaviruses (such as Sindbis virus), herpesviruses and poxviruses. Methods to produce and use recombinant virus particle vaccines are disclosed in U.S. patent application Ser. No. 08/015/414, filed Feb. 8, 1993, entitled "Recombinant Virus Particle Vaccines", which is incorporated by reference herein in its entirety.

When administered to an animal, a recombinant virus particle therapeutic composition of the present invention infects cells within the immunized animal and directs the production of a protective protein or RNA nucleic acid molecule that is capable of protecting the animal from allergic dermatitis caused by the bites of ectoparasites. For example, a recombinant virus particle comprising a nucleic acid molecule encoding one or more ectoparasite saliva protein of the present invention is administered according to a protocol that results in the tolerization of an animal against ectoparasite saliva allergens.

Therapeutic compositions of the present invention can be sterilized by conventional methods which do not result in protein degradation (e.g., filtration) and/or lyophilized.

A therapeutic composition of the present invention can be administered to any animal susceptible to ectoparasite infestation as herein described. Acceptable protocols by which to administer therapeutic compositions of the present invention in an effective manner can vary according to individual dose size, number of doses, frequency of dose administration, and mode of administration. Determination of such protocols can be accomplished by those skilled in the art. An effective dose refers to a dose capable of treating an animal against hypersensitivity to ectoparasite saliva allergens. Effective doses can vary depending upon, for example, the therapeutic composition used, the arthropod from which the composition was derived, and the size and type of the recipient animal. Effective doses to immunomodulate an animal against ectoparasite saliva allergens include doses administered over time that are capable of alleviating a hypersensitive response by an animal to ectoparasite saliva allergens. For example, a first tolerizing dose can comprise an amount of a therapeutic composition of the present invention that causes a minimal hypersensitive response when administered to a hypersensitive animal. A second tolerizing dose can comprise a greater amount of the same therapeutic composition than the first dose. Effective tolerizing doses can comprise increasing concentrations of the therapeutic composition necessary to tolerize an animal such that the animal does not have a hypersensitive response to the bite of an ectoparasite. An effective dose to desensitize an animal can comprise a concentration of a therapeutic composition of the present invention sufficient to block an animal from having a hypersensitive response to the bite of an ectoparasite. Effective desensitizing doses can include repeated doses having concentrations of a therapeutic composition that cause a minimal hypersensitive response when administered to a hypersensitive animal.

A suitable single dose is a dose that is capable of treating an animal against hypersensitivity to ectoparasite saliva allergens when administered one or more times over a suitable time period. For example, a preferred single dose of an ectoparasite saliva product, or mimetope therapeutic composition is from about 0.5 ng to about 1 g of the therapeutic composition per kilogram body weight of the animal. Further treatments with the therapeutic composition can be administered from about 1 hour to 1 year after the original administration. Further treatments with the therapeutic composition preferably are administered when the animal is no longer protected from hypersensitive responses to ectoparasite. Particular administration doses and schedules can be developed by one of skill in the art based upon the parameters discussed above. Modes of administration can include, but are not limited to, subcutaneous, intradermal, intravenous, nasal, oral, transdermal and intramuscular routes.

A therapeutic composition of the present invention can be used in conjunction with other compounds capable of modifying an animal's hypersensitivity to ectoparasite bites. For example, an animal can be treated with compounds capable of modifying the function of a cell involved in a hypersensitive response, compounds that reduce allergic reactions, such as by systemic agents or anti-inflammatory agents (e.g., anti-histamines, anti-steroid reagents, anti-inflammatory reagents and reagents that drive immunoglobulin heavy chain class switching from IgE to IgG). Suitable compounds useful for modifying the function of a cell involved in a hypersensitive response include, but are not limited to, antihistamines, cromolyn sodium, theophylline, cyclosporin A, adrenalin, cortisone, compounds capable of regulating cellular signal transduction, compounds capable of regulating adenosine 3',5'-cyclic phosphate (cAMP) activity, and compounds that block IgE activity, such as peptides from IgE or IgE specific Fc receptors, antibodies specific for peptides from IgE or IgE-specific Fc receptors, or antibodies capable of blocking binding of IgE to Fc receptors.

Another aspect of the present invention includes a method for prescribing treatment for animals susceptible to or having allergic dermatitis, using a formulation of the present invention. A preferred method for prescribing treatment for flea allergy dermatitis, for example, comprises: (1) intradermally injecting into an animal at one site an effective amount of a formulation containing at least one flea saliva antigen of the present invention, or a mimetope thereof (suitable and preferred formulations are disclosed herein); (2) intradermally injecting into the animal at a second site an effective amount of a control solution; (3) evaluating if the animal has flea allergy dermatitis by measuring and comparing the wheal size resulting from injection of the formulation with the wheal size resulting from injection of the control solution; and (4) prescribing a treatment for the flea allergy dermatitis.

An alternative preferred method for prescribing treatment for flea allergy dermatitis comprises: (1) contacting a first portion of a sample of bodily fluid obtained from an animal to be tested with an effective amount of a formulation containing at least one flea saliva antigen, or a mimetope thereof (suitable and preferred formulations are disclosed herein) to form a first immunocomplex solution; (2) contacting a positive control antibody to form a second immunocomplex solution; (3) evaluating if the animal has flea allergy dermatitis by measuring and comparing the amount of immunocomplex formation in the first and second immunocomplex solutions; and (4) prescribing a treatment for the flea allergy dermatitis. It is to be noted that similar methods can be used to prescribe treatment for allergies caused by other ectoparasites using ectoparasite saliva product formulations as disclosed herein.

Another aspect of the present invention includes a method for monitoring animals susceptible to or having allergic dermatitis, using a formulation of the present invention. In vivo and in vitro tests of the present invention can be used to test animals for allergic dermatitis prior to and following any treatment for allergic dermatitis. A preferred method to monitor treatment of flea allergy dermatitis (which can also be adapted to monitor treatment of other ectoparasite allergies) comprises: (1) intradermally injecting an animal at one site with an effective amount of a formulation containing at least one flea saliva product, or a mimetope thereof (suitable and preferred formulations are disclosed herein); (2) intradermally injecting an effective amount of a control solution into the animal at a second site; and (3) determining if the animal is desensitized to flea saliva antigens by measuring and comparing the wheal size resulting from injection of the formulation with the wheal size resulting from injection of the control solution.

An alternative preferred method to monitor treatment of flea allergy dermatitis (which can be adapted to monitor treatments of other ectoparasite allergies) comprises: (1) contacting a first portion of a sample of bodily fluid obtained from an animal to be tested with an effective amount of a formulation containing at least one flea saliva product or mimetope thereof (suitable and preferred formulations are disclosed herein) to form a first immunocomplex solution; (2) contacting a positive control antibody to form a second immunocomplex solution; and (3) determining if the animal is desensitized to flea saliva antigens by measuring and comparing the amount of immunocomplex formation in the first and second immunocomplex solutions.

The present invention also includes antibodies capable of selectively binding to an ectoparasite saliva product, or mimetope thereof. Such an antibody is herein referred to as an anti-ectoparasite saliva product antibody. As used herein, the term "selectively binds to" refers to the ability of such an antibody to preferentially bind to ectoparasite saliva products and mimetopes thereof. In particular, the present invention includes antibodies capable of selectively binding to flea saliva products. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferred antibodies are raised in response to ectoparasite saliva proteins, or mimetopes thereof. More preferred antibodies are raised in response to at least one ectoparasite saliva protein, or mimetope thereof, having at least a portion of an ectoparasite saliva protein eluted from a collection means of the present invention. Even more preferred antibodies are raised in response to at least one flea saliva product, or homologues thereof (e.g., saliva products of other ectoparasites), contained in the saliva extracts FS-1 or FS-2. More preferred ectoparasite saliva proteins against which to raise an antibody includes at least a portion of one or more of the proteins fspA, fspB, fspC1, fspC2, fspD1, fspD2, fspE, fspF, fspG, fspH, fspI, fspJ1, fspJ2, fspK, fspL1, fspL2, fspM1, fspM2, fspN1, fspN2 and fspN3, or homologues thereof. Preferably, an antibody of the present invention has a single site binding affinity of from about $10^3 M^{-1}$ to about $10^{12} M^{-1}$ for a flea saliva product of the present invention.

A preferred method to produce antibodies of the present invention includes administering to an animal an effective amount of an ectoparasite saliva product or mimetope thereof to produce the antibody and recovering the antibodies. Antibodies raised against defined products or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as vaccines to passively immunize an animal in order to protect the animal from allergic dermatitis, (b) as positive controls in test kits, and/or (c) as tools to recover desired ectoparasite saliva products from a mixture of proteins and other contaminants.

The following examples are provided for the purposes of illustration and are not intended to limit the scope of the present invention.

EXAMPLES

Example 1

This example describes the collection of flea saliva proteins using a saliva collection apparatus of the present invention.

A saliva collection apparatus was prepared as follows. Referring to FIG. 4A and 4B, a humidifying means (34)

comprising about 4 pieces of VWR blotting pads #320 (VWR, Denver, Colo.) was prepared that fit the inner diameter (about 47 mm in diameter) of a chamber (6) of a saliva collection apparatus (2). The blotting pads were pre-wetted using a sufficient amount of pre-wetting solution (sterile water containing 50 units/ml penicillin and 50 μ/ml streptomycin, available from Sigma, St. Louis, Mo.) such that the blotting pads were damp but not dripping wet. The pre-wetted filters (34) were placed inside the bottom end (22) of the chamber (6) of the saliva collection apparatus (2) such that the filter paper sat immediately inside the bottom end (22) of the chamber (6).

A collection means (24) comprising a Durapore™ membrane (available from Millipore, Bedford, Mass.) was cut to fit the outer diameter (about 48 mm in diameter) of the chamber (6) of the saliva collection apparatus (2). The Durapore™ membrane was pre-wetted using the pre-wetting solution described above. The Durapore™ membrane (24) was placed immediately outside the bottom end (22) of the chamber (6) such that the Durapore™ membrane (24) contacted the outer rim of the bottom end (22) of the chamber (6) and also contacted the damp filter paper. A barrier means comprising a piece of stretched Parafilm™ (28) (available from American National Can™, Greenwich, Conn.) was stretched over the collection means (24) and bottom end (22) of the chamber (6) and up the outer wall (30) of the chamber (6). A rubber seal (32) (i.e., an O-ring) was placed over the Parafilm™ (28) thereby further securing the Parafilm™ (28) across the collection means (24) and to the outer wall (30) and to seal in the chamber (6) environment.

The collection apparatus (2) was preassembled and then the top end (20) of the chamber (6) was attached to an artificial feeding system capable of acting as a source of heat and humidity such as that described by Wade et al., (ibid.). The artificial feeding system comprised a large plexiglass box (40 cm×40 cm×40 cm) divided horizontally into an upper compartment and a lower compartment by a plexiglass shelf having holes drilled through. A collection apparatus (2) was inserted into a hole such that the chamber (6) of the apparatus (2) was located above the shelf in the upper compartment and the housing (4) was located below the shelf in the lower compartment. The apparatus (2) was secured to the shelf by attaching a rubber band attached to metal hooks placed in the shelf. Any open holes in the shelf were closed off using rubber stoppers to isolate the environment within the upper compartment from the environment within the lower compartment. The upper compartment contained two trays of water, a fan and a heating block. The trays of water were placed such that the fan faced the trays. While the apparatus (2) was maintained in the artificial feeding system, the fan was blown continuously thereby circulating heat and humidity throughout the upper compartment and the chamber (6) of the collection apparatus (2). As such, the relative humidity within the chamber (6) was maintained at about 94% humidity and the temperature was maintained at about 37° C.

About 3,000 to 5,000 newly emerged unfed Ctenocephalides felis fleas were added to the housing (4) of the collection apparatus (2). The fleas were first collected in a 20 gallon glass aquarium. The fleas were then transferred to the housing (4) of a collection apparatus (2) by placing the end of the housing (4) having the nylon mesh of the exchange means (16) on top of a vacuum chamber and aspirating the fleas from the aquarium into the housing (4) through a tygon tubing. The housing (4) was then covered with the nylon mesh of the retaining means (18) to secure the fleas within the housing (4). The bottom end (22) of the chamber (6) was then placed on the housing (4) such that the Parafilm™ (28) and the nylon mesh of the retaining means (18) were juxtaposed. When the collection apparatus (2) was attached to the artificial feeding system, the ambient temperature within the housing (4) was maintained at about 27° C. while the ambient temperature of the chamber (6) was maintained at about 37° C. The relative humidity of the housing (4) was maintained at about 50% by closing the lower compartment with the plexiglass shelving.

In one experiment, flea saliva products were collected on a Durapore™ membrane (24) and visualized by immersing the membrane in 0.1% Coomassie blue stain for 20 minutes, destaining the membrane in 50% methanol and air drying the membrane. Proteins deposited on the membrane were detected by their blue color.

In another experiment, flea saliva products were collected for 0 through 24 hours, 24 through 72 hours, and 72 through 120 hours after loading fleas into the collection apparatus. At 24 hours, 72 hours and 120 hours, the Durapore™ membrane (24) attached to the collection apparatus (2) was removed and a new pre-wetted Durapore™ membrane (24) was attached to the same apparatus. The blotting pads were re-wetted using the pre-wetting solution described above when the new Durapore™ membrane (24) was replaced. Flea saliva products were extracted from the Durapore™ membrane (24) by soaking each membrane from each time point separately in a solvent comprising 50% acetonitrile with 1% TFA overnight at room temperature with stirring to obtain a flea saliva product mixture comprising flea saliva products that had eluted into the solvent. The mixture containing the flea saliva products was recovered and lyophilized until dry to form a pellet. The amount and characteristics of flea saliva proteins eluted from each Durapore™ membrane from each time point was determined by reducing 14% Tris-glycine SDS-PAGE using techniques similar to those described by Sambrook et al., ibid. The resultant protein pattern was visualized by staining the gel with Coomassie blue stain using techniques as described above. The amount of saliva proteins collected on the membranes decreased when the fleas had been in the collection apparatus for more than 72 hours.

Example 2

Standard procedures to collect FS-1 and FS-2 flea saliva extracts of the present invention were performed as follows. Flea saliva products were collected for 72 hours on collection membranes using the method described in Example 1. Flea saliva products were extracted from the Durapore™ membrane (24) by soaking each membrane from each time point separately in a first solvent comprising 50% acetonitrile with 0.1% TFA for 8 hours. The first mixture containing the eluted flea saliva products was recovered and lyophilized until dry, thereby forming a first pellet. The same membranes were then soaked in a second solvent comprising 50% acetonitrile with 1% TFA overnight at room temperature with stirring to obtain a flea saliva product mixture comprising flea saliva products that had eluted into the second solvent. The second mixture was recovered from this second extraction and lyophilized until dry to form a second pellet.

The two pellets recovered from the two lyophilization steps were mixed with a third solvent comprising 12.8% acetonitrile and flea saliva products solubilized in the solvent were recovered. The non-solubilized material was mixed again with 12.8% acetonitrile and additional flea saliva products solubilized in the solvent were recovered. The two mixtures were combined to obtain the extract FS-1.

The non-solubilized material remaining after the second solubilization step was then mixed with 50% acetonitrile which solubilized the remaining material to obtain the extract FS-2.

The amount and characteristics of flea saliva proteins contained in the FS-1 and FS-2 flea saliva extracts obtained in at least one experiment were determined according to the following method. Each extract was concentrated by evaporation under vacuum and evaluated by reducing 16% Trisglycine SDS-PAGE using techniques similar to those described by Sambrook et al., ibid. Using such standard procedures, about 10 μg of FS-1 or FS-2 eluted from the Durapore™ membrane was loaded onto a 16% Tris-glycine polyacrylamide gel and submitted to electrophoresis under reducing conditions. The gel was stained with Coomassie blue and dried.

The results are shown in FIG. 1B. FS-1 is shown in lane 13 of FIG. 1B and FS-2 is shown in lanes 14 and 15 of FIG. 1B. FS-1 was found to contain proteins estimated to have the following molecular weights: 9 kD, 11 kD, 12 kD, 15 kD, 22 kD, 48 kD, 50 kD, 53 kD, 80 kD, 124 kD, 130 kD, 189 kD and 201 kD. Those proteins of 80 kD and above were much fainter than the lower molecular weight bands. FS-2 was found to contain proteins having the following molecular weights: 47 kD, 49 kD, 52 kD, 57 kD, 64 kD, 71 kD, 88 kD, 96 kD, 96 kD, 130 kD, 161 kD, 175 kD, 189 kD, 222 kD, 235 kD and 302 kD. The bands at 47 kD, 49 kD and 52 kD were more prominent than the bands having higher molecular weights. The results suggest that a substantial portion of the protein contained in FS-2 is fspN1, fspN2 and/or fspN3.

Protein concentrations were measured using a Bio-Rad Bradford assay (available from Bio-Rad, Hercules, Calif.). The results indicate that about 750 μg of protein can be collected in about $3.66 \times 10^7$ flea hours ($5.08 \times 10^5$ fleas for 72 hours) in an FS-1 extract and about 2.35 mg of protein can be collected in about $3.66 \times 10^7$ flea hours in an FS-2 extract.

Example 3

This example describes the characterization by HPLC of flea saliva proteins collected using a saliva collection apparatus of the present invention.

An FS-1 flea saliva extract was collected as described in Example 2 from about 140,000 fleas for 72 hours. Proteins contained in FS-1 were resolved using standard procedures of high pressure liquid chromatography (HPLC). Specifically, the proteins were passed over a 15 cm×0.46 cm C4 column using a gradient from 0.1% TFA in water (Solvent A) to 0.085% TFA in 90% $CH_3CN$ (Solvent B) at a flow rate of 0.8 ml per minute. Thus, the gradient was about 5.6% Solvent B at 15 minutes and about 100% Solvent B at 75 minutes.

The results are shown in FIG. 2. About 14 major protein fractions were resolved. The recovery for each peak was about 5 μg to 10 μg of protein per peak. The peaks were labelled peak A, peak B, peak C, peak D, peak E, peak F, peak G, peak H, peak I, peak J, peak K, peak L, peak M and peak N, as shown in FIG. 2, and represent, respectively, protein formulations fspA, fspB, fspC1 and fspC2, fspD1 and fspD2, fspE, fspF, fspG, fspH, fspI, fspJ1 and fspJ2, fspK, fspL1 and fspL2, fspM1 and fspM2, and fspN1, fspN2 and fspN3.

Figure 1C:
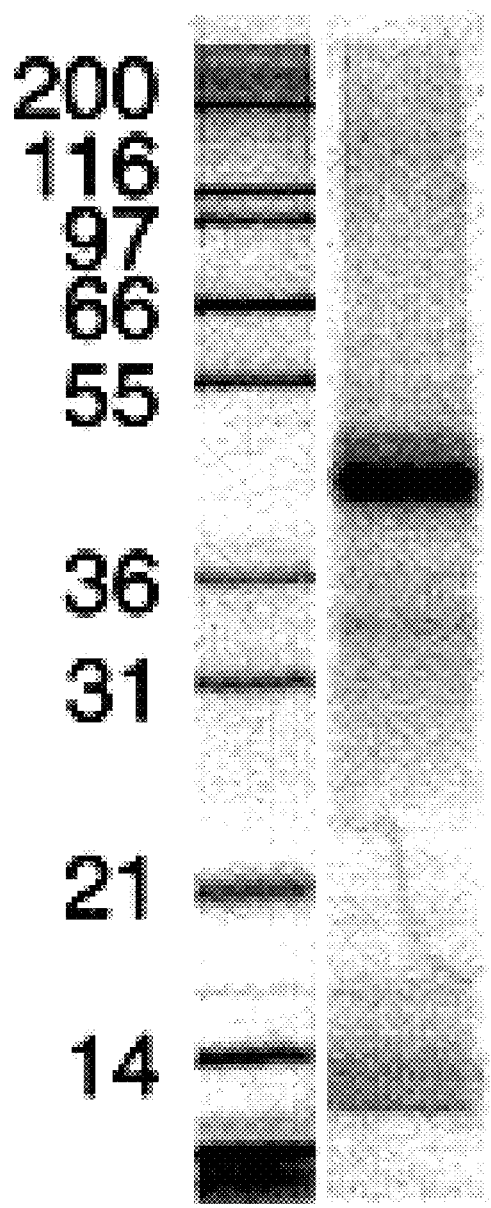
FIG. 1C illustrates the resolution of fspN by reducing 16% Tris glycine SDS-PAGE.

Samples from each HPLC peak were resolved by Tris Glycine SDS-PAGE gels using the method described in Example 1. The results are shown in FIGS. 1A, 1B and 1C. The proteins shown in FIGS. 1A and 1B were resolved on 16% Tris Glycine SDS-PAGE gels and the proteins shown in FIG. 1C were resolved on a 14% Tris Glycine SDS-PAGE gel. Protein markers are shown in lane 1 of FIG. 1A, lane 2 of FIG. 1B and lane 1 of FIG. 1C. The additional lanes show saliva formulation samples as follows:

| Lane | Fractions(s) | Fs-() |
|---|---|---|
| FIG. 1A | | |
| 1) | — | Mol. Wt. Std. |
| 2) | 10 | — |
| 3) | 11–13 | A |
| 4) | 14 | B |
| 5) | 15 | B |
| 6) | 16 | C1 |
| 7) | 17 | C2 |
| 8) | 18 | D1 |
| 9) | 19 | D1 |
| 10) | 20 | D2 |
| 11) | 21 | D2 |
| 12) | 22 | E |
| 13) | 23 | F |
| 14) | 24 | G |
| 15) | 25 | G |
| FIG. 1B | | |
| 1) | 26–27 | G |
| 2) | — | Mol. Wt. Std. |
| 3) | 28 | H |
| 4) | 29–30 | I |
| 5) | 31 | J |
| 6) | 32 | K |
| 7) | 33 | K |
| 8) | 34 | L |
| 9) | 35 | M1 |
| 10) | 36–37 | M1 |
| 11) | 38 | M1 |
| 12) | 39–50 | M2 |
| 13) | — | FS–1 |
| 14) | — | FS–2 |
| 15) | — | FS–2 |
| FIG. 1C | | |
| 1) | — | Mol. Wt. Std. |
| 2) | 56–68 | N |

Referring to FIG. 1A, the following flea saliva proteins (referred to as bands) were observed: a prominent band of about 10 kD in peak A and peak B samples; a prominent band of about 6 kD and a less prominent band of 9 kD in a peak C sample referred to as C1; a prominent band of about 7 kD in a peak C sample referred to as C2; a prominent band of about 7 kD and a less prominent band of 8 kD in a peak D sample referred to as D1; a prominent band of about 8 kD and a less prominent band of 9 kD in a peak D sample referred to as D2; a prominent band of 8 kD and a less prominent band of about 7 kD in peaks E and F samples; and a prominent band of about 9 kD, and less prominent bands of about 7 kD and 10 kD in a peak G sample. Referring to FIG. 1B, the following flea saliva proteins were observed: a prominent band of about 9 kD and a less prominent band of about 12 kD in a peak H sample; a prominent band of about 21 kD, and less prominent bands of about 7 kD, 9 kD, 12 kD, 14 kD, and 70 kD in a peak I sample; prominent bands of about 14 kD and 21 kD, and less prominent bands of about 11 kD and 17 kD in a peak J sample; prominent bands of about 14 kD and 15 kD and less prominent bands of about 12 kD, 18 kD and 21 kD in a peak K sample; a prominent band of about 15 kD in a peak L sample; prominent bands of about 11 kD, 12 kD and 21 kD and less prominent bands of about 15 kD, 17 kD, 22 kD and 37 kD in a peak M sample referred to as M1; and a prominent band of about 36 kD and less prominent bands of about 11 kD, 21 kD and 22 kD in a peak M sample referred to as M2. Referring to FIG. 1C, prominent bands of about 42 kD, 43 kD and 44 kD and a less prominent band of about 32 kD were detected in a peak N sample.

Example 4

This example describes the amino acid sequence analysis of the isolated and HPLC purified flea saliva proteins.

Amino (N-) terminal amino acid sequencing analysis was performed on several of the HPLC-separated flea saliva proteins described in Example 3 using standard procedures known to those in the art (see, for example, Geisow et al., 1989, in Protein Sequencing: A Practical Approach, JBC Findlay and MJ Geisow (eds.), IRL Press, Oxford, England, pp. 85–98; Hewick et al., 1981, J. Biol. Chem., Vol. 256, pp. 7990–7997).

The N-terminal partial amino acid sequence of flea saliva protein fspA, which migrated as Peak A in FIG. 2, was determined to be

```
Y G K Q Y S E K G G R G Q R H Q I L K K G K
Q   Y S           S K       I     L   D   L
S
R
``` as represented in standard single letter code. This N-terminal partial amino acid sequence of fspA is denoted SEQ ID NO:1. It should be noted that there was heterogeneity in several positions which may represent sequence errors (i.e., misidentification of amino acids) or allelic variations in the flea population from which the saliva proteins were collected. There was an apparently equal likelihood of finding any one of the alternative amino acids at the indicated positions.

The N-terminal partial amino acid sequence of flea saliva protein fspH, which migrated as Peak H in FIG. 2, was determined to be D R R V S K T X Q S G G K I Q S E X Q V V I K S G Q H/Y I L E N Y X S D G R, denoted herein as SEQ ID NO:14. Histidine and tyrosine were equally likely at amino acid position 27.

Flea saliva protein fspH was also submitted to proteolytic cleavage in order to obtain internal amino acid sequence data. Specifically, fspH was cleaved with Endoproteinase Asp-N (available from Boehringer Mannheim Biochemica, Indianapolis, Ind.) using methods standard in the art. The digested protein was then resolved by HPLC using the method described by Stone et al. (ibid.). The resultant HPLC profile is shown in FIG. 3. Three proteolytic fragments were isolated, that are referred to herein as fspHe, fspHh and fspHj.

The N-terminal partial amino acid sequence of fspHe was determined to be D-S-K-H-C-Y-C-E-A-P-Y-S, also denoted SEQ ID NO:3. The N-terminal partial amino acid sequence of fspHh was determined to be D G R N N N N P C H L F C M R E C R S G N G G C G N G G R T R P D S K H C, also denoted SEQ ID NO:4. The N-terminal partial amino acid sequence of fspHj was determined to be D R R V S K T C Q S G, also denoted SEQ ID NO:5. Comparison of SEQ ID NO:5 to SEQ ID NO:14 indicated that fspHj was the N-terminal fragment of fspH.

By aligning SEQ ID NO:14, SEQ ID NO:3, SEQ ID NO:4 and SEQ ID NO:5, the following amino acid sequence was deduced, starting at the N-terminus of fspH: D R R V S K T C Q S G G K I Q S E X Q V V I K S G Q H/Y I L E N Y X S D G R N N N N P C H L F C M R E C R S G N G G C G N G G R T R P D S K H C Y C E A P Y S. This amino acid sequence is denoted SEQ ID NO:2 and is believed to represent most of fspH since the molecular weight of a protein having this sequence is about 8600 kD.

The N-terminal partial amino acid sequence of flea saliva protein fspI, which migrated as Peak I in FIG. 2, was determined to be E D I W K V N K K X T S G G K N Q D R K L D Q I I Q K G Q Q V X X Q N X X K, denoted herein as SEQ ID NO:6.

Sequence analysis of Peak J proteins indicated the presence of two proteins in that peak, referred to herein as fspjl and fspJ2. The N-terminal partial amino acid sequence of flea saliva protein fspJ1 was determined to be N S H E P G N T R K I R E V M D K L R K Q H P, denoted herein as SEQ ID NO:7. The N-terminal partial amino acid sequence of flea saliva protein fspJ2 was determined to be E I K R N S H E P G N T R K I R E V M D K L R K Q H P, denoted herein as SEQ ID NO:8. The proteins represented by SEQ ID NO:7 and SEQ ID NO:8 were not separately resolved by SDS-PAGE as described in Example 1. Comparison of SEQ ID NO:7 and SEQ ID NO:8 suggest that fspJ1 may be a truncated version of fspJ2, in that the N-terminal partial amino acid sequence of fspJ1 appears to be very similar to that of fspJ2 except that fspJ1 lacks the first 4 amino acids found at the N-terminus of fspJ2.

Sequence analysis of Peak L proteins indicated the presence of two proteins in that peak, referred to herein as fspL1 and fspLJ2. That there were two proteins, namely fspL1 and fspL2, was shown by submitting peak L to C4 reverse phase chromatography using 0.13% heptafluorobutyric acid (Solvent A) and 0.1% heptafluorobutyric acid in 90% acetonitrile (Solvent B) in the following gradient format: an 80 minute gradient from 30% Solvent B to 70% Solvent B. The N-terminal partial amino acid sequence of the HPLC-separated fspL1 was determined to be N D K E P G N T R K I R E V M D K L R K Q A Q P R T D G Q R P K T X I M, also denoted SEQ ID NO:9. The N-terminal partial amino acid sequence for fspL2 was determined to be X L X R N D K E P G N T R K I R E V M D K, also denoted SEQ ID NO:10. A comparison of SEQ ID NO:9 and SEQ ID NO:10 indicates that fspL1 and fspL2 are similar proteins, except that fspL1 is 4 amino acids shorter than fspL2 at the N-terminus.

Resolution of proteins contained in Peak N by SDS-PAGE as described in Example 3 revealed 3 distinct bands. The bands were denoted flea saliva proteins fspN1, fspN2 and fspN3. The N-terminal partial amino acid sequence of fspN1 was determined to be N D E L K F V F V M A K, also denoted SEQ ID NO:11. The N-terminal partial amino acid sequence of fspN2 was determined to be X D E L K F V F V M A K G P S X Q A X D Y P C, also denoted SEQ ID NO:12. The N-terminal partial amino acid sequence of fspN3 was determined to be E L K F V F A T A R G M S H T P C D Y P, also denoted SEQ ID NO:13. Comparison of SEQ ID NO:11 and SEQ ID NO:12 suggests that fspN1 and fspN2 share the same N-terminal sequence. Since fspN1 and fspN2 migrate differently when submitted to SDS-PAGE, however, the two proteins are likely to be different homologues, possibly due to one protein having a longer C-terminal domain and/or due to post-translational modification(s). Comparison of SEQ ID NO:13 to SEQ ID NO:11 and SEQ ID NO:12 suggests that fspN3 may be a homologue of fspN1 and fspN2 with internal sequence variations.

Example 5

This example describes the further characterization of proteins contained in Peak H.

To determine the isoelectric pH of the proteins contained in Peak H, proteins present in that peak were resolved using standard isoelectric focussing techniques known to those of skill in the art; see, for example, O'Farrell, 1975, *J. Biol. Chem.*, Vol. 250, pp. 4007–4021. The pI value for proteins contained in Peak H is about pI 9, ranging from about pI 8.5 to about pI 9.6.

The molecular weight of proteins contained in Peak H was determined by ESMS. The ESMS procedure was performed on a Fisons VG quattro-SQ mass spectrometer. The mass range was calibrated for 100–2000 m/z. The injection rate was performed at 4 μl per minute. The cone voltage was set at 45 volts. The injection sample contained 0.1% formic acid in 50% acetonitrile at a protein concentration of about 100 pmole per μl. The results indicate that Peak H apparently contains a population of proteins all having a molecular weight of 8613±6 daltons.

Example 6

This example describes the isolation of nucleic acid sequences encoding at least portions of flea saliva proteins fspH and fspI.

A. Description of Flea libraries

Fed flea and unfed flea cDNA libraries were prepared using standard procedures. Briefly, about 3000 to 4000 fed fleas and about the same number of unfed fleas were collected separately, placed into a dry-ice cooled mortar/pestle and ground to a fine powder. RNA from the ground-up fleas was prepared by direct extraction using the guanidinium thiocyanate procedure followed by centrifugation in cesium chloride gradients (see, for example, Sambrook et al., ibid.). Cesium chloride-purified gelatinous RNA pellets were collected and dissolved in sterile TE buffer (10 mM Tris-HCl, pH 7.6 and 1 mM EDTA) containing 0.1% sodium dodecyl sulfate. The dissolved pellet was precipitated with addition of 3M sodium acetate, pH 5.2 to a final concentration of 0.2 mM and two volumes of absolute ethanol to remove residual CsCl. Total RNA was fractionated for enrichment of the mRNA fraction (procedures provided by Invitrogen Corp., San Diego, Calif.).

Isolated whole flea mRNA was used directly for cDNA synthesis and molecular cloning. The methods of cDNA synthesis and molecular cloning were those provided with the Lambda Zap-cDNA synthesis kit™ (available from Stratagene, Inc., La Jolla, Calif.). Following is a list of flea cDNA libraries prepared having the indicated number of total plaque forming units (PFU) packaged: (a) two whole fed flea cDNA expression libraries referred to as Library C (about 2.5×10$^6$ PFU) and Library H (about 1.3×10$^6$ PFU); (b) a whole unfed flea cDNA expression library (about 1.3×10$^6$ PFU); (c) a flea salivary gland cDNA expression library prepared from approximately 6000 salivary glands collected from fed and unfed fleas (about 1.5×10$^6$ PFU); and (d) a flea fed midgut cDNA expression library prepared from approximately 5000 isolated midguts (about 2.3×10$^6$ PFU).

B. Isolation of a Nucleic Acid Molecule encoding fspH

A nucleic acid molecule encoding a portion of flea saliva protein fspH was identified using the flea salivary gland CDNA expression library described in Example 6A.

Degenerate synthetic oligonucleotide primers were designed from the amino acid sequence deduced for fspH (see Example 4). Three synthetic oligonucleotides were synthesized that corresponded to the region of fspH spanning from about residues 38 through 51 of SEQ ID NO:2: Primer 1, a "sense" primer corresponding to amino acid residues from about 38 through about 44 of SEQ ID NO:2, has the nucleic acid sequence 5' AAT(C) AAT(C) AAT(C) AAT(C) CCT(GAC) TGT(C) CA 3', and is denoted SEQ ID NO:15. Primer 2, an "antisense" primer corresponding to amino acid residues from about 46 through about 51 of SEQ ID NO:2, has the nucleic acid sequence 5' CA C(T)TC C(TAG)CT(G) CAT G(A)CA G(A)AA 3' and is denoted SEQ ID NO:16. Primer 3, a sense primer corresponding to amino acid residues from about 43 through about 48 of SEQ ID NO:2, has the nucleic acid sequence 5' TGT(C) CAT(C) T(C)TG(ATC) TTT(C) TGC(T) ATG-3' and is denoted SEQ ID NO:17. A fourth primer, Primer 4, was synthesized that corresponded to the carboxyl region of fspH, namely spanning from about amino residue 69 through 76 of SEQ ID NO:2. Primer 4, an antisense primer, has the nucleic acid sequence 5' GGA(CGA) GCT(C) TCA(G) CAA(G) TAA (G) CAA(G) TGT(C) TT' 3', denoted SEQ ID NO:18.

PCR amplification of fragments from the flea salivary gland library was conducted using standard techniques. PCR amplification products were generated using the combination of Primer 1 and the M13 forward universal standard primer 5' GTAAAACGACGGCCAGT 3', denoted SEQ ID NO:19. The resultant PCR amplification products were used for a nested PCR amplification using Primer 3 and Primer 4. The resultant PCR product, a fragment of 101 nucleotides denoted nfspH$_{101}$, was cloned into the Invitrogen TA™ cloning vector (procedures provided by Invitrogen) and submitted to DNA sequence analysis using standard techniques. The resulting nucleic acid sequence is presented as SEQ ID NO:20: T TGT CAC TTT TTT TGT ATG AGA GAA TGC AGG TCA GGA AAC GGC GGT TGC GGA AAC GGA GGA AGG ACA AGA CCT GAT TCG AAG CAC TGC TAT GC (primer-derived sequences are underlined). The 60 nucleotides of internal non-primer-derived sequence codes for 20 amino acids of fspH, spanning from residue about 48 through about 68, as numbered in SEQ ID NO:2.

Using standard techniques, nucleic acid molecule nfspH$_{101}$ can be used as a probe to isolate a nucleic acid molecule that encodes a protein corresponding to a full-length, or larger partial, fspI protein.

C. Isolation of a Nucleic Acid Molecule encoding fspH

The amino acid sequence for fspI (SEQ ID NO:6) disclosed in Example 4 was used to design a set of synthetic degenerate oligonucleotide PCR amplification primers. Degenerate Primer 5, a sense primer corresponding to residues from about 1 through about 8 of SEQ ID NO:6, has the nucleic acid sequence 5' GAA(G) GAT(C) ATT(Calif.) TGG AAA(G) GTT(CAG) AAT(C) AA 3', denoted SEQ ID NO:21. Degenerate Primer 6, a sense primer corresponding to residues from about 11 through about 18 of SEQ ID NO:6, has the nucleic acid sequence 5' ACT(CGA) TCT(CGA) GGT(CGA) GGT(CGA) AAA(G) AAT(C) CAA(G) GA 3', denoted SEQ ID NO:22.

Primers 5 and 6 were used in combination with the vector primers BSKX (5' TTGGGTACCGGGCCCCCCCT 3', SEQ ID NO:23) and the M13 primer denoted by SEQ ID NO:19 in order to generate PCR amplification products. The PCR products were cloned into the Invitrogen TA™ vector and subjected to DNA sequence analysis. One cloned product analyzed, called nfspI$_{573}$ contained a 573-nucleotide product that corresponded, at least in part, to the partial amino acid sequence determined for fspI. The nucleotide sequence of nfspI$_{573}$ is presented as SEQ ID NO:24: CTTACGTC-CGGGGGTAAGAATCAGGATAGAAAACTC-GATCAAATAATTCAAA AAGGCC AACAAGTT-AAAATCCAAAATATTTGCAAATTAATACGAGAT-AAACC ACATACAAATCAAGAGAAAGAAAAATG-TATGAAATTTTGCACAAAAACGTT TGCAAAGGT-TATAGAGGAGCTTGTGATG-GCAATATTTGCTACTGCAGCAGGC CAAGTAATTTAGGTCCTGATTGGAAAGT- CAACGAAAGAATCGAAAGACTCCC AATAACAAA-
GATTCTCGTCTCAGGAAATAGTTC-
CATATCGACAACAATTACG
AATTCCAAATATTTCGAAACTAAAAAT-
TCAGAGACCAATGAAGATTCCAAAT CGAAAAAA-
CATTCGAAAGAAAAATGTCGTGGTG-
GAAATGATGCTGGATGTG
ATGGAAACGTTTTGTTATTGTCGAC-
CAAAAAATAAATAATAATTATAATAAA TAAATTGT-
TATAGTTATTAGTTATCCCGTCA-
CATATTAGAAAAGTGGCTTATA
ATTTATGAACAATATAACACATAAATT-
AGTTGTGTAAAAAAAAAAAAAAAAA A Translation of SEQ ID NO:24 yields the following longest open reading frame, denoted as SEQ ID NO:25:

L T S G G K N Q D R K L D Q I I Q K G Q Q V K I Q

N I C K L I R D K P H T N Q E K E K C M K F C T K

N V C K G Y R G A C D G N I C Y C S R P S N L G P

D W K V N E R I E R L P I T K I L V S G N S S I S

T T I T N S K Y F E T K N S E T N E D S K S K K H

S K E K C R G G N D R G C D G N V L L L S T K K.

By combining the partial N-terminal sequence of fspI (SEQ ID NO:6) with the protein sequence SEQ ID NO:25 deduced from the nucleic acid sequence SEQ ID NO:24, it is possible to obtain an apparent full-length amino acid sequence for fspI, denoted SEQ ID NO:26:

E D I W K V N K K L T S G G K N Q D R K L D Q I I

Q K G Q Q V K I Q N I C K L I R D K P H T N Q E K

E K C M K F C T K N V C K G Y R G A C D G N I C Y

C S R P S N L G P D W K V N E R I E R L P I T K I

L V S G N S S I S T T I T N S K Y F E T K N S E T

N E D S K S K K H S K E K C R G G N D R G C D G N

V L L L S T K K.

Example 7

This example demonstrates the ability of a formulation of the present invention to induce flea allergy dermatitis in an animal susceptible to flea allergy dermatitis.

To determine whether the isolated flea saliva proteins described in Examples 2 and 3 were capable of inducing an allergic response in animals susceptible to flea allergy dermatitis, skin tests were performed on sensitized dogs. Six dogs were sensitized to fleas using the method of Gross, et al., 1985, *Veterinary Pathology*, Vol. 22, pp. 78–71. Briefly, each dog was exposed to about 25 C. felis fleas contained in chambers by allowing the contained fleas to feed on the experimental dogs for about 15-minute periods at weekly intervals. The six dogs were sensitized over the following periods: Dog 2080109 was exposed to fleas 38 times over a period spanning Aug. 31, 1993 through Jun. 7, 1994. Dog 2082101 was exposed to fleas 22 times over a period spanning Dec. 14, 1993 through Jun. 7, 1994. Dog 2082128 was exposed to fleas 20 times over a period spanning Aug. 31, 1993 through May 24, 1994. Dog BFQ2 was exposed to fleas 17 times over a period spanning Mar. 15, 1994 through Jul. 12, 1994. Dog CPO2 was exposed to fleas 12 times over a period spanning Mar. 15, 1994 through Jun. 7, 1994. Dog CQQ2 was exposed to fleas 1 time on Mar. 15, 1994.

Skin testing was performed the morning of Jul. 21, 1994. The dogs were shaved in the lateral thorax/abdominal area and intradermally injected in that area with a variety of formulations of the present invention as well as with control solutions. The total volume per injection was 50 microliters ($\mu$l), with the formulations and controls being diluted in phenolated saline. Each dog received the injections listed in Table 1.

Table 1. Samples administered to dogs.

TABLE 1

| | Samples administered to dogs | | |
|---|---|---|---|
| SAMPLE | REPLICATES | $\mu$g/inj | FLEA-HOUR |
| DILUENT | 2 | N/A* | N/A |
| HISTAMINE | 2 | 1.38 | N/A |
| GREER | 3 | 50 (w/v) | N/A |
| FS-1 | 3 | 1.88 | 4,660 |
| A | 3 | 0.23 | 23,000 |
| B | 3 | 0.32 | 23,000 |
| C1 | 3 | 1.10** | 23,000 |
| C2 | 3 | 0.42 | 23,000 |
| D1 | 3 | 0.24 | 23,000 |
| D2 | 3 | 0.29 | 23,000 |
| E | 3 | 0.16 | 23,000 |
| F | 3 | 0.10 | 23,000 |
| G | 3 | 0.21 | 23,000 |
| H | 3 | 0.20 | 23,000 |
| I | 3 | 0.12 | 23,000 |
| J | 3 | 0.08 | 23,000 |
| K | 3 | 0.12 | 23,000 |
| L | 3 | 0.08 | 23,000 |
| M1 | 3 | 0.16 | 23,000 |
| M2 | 3 | 0.27 | 23,000 |
| N | 3 | 0.20 | 23,000 |
| FS-2 | 3 | 0.71 | 4,660 |

*N/A is not applicable
**Apparent amount, probably artificially high due to assay interference Note that in these studies, fspJ1 and fspJ2 were administered together as fspJ; fspL1 and fspL2 were administered together as fspL; fspN1, fspN2 and fspN3 were administered together as fspN. It is also to be noted that A, B, C1, C2, D1, D2, E, F, G, H, I, J, K, L, M1, M2 and N refer, respectively to flea saliva proteins fspA, fspB, fspC1, fspC2, fspD1, fspD2, fspE, fspF, fspG, fspH, fspI, fspJ, fspK, fspL, fspM1, fspM2 and fspN. The negative control comprised diluent (NC) and the positive controls comprised Greer antigen (GR) and histamine (HIS). The amount of Greer antigen used was determined by weight per volume (w/v) according to the information provided by the manufacturers (Greer Laboratories, Inc., Lenoir, N.C.). The amount of histamine used was determined by information provided on the supplier's label (available from Greer Laboratories, Inc., Lenoir, N.C.).

A. Comparison of Wheal Sizes at Sites of Injection

All injection sites were objectively (Obj) measured in millimeters (mm) at 15 min and subjectively (Sub) scored on a scale of 0 to 4. The subjective scoring was performed by Kenneth W. Kwochka, D.V.M., Diplomat ACVD, President ACVD (American College of Veterinary Dermatologists) at Ohio State University, Columbus, Ohio. Tables 2 through 7 indicate the results obtained for each dog. # refers to the number designation given to each sample; antigen refers to the sample. Inj 1, Inj 2 and Inj 3 refer to triplicate injections and NA refers to "not applicable."

TABLE 2

DOG ID: 2082101

| # Antigen | Inj 1 Sub | Inj 1 Obj | Inj 2 Sub | Inj 2 Obj | Inj 3 Sub | Inj 3 Obj |
|---|---|---|---|---|---|---|
| 1 Neg Cntl | 0 | 6 | NA | NA | NA | NA |
| 2 Histamine | 4 | 12 | NA | NA | NA | NA |
| 3 Greer | 3 | 10 | 3 | 10 | 3 | 10 |
| 4 FS-1 | 3 | 10 | 4 | 12 | 4 | 12 |
| 5 A | 1 | 8 | 0 | 8 | 0 | 8 |
| 6 B | 0 | 6 | 0 | 6 | 0 | 6 |
| 7 C1 | 0 | 6 | 0 | 6 | 0 | 6 |
| 8 C2 | 0 | 6 | 0 | 6 | 0 | 6 |
| 9 D1 | 0 | 8 | 0 | 8 | 0 | 6 |
| 10 D2 | 0 | 6 | 0 | 6 | 0 | 8 |
| 11 E | 3 | 12 | 3 | 12 | 3 | 12 |
| 12 F | 3 | 14 | 3 | 12 | 3 | 12 |
| 13 G | 3 | 12 | 3 | 12 | 3 | 12 |
| 14 H | 3 | 11 | 2 | 12 | 3 | 12 |
| 15 I | 3 | 12 | 2 | 12 | 3 | 11 |
| 16 J | 2 | 10 | 2 | 11 | 2 | 10 |
| 17 K | 2 | 11 | 2 | 10 | 2 | 9 |
| 18 L | 2 | 9 | 1 | 10 | 1 | 10 |
| 19 M1 | 2 | 12 | 2 | 11 | 2 | 11 |
| 20 M2 | 3 | 12 | 3 | 11 | 3 | 12 |
| 21 N | 3 | 11 | 3 | 10 | 2 | 11 |
| 22 FS-2 | 2 | 11 | 3 | 12 | 2 | 10 |
| 23 Neg Cntl | 0 | 8 | NA | NA | NA | NA |
| 24 Histamine | 4 | 14 | NA | NA | NA | NA |

TABLE 3

DOG ID: 2080109

| # Antigen | Inj 1 Sub | Inj 1 Obj | Inj 2 Sub | Inj 2 Obj | Inj 3 Sub | Inj 3 Obj |
|---|---|---|---|---|---|---|
| 1 Neg Cntl | 0 | 7 | NA | NA | NA | NA |
| 2 Histamine | 4 | 14 | NA | NA | NA | NA |
| 3 Greer | 0 | 8 | 0 | 8 | 0 | 8 |
| 4 FS-1 | 4 | 13 | 4 | 13 | 4 | 13 |
| 5 A | 0 | 9 | 0 | 8 | 0 | 8 |
| 6 B | 0 | 7 | 0 | 7 | 0 | 7 |
| 7 C1 | 0 | 8 | 0 | 7 | 0 | 7 |
| 8 C2 | 0 | 8 | 0 | 7 | 0 | 8 |
| 9 D1 | 1 | 9 | 1 | 9 | 1 | 9 |
| 10 D2 | 1 | 9 | 1 | 8 | 1 | 8 |
| 11 E | 3 | 11 | 3 | 11 | 2 | 10 |
| 12 F | 3 | 11 | 3 | 13 | 4 | 13 |
| 13 G | 3 | 14 | 3 | 13 | 3 | 13 |
| 14 H | 2 | 12 | 2 | 11 | 2 | 10 |
| 15 I | 2 | 10 | 3 | 10 | 3 | 10 |
| 16 J | 2 | 10 | 3 | 10 | 3 | 10 |
| 17 K | 2 | 9 | 2 | 9 | 2 | 9 |
| 18 L | 1 | 9 | 1 | 6 | 1 | 7 |
| 19 M1 | 3 | 11 | 3 | 13 | 3 | 13 |
| 20 M2 | 3 | 14 | 3 | 13 | 3 | 14 |
| 21 N | 3 | 13 | 3 | 14 | 2 | 10 |
| 22 FS-2 | 2 | 9 | 1 | 7 | 1 | 8 |
| 23 Neg Cntl | 0 | 6 | NA | NA | NA | NA |
| 24 Histamine | 4 | 16 | NA | NA | NA | NA |

TABLE 4

DOG ID: 2082128

| # Antigen | Inj 1 Sub | Inj 1 Obj | Inj 2 Sub | Inj 2 Obj | Inj 3 Sub | Inj 3 Obj |
|---|---|---|---|---|---|---|
| 1 Neg Cntl | 0 | 6 | NA | NA | NA | NA |
| 2 Histamine | 4 | 12 | NA | NA | NA | NA |
| 3 Greer | 0 | 6 | 0 | 6 | 0 | 6 |
| 4 FS-1 | 3 | 12 | 3 | 12 | 3 | 12 |
| 5 A | 0 | 7 | 0 | 7 | 0 | 6 |
| 6 B | 0 | 7 | 0 | 7 | 0 | 6 |
| 7 C1 | 0 | 7 | 0 | 6 | 0 | 7 |
| 8 C2 | 0 | 6 | 0 | 7 | 0 | 7 |
| 9 D1 | 0 | 7 | 0 | 7 | 0 | 7 |
| 10 D2 | 0 | 7 | 0 | 7 | 0 | 7 |
| 11 E | 0 | 7 | 0 | 6 | 0 | 7 |
| 12 F | 0 | 6 | 0 | 6 | 0 | 6 |
| 13 G | 1 | 10 | 1 | 9 | 1 | 9 |
| 14 H | 2 | 10 | 2 | 10 | 2 | 11 |
| 15 I | 3 | 12 | 3 | 12 | 3 | 11 |
| 16 J | 3 | 12 | 3 | 11 | 3 | 11 |
| 17 K | 3 | 11 | 3 | 12 | 3 | 12 |
| 18 L | 3 | 11 | 3 | 10 | 3 | 11 |
| 19 M1 | 3 | 11 | 3 | 11 | 3 | 12 |
| 20 M2 | 3 | 12 | 3 | 12 | 3 | 12 |
| 21 N | 3 | 12 | 3 | 12 | 3 | 12 |
| 22 FS-2 | 3 | 12 | 3 | 11 | 3 | 12 |
| 23 Neg Cntl | 0 | 6 | NA | NA | NA | NA |
| 24 Histamine | 4 | 14 | NA | NA | NA | NA |

TABLE 5

DOG ID: BFQ2

| # Antigen | Inj 1 Sub | Inj 1 Obj | Inj 2 Sub | Inj 2 Obj | Inj 3 Sub | Inj 3 Obj |
|---|---|---|---|---|---|---|
| 1 Neg Cntl | 0 | 6 | NA | NA | NA | NA |
| 2 Histamine | 4 | 12 | NA | NA | NA | NA |
| 3 Greer | 0 | 6 | 0 | 6 | 0 | 6 |
| 4 FS-1 | 1 | 9 | 1 | 9 | 1 | 9 |
| 5 A | 0 | 7 | 0 | 7 | 0 | 7 |
| 6 B | 0 | 7 | 0 | 7 | 0 | 7 |
| 7 C1 | 0 | 7 | 1 | 7 | 1 | 7 |
| 8 C2 | 0 | 7 | 0 | 7 | 0 | 6 |
| 9 D1 | 0 | 8 | 1 | 7 | 1 | 8 |
| 10 D2 | 0 | 7 | 0 | 6 | 1 | 7 |
| 11 E | 1 | 7 | 0 | 6 | 0 | 6 |
| 12 F | 1 | 6 | 1 | 7 | 0 | 7 |
| 13 G | 0 | 8 | 1 | 8 | 1 | 8 |
| 14 H | 0 | 8 | 0 | 7 | 0 | 7 |
| 15 I | 1 | 7 | 0 | 7 | 0 | 8 |
| 16 J | 0 | 7 | 0 | 7 | 0 | 7 |
| 17 K | 0 | 7 | 0 | 7 | 0 | 6 |
| 18 L | 0 | 8 | 0 | 7 | 0 | 7 |
| 19 M1 | 0 | 7 | 0 | 7 | 0 | 7 |
| 20 M2 | 0 | 7 | 0 | 7 | 1 | 8 |
| 21 N | 3 | 12 | 3 | 11 | 3 | 11 |
| 22 FS-2 | 3 | 11 | 3 | 11 | 3 | 11 |
| 23 Neg Cntl | 0 | 7 | NA | NA | NA | NA |
| 24 Histamine | 4 | 15 | NA | NA | NA | NA |

TABLE 6

DOG ID: CPO2

| # Antigen | Inj 1 Sub | Inj 1 Obj | Inj 2 Sub | Inj 2 Obj | Inj 3 Sub | Inj 3 Obj |
|---|---|---|---|---|---|---|
| 1 Neg Cntl | 0 | 3 | NA | NA | NA | NA |
| 2 Histamine | 4 | 13 | NA | NA | NA | NA |
| 3 Greer | 0 | 7 | 0 | 7 | 0 | 6 |
| 4 FS-1 | 4 | 12 | 4 | 12 | 4 | 12 |
| 5 A | 0 | 7 | 0 | 6 | 0 | 6 |
| 6 B | 0 | 6 | 0 | 7 | 0 | 7 |
| 7 C1 | 0 | 7 | 0 | 6 | 0 | 7 |
| 8 C2 | 0 | 6 | 0 | 6 | 0 | 6 |
| 9 D1 | 0 | 7 | 1 | 7 | 0 | 7 |
| 10 D2 | 1 | 6 | 0 | 6 | 0 | 5 |

TABLE 6-continued

DOG ID: CPO2

| # Antigen | Inj 1 Sub | Inj 1 Obj | Inj 2 Sub | Inj 2 Obj | Inj 3 Sub | Inj 3 Obj |
|---|---|---|---|---|---|---|
| 11 E | 0 | 6 | 0 | 6 | 0 | 6 |
| 12 F | 0 | 6 | 0 | 6 | 2 | 7 |
| 13 G | 2 | 9 | 2 | 8 | 2 | 8 |
| 14 H | 4 | 11 | 4 | 12 | 4 | 11 |
| 15 I | 3 | 12 | 3 | 11 | 3 | 10 |
| 16 J | 3 | 10 | 3 | 11 | 3 | 10 |
| 17 K | 2 | 8 | 2 | 8 | 2 | 8 |
| 18 L | 1 | 8 | 1 | 7 | 1 | 7 |
| 19 M1 | 3 | 11 | 3 | 11 | 3 | 11 |
| 20 M2 | 3 | 11 | 4 | 12 | 4 | 12 |
| 21 N | 4 | 12 | 3 | 10 | 3 | 11 |
| 22 FS-2 | 3 | 11 | 3 | 12 | 3 | 12 |
| 23 Neg Cntl | 0 | 6 | NA | NA | NA | NA |
| 24 Histamine | 4 | 13 | NA | NA | NA | NA |

TABLE 7

DOG ID: COO2

| # Antigen | Inj 1 Sub | Inj 1 Obj | Inj 2 Sub | Inj 2 Obj | Inj 3 Sub | Inj 3 Obj |
|---|---|---|---|---|---|---|
| 1 Neg Cntl | 0 | 6 | NA | NA | NA | NA |
| 2 Histamine | 4 | 13 | NA | NA | NA | NA |
| 3 Greer | 0 | 7 | 0 | 7 | 0 | 7 |
| 4 FS-1 | 2 | 8 | 2 | 8 | 2 | 8 |
| 5 A | 0 | 6 | 0 | 6 | 0 | 7 |
| 6 B | 0 | 7 | 0 | 7 | 0 | 6 |
| 7 C1 | 0 | 7 | 0 | 6 | 0 | 6 |
| 8 C2 | 0 | 7 | 0 | 7 | 0 | 6 |
| 9 D1 | 0 | 6 | 0 | 6 | 0 | 6 |
| 10 D2 | 0 | 6 | 0 | 6 | 0 | 7 |
| 11 E | 0 | 6 | 0 | 6 | 0 | 6 |
| 12 F | 0 | 6 | 0 | 7 | 0 | 7 |
| 13 G | 0 | 7 | 0 | 7 | 0 | 6 |
| 14 H | 1 | 7 | 1 | 7 | 1 | 7 |
| 15 I | 2 | 8 | 2 | 9 | 2 | 8 |
| 16 J | 2 | 8 | 2 | 8 | 2 | 8 |
| 17 K | 1 | 7 | 1 | 7 | 1 | 7 |
| 18 L | 1 | 6 | 0 | 6 | 0 | 6 |
| 19 M1 | 2 | 7 | 2 | 8 | 2 | 8 |
| 20 M2 | 2 | 8 | 2 | 8 | 2 | 9 |
| 21 N | 3 | 11 | 3 | 12 | 3 | 11 |
| 22 FS-2 | 3 | 11 | 3 | 11 | 3 | 10 |
| 23 Neg Cntl | 0 | 7 | NA | NA | NA | NA |
| 24 Histamine | 4 | 14 | NA | NA | NA | NA |

As a control, 2 flea naive dogs (i.e., dogs that had never been exposed to fleas) were also tested with single replicates of the same samples that were injected into the sensitized dogs. These dogs are referred to as WANU and WBCE. objective and subjective wheal size measurements 15 minutes after injection of the samples are shown in Tables 8 and 9.

TABLE 8

DOG ID: WANU

| #Antigen | Inj 1 Sub | Inj 1 Obj |
|---|---|---|
| 1 Neg Cntl | 0 | 7 |
| 2 Histamine | 4 | 10 |
| 3 Greer | 0 | 6 |
| 4 FS-1 | 0 | 6 |
| 5 A | 0 | 7 |
| 6 B | 0 | 6 |

TABLE 8-continued

DOG ID: WANU

| #Antigen | Inj 1 Sub | Inj 1 Obj |
|---|---|---|
| 7 C1 | 0 | 6 |
| 8 C2 | 0 | 6 |
| 9 D1 | 0 | 7 |
| 10 D2 | 0 | 6 |
| 11 E | 0 | 6 |
| 12 F | 0 | 6 |
| 13 G | 0 | 7 |
| 14 H | 0 | 7 |
| 15 I | 0 | 7 |
| 16 J | 0 | 7 |
| 17 K | 0 | 6 |
| 18 L | 0 | 7 |
| 19 M1 | 0 | 6 |
| 20 M2 | 0 | 6 |
| 21 N | 1 | 8 |
| 22 FS-2 | 1 | 8 |
| 23 Neg Cntl | NA | NA |
| 24 Histamine | NA | NA |

TABLE 9

DOG ID: WBCE

| # Antigen | Inj 1 Sub | Inj 1 Obj |
|---|---|---|
| 1 Neg Cntl | 0 | 6 |
| 2 Histamine | 4 | 12 |
| 3 Greer | 0 | 7 |
| 4 FS-1 | 0 | 7 |
| 5 A | 0 | 7 |
| 6 B | 0 | 7 |
| 7 C1 | 0 | 7 |
| 8 C2 | 0 | 7 |
| 9 D1 | 0 | 7 |
| 10 D2 | 0 | 6 |
| 11 E | 0 | 7 |
| 12 F | 0 | 7 |
| 13 G | 0 | 8 |
| 14 H | 0 | 7 |
| 15 I | 0 | 7 |
| 16 J | 0 | 7 |
| 17 K | 0 | 7 |
| 18 L | 0 | 6 |
| 19 M1 | 0 | 7 |
| 20 M2 | 0 | 7 |
| 21 N | 0 | 7 |
| 22 FS-2 | 0 | 7 |
| 23 Neg Cntl | NA | NA |
| 24 Histamine | NA | NA |

The average subjective score obtained for each flea saliva antigen from the 6 sensitized dogs tested was calculated and is summarized in FIG. 5. The results indicate that the flea saliva products produced as described in Examples 2 and 3 include at least one allergenic protein capable of inducing an immediate hypersensitive response in a sensitized dog. In particular, injection of the mixtures of flea saliva antigens referred to as FS-1 and FS-2 resulted in substantial wheal formation. Flea saliva proteins fspE, fspF, fspG, fspH, fspI, fspJ, fspK, fspL, fspM1, fspM2 and fspN also resulted in substantial wheal formation. Flea saliva proteins fspA, fspB, fspC1, fspC2, fspD1 and fspD2 produced minimal, if any, allergic response, depending on the dog being tested. The sample containing fspH produced the largest wheal formation when compared with the other flea saliva proteins.

B. Comparison of Levels of Induration and Erythema at the Injection Sites

In addition to wheal size, the amount of induration and erythema were also measured at each site of injection. Induration produced by the injection of the flea saliva antigens was measured at 6 hours and 24 hours by subjective scoring. Such subjective induration measurements were performed by Kenneth W. Kwochka, D.V.M. In addition, the amount of erythema at each site of injection were subjectively scored by Kenneth W. Kwochka, D.V.M.

The amounts of induration and erythema measured by subjective scoring at 6 hours were negative for each of the sensitized and control dogs except for the following formulations in the following sensitized dogs. Administration of FS-1 to Dog 2082101 produced an average induration score of 1 at 2 sites of injection but no erythema score. Administration of fspL to Dog 2082101 produced no induration but an erythema score of 1 at 1 site of injection. Administration of fspM1 to Dog 2082101 produced no induration but an erythema score of 3 at 1 site of injection. Administration of FS-2 to Dog 2082101 produced no induration but an average erythema score of 1.33 at 3 sites of injection.

Administration of fspH to Dog 2082128 produced no induration but an average erythema score of 2 at 3 sites of injection. Administration of fspI to Dog 2082128 produced an average induration score of 1 and an average erythema score of 1 at 2 sites of injection. Administration of fspJ to Dog 2082128 produced an average induration score of 1 and an average erythema score of 1 at 3 sites of injection. Administration of FS-2 to Dog 2082128 produced no induration but an average erythema score of 2 at 3 sites of injection.

Administration of FS-1 to Dog BFQ2 produced an average induration score of 2 and an average erythema score of 2 at 3 sites of injection. Administration of fspN to Dog BFQ2 produced an average induration score of 1 and an average erythema score of 2 at 2 sites of injection. Administration of FS-2 to Dog BFQ2 produced an average induration score of 1 and an average erythema score of 2 at 2 sites of injection.

Administration of FS-1 to Dog CPO2 produced an average induration score of 2.5 but no erythema at 2 sites of injection. Administration of fspG to Dog CPO2 produced no induration but an average erythema score of 2 at 3 sites of injection. Administration of fspH to Dog CPO2 produced no induration but an average erythema score of 1 at 2 sites of injection. Administration of FS-2 to Dog CPO2 produced no induration but an average erythema score of 2 at 3 sites of injection.

Figure 7:
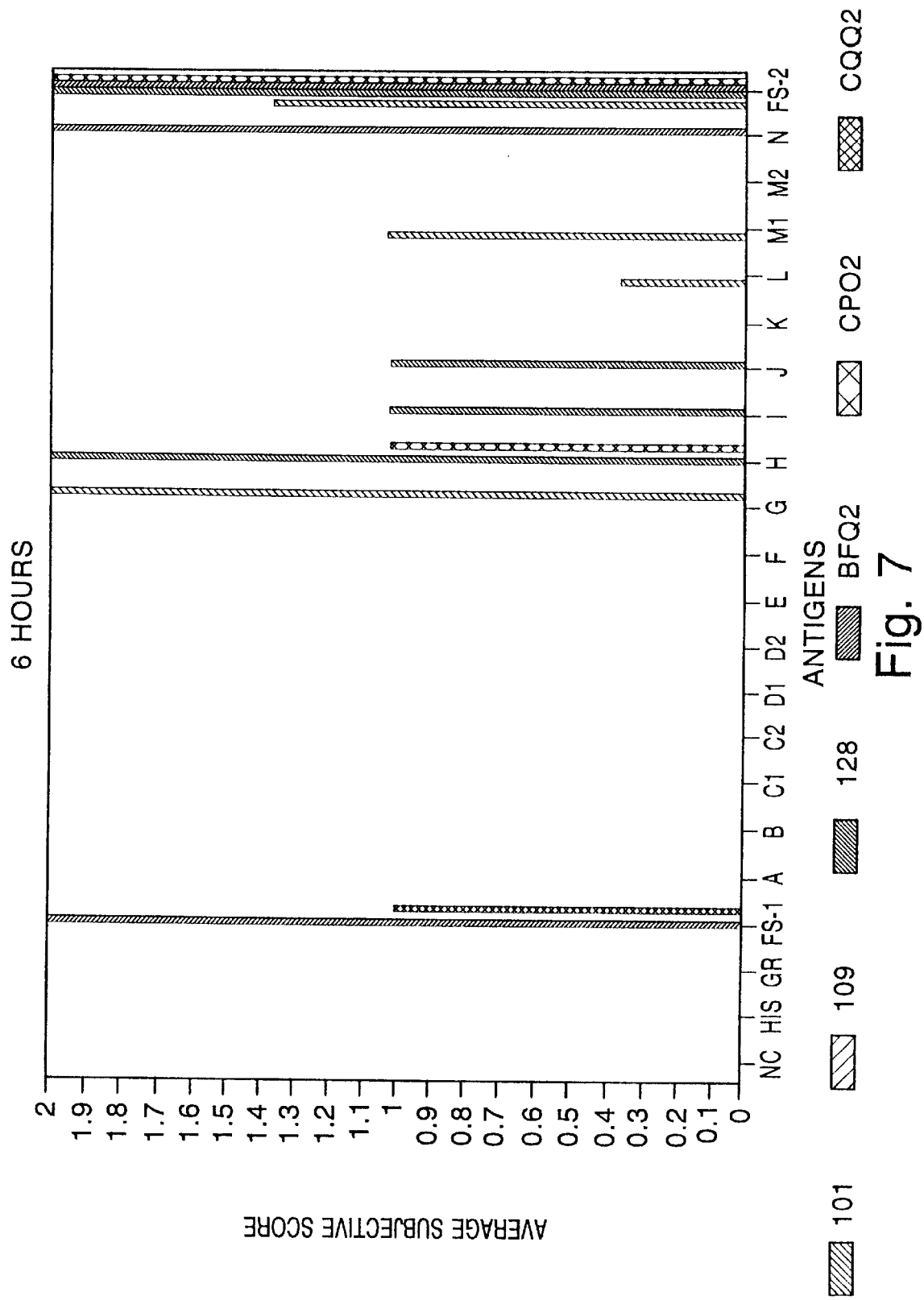
FIG. 7 illustrates the relative erythema of wheals 6 hours after injection of various flea saliva protein formulations into flea-sensitized dogs.

The average subjective score for induration obtained for each flea saliva antigen from the 6 sensitized dogs tested was calculated and is summarized in FIG. 6. The average subjective score for erythema obtained for each flea saliva antigen from the 6 sensitized dogs tested was calculated and is summarized in FIG. 7.

The amounts of induration and erythema measured by subjective scoring at 24 hours results for five of the flea-sensitized dogs and the two control dogs were negative except for the following formulations in the following sensitized dogs.

Administration of fspI to Dog 2082101 produced an average induration score of 1 and an average erythema score of 1 at 3 sites of injection. Administration of fspj to Dog 2082101 produced an average induration score of 1 and an average erythema score of 1 at 3 sites of injection. Administration of fspM1 to Dog 2082101 produced an average induration score of 1 and an average erythema score of 3 at 3 sites of injection. Administration of fspN to Dog 2082101 produced an average induration score of 1 and an average erythema score of 2 at 3 sites of injection. Administration of FS-2 to Dog 2082101 produced an average induration score of 3 and an average erythema score of 4 at 3 sites of injection.

Administration of FS-1 to Dog BFQ2 produced an average induration score of 1 and an average erythema score of 1 at 3 sites of injection. Administration of FS-2 to Dog BFQ2 produced an induration score of 1 and an erythema score of 1 at 1 site of injection.

Administration of FS-1 to Dog CPO2 produced an induration score of 2 and an erythema score of 1 at 1 site of injection. Administration of fspI to Dog CPO2 produced an average induration score of 1 and an average erythema score of 1 at 3 sites of injection. Administration of FS-2 to Dog CPO2 produced an average induration score of 1 and an average erythema score of 2 at 3 sites of injection.

Administration of Greer antigen to Dog CQQ2 produced no induration but an average erythema score of 1 at 3 sites of injection. Administration of FS-1 to Dog CQQ2 produced an induration score of 1 and an erythema score of 1 at 1 site of injection. Administration of fspI, fspJ, fspM1 or fspM2 to Dog CQQ2 produced no induration but an average erythema score of 1 at 3 sites of injection. Administration of fspN to Dog CQQ2 produced an induration score of 1 and an erythema score of 1 at 1 site of injection. Administration of FS-2 to Dog CQQ2 produced an average induration score of 1 and an average erythema score of 2 at 3 sites of injection.

Figure 8:
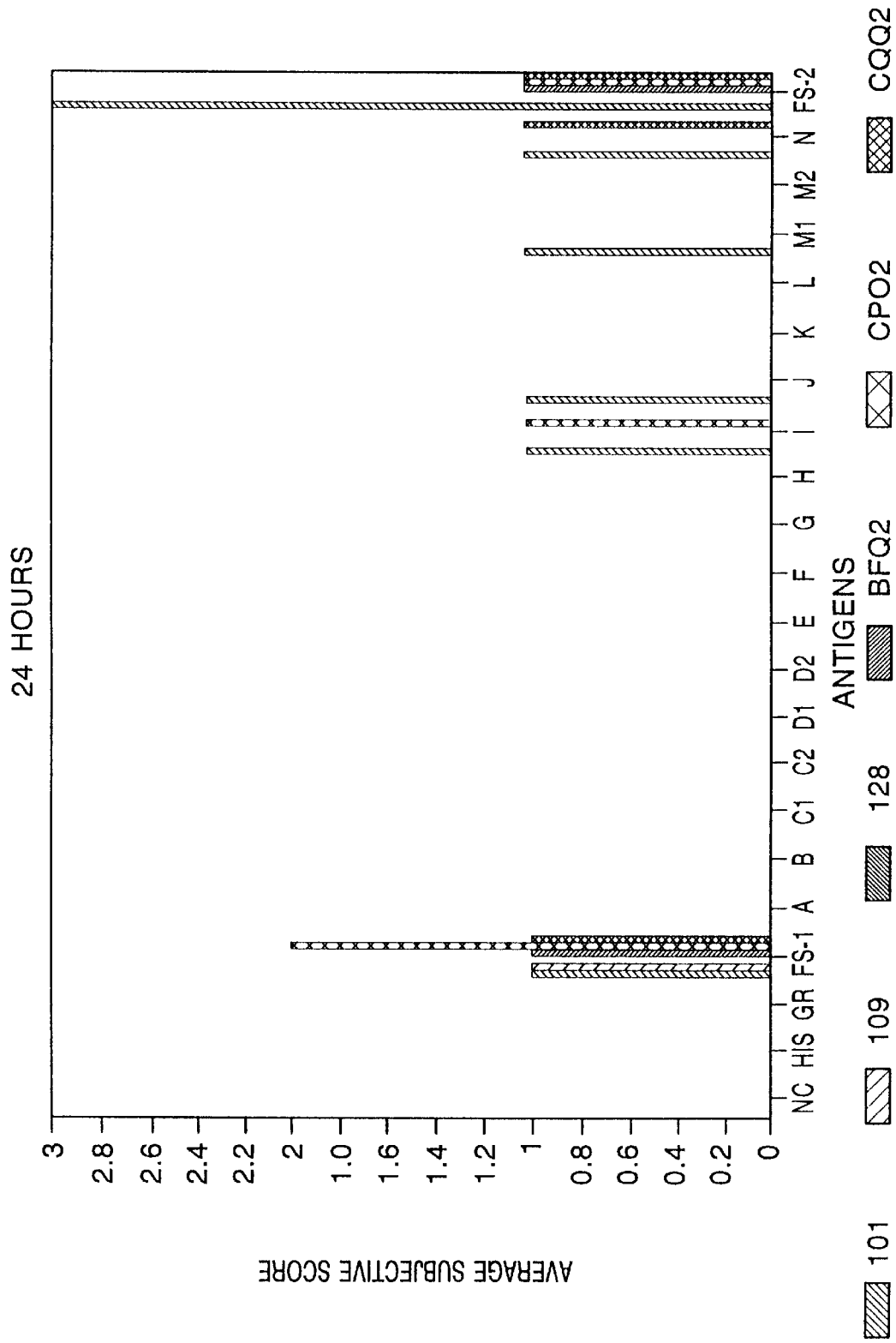
FIG. 8 illustrates the relative induration of wheals 24 hours after injection of various flea saliva protein formulations into flea-sensitized dogs.

The average subjective score for induration obtained for each flea saliva antigen from the 6 sensitized dogs tested was calculated and is summarized in FIG. 8. The average subjective score for erythema obtained for each flea saliva antigen from the 6 sensitized dogs tested was calculated and is summarized in FIG. 9.

The results indicate that at least some of the flea saliva protein formulations produced as described in Examples 2 and 3 include at least one allergenic protein capable of inducing a delayed hypersensitive response in a sensitized dog. Injection of the mixtures of flea saliva proteins referred to as FS-1 and FS-2 induced substantial induration and erythema for at least 24 hours. In addition, the flea saliva protein samples fspI, fspJ, M1 and fspN were sufficiently allergenic to induce induration and erythema for at least 24 hours. The flea saliva protein sample fspL and fspM2 induced substantial levels of induration but not substantial levels of erythema at 24 hours.

Taken together, the results shown indicated above and shown in FIGS. 5 through 9, indicate that saliva protein formulations of the present invention are sufficiently allergenic to induce a hypersensitive response in a sensitized dog. Numerous samples induced both an immediate hypersensitive response and a delayed hypersensitive response.

Example 8

This example demonstrates the ability of numerous flea saliva protein samples isolated in Examples 2 and 3 to induce a hypersensitive response by histopathology of tissue removed from selected lesions on the dogs described in Example 7.

Two tissue samples per dog were removed from each sensitized dog described in Example 7. No biopsies were taken from the two naive dogs. The selected sites from which the tissue samples were removed are indicated in Table 10 below. Biopsies were taken with a 4 mm biopsy punch after subcutaneous injections of Lidocaine. Biopsies were processed and read by Dr. David M. Getzy, DVM, Diplomat ACVP (American College of Veterinary Pathologists) at the Colorado Veterinary Diagnostic Laboratory (College of Veterinary Medicine and Biomedical Sciences, Colorado State University, Fort Collins, Colo.).

TABLE 10

Histopathology

| Dog | Antigen | Time | No. | Slide | Lesion Type | Grade |
|---|---|---|---|---|---|---|
| 101 | FS-1 | 15 min. | 1 | A | A | 1 |
| | | 6 hr. | 2 | B | A | 2.5 |
| | | 24 hr. | 3 | C | A | 3 |
| 109 | FS-1 | 15 min. | 4 | D | A | 1 |
| | | 6 hr. | 5 | E | C | 2 |
| | | 24 hr. | 6 | F | C | 3 |
| 128 | FS-1 | 15 min. | 7 | G | A | 1.5 |
| | | 6 hr. | 8 | H | C | 1.5 |
| | | 24 hr. | 9 | I | C | 3 |
| CPO2 | FS-1 | 15 min. | 10 | J | A | 1.5 |
| | | 6 hr. | 11 | K | C | 3 |
| | | 24 hr. | 12 | L | C | 4 |
| CQQ2 | FS-1 | 15 min. | 13 | M | A | 1.5 |
| | | 6 hr. | 14 | N | C | 2.5 |
| | | 24 hr. | 15 | O | C | 2.5 |
| 101 | fspE | 15 min. | 16 | P | A | 1 |
| | | 6 hr. | 17 | Q | C | 1.5 |
| | | 24 hr. | 18 | R | A | 1.5 |
| 109 | fspF | 15 min. | 19 | S | A | 1 |
| | | 6 hr. | 20 | T | A | 1.5 |
| | | 24 hr. | 21 | U | A | 1.5 |
| 128 | fspI | 15 min. | 22 | V | A | 1 |
| | | 6 hr. | 23 | W | C | 2.5 |
| | | 24 hr. | 24 | X | C | 2.5 |
| BFQ2 | fspN | 15 min. | 25 | Y | A | 1.5 |
| | | 6 hr. | 26 | Z | C | 2 |
| | | 24 hr. | 27 | AA | C | 3.5 |
| BFQ2 | fspO | 15 min. | 28 | BB | A | 1 |
| | | 6 hr. | 29 | CC | C | 3 |
| | | 24 hr. | 30 | DD | C | 2.5 |
| CPO2 | fspH | 15 min. | 31 | EE | A | 1.5 |
| | | 6 hr. | 32 | FF | C | 1.5 |
| | | 24 hr. | 33 | GG | A | 1.5 |
| CQQ2 | fspN | 15 min. | 34 | HH | A | 1 |
| | | 6 hr. | 35 | II | C | 2.5 |
| | | 24 hr. | 36 | JJ | C | 2.5 |

Two types of lesions were found in the tissue samples tested. Lesion Type A refers to a moderate superficial dermal edema having mild numbers of mast cells in a perivascular orientation within the superficial dermis. Vascular endothelium exhibited mild reactive hypertrophy. Minimal numbers of neutrophils were noted in this region as well. Lesion Type C refers to lesions that were similar to those described in Lesion Type A except that the eosinophils were mild to moderate in severity, while neutrophils and mast cells were mild in severity.

On a scale of 0 to 5, lesions ranged from grade 1 to grade 4 in severity. Some of the specimens had predominantly mastocytic inflammatory perivascular infiltrates, edema, and minimal numbers of other cellular components. Other sections showed a predominance of eosinophilic inflammatory infiltrates, with lesser numbers of mast cells and neutrophils. The severity of these lesions was variable, however, in some areas, it progressed to intraepidermal eosinophilic pustulation and collagen necrobiosis within the superficial dermis.

Taken together, the tissue samples indicated the presence of superficial perivascular/periadnexal, mastocytic and eosinophilic, subacute dermatitis. Lesions noted in all the slide specimens examined are consistent with an allergic Type I hypersensitivity reaction.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:26 submitted herewith are identical.

What is claimed is:

1. An apparatus to collect ectoparasite saliva products that are substantially free of contaminating material, said apparatus comprising:
   (a) a housing operatively connected to a chamber, said chamber having an ambient temperature warmer than said housing thereby forming a temperature differential between said housing and said chamber, said housing being capable of retaining ectoparasites; and
   (b) an interface between said housing and said chamber, said interface comprising (i) a means capable of collecting at least a portion of saliva products deposited by ectoparasites retained in said apparatus and (ii) a barrier means capable of substantially preventing contaminating material from contacting said collection means, wherein said temperature differential attracts ectoparasites retained in said housing to attempt to feed through said barrier means and collection means and, thereby, deposit saliva products on said collection means.

2. The apparatus of claim 1, wherein said contaminating material comprises material selected from the group consisting of blood proteins, fecal material and larval culture medium.

3. The apparatus of claim 1, wherein said collection means comprises a membrane made of material capable of binding said products in such a manner that said products can be eluted from said membrane.

4. The apparatus of claim 1, wherein said membrane comprises a material selected from the group consisting of polyvinyl difluoride, cellulose esters, nitrocellulose, nylon, polysulfone, and polytetrafluoroethylene.

5. The apparatus of claim 1, wherein said membrane comprises a Durapore™ membrane.

6. The apparatus of claim 1, wherein said barrier means comprises a material selected from the group consisting of plastic, teflon, cloth, paper, paraffin and wax.

7. The apparatus of claim 1, wherein said barrier means comprises Parafilm™.

8. The apparatus of claim 1, wherein said apparatus further comprises a blotting means capable of maintaining a humidity suitable for survival of said ectoparasite.

9. The apparatus of claim 1, wherein said ectoparasite is a flea.

10. A method to produce a formulation comprising ectoparasite saliva products, wherein said formulation is substantially free of contaminating material, said method comprising:
   (a) collecting ectoparasite saliva products on a collection means within a saliva collection apparatus containing ectoparasites, said apparatus comprising:
      (i) a housing operatively connected to a chamber, said chamber having an ambient temperature warmer than said housing thereby forming a temperature differential between said housing and said chamber, said housing being capable of retaining ectoparasites; and
      (ii) an interface between said housing and said chamber, said interface comprising ((a)) a means capable of collecting at least a portion of saliva products deposited by ectoparasites retained in said apparatus and ((b)) a barrier means capable of substantially preventing contaminating material from contacting said collection means, wherein said temperature differential attracts ectoparasites retained in said housing to attempt to feed through said barrier means and collection means and, thereby, deposit saliva products on said collection means; and (b) extracting said products from said collection means to form said formulation.

11. The method of claim 10, wherein said method further comprises fractionating said formulation to obtain separated peak fractions and recovering at least one of said peak fractions substantially free of the remaining fractions.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 22 amino acids
      (B) TYPE: amino acid
      (D) TOPOLOGY: linear (ii) MOLECULE TYPE: protein (ix) FEATURE:
      (A) NAME/KEY: Xaa = Tyr, Gln, Ser or Arg
      (B) LOCATION: 1
      (A) NAME/KEY: Xaa = Gly or Tyr
      (B) LOCATION: 2
      (A) NAME/KEY: Xaa = Lys or Ser
      (B) LOCATION: 3
      (A) NAME/KEY: Xaa = Gly or Ser
      (B) LOCATION: 9
      (A) NAME/KEY: Xaa = Gly or Lys
      (B) LOCATION: 10
      (A) NAME/KEY: Xaa = Arg or Ile
      (B) LOCATION: 14
      (A) NAME/KEY: Xaa = Ile or Leu

```
            (B) LOCATION: 17
        (A) NAME/KEY: Xaa = Lys or Asp
            (B) LOCATION: 19
        (A) NAME/KEY: Xaa = Gly or Leu
            (B) LOCATION: 21

(xi) SEQUENCE DESCRIPTION: SEQ ID NO:1:

Xaa Xaa Xaa Gln Tyr Ser Glu Lys Xaa Xaa Arg Gly Gln Xaa His Gln
    1               5                   10                  15

Xaa Leu Xaa Lys Xaa Lys
                20

(2) INFORMATION FOR SEQ ID NO:2:

(i) SEQUENCE CHARACTERISTICS:
        (A) LENGTH: 78 amino acids
        (B) TYPE: amino acid
        (D) TOPOLOGY: linear (ii) MOLECULE TYPE: protein (ix) FEATURE:
        (A) NAME/KEY: Xaa = His or Tyr
        (B) LOCATION: 27

(xi) SEQUENCE DESCRIPTION: SEQ ID NO:2:

Asp Arg Arg Val Ser Lys Thr Cys Gln Ser Gly Gly Lys Ile Gln Ser
    1               5                   10                  15

Glu Xaa Gln Val Val Ile Lys Ser Gly Gln Xaa Ile Leu Glu Asn Tyr
                20                  25                  30

Xaa Ser Asp Gly Arg Asn Asn Asn Pro Cys His Leu Phe Cys Met
            35                  40                  45

Arg Glu Cys Arg Ser Gly Asn Gly Gly Cys Gly Asn Gly Gly Arg Thr
    50                  55                  60

Arg Pro Asp Ser Lys His Cys Tyr Cys Glu Ala Pro Tyr Ser
    65                  70                      75

(2) INFORMATION FOR SEQ ID NO:3:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:3:

Asp Ser Lys His Cys Tyr Cys Glu Ala Pro Tyr Ser
    1               5                   10

(2) INFORMATION FOR SEQ ID NO:4:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:4:

Asp Gly Arg Asn Asn Asn Pro Cys His Leu Phe Cys Met Arg Glu
    1               5                   10                  15

Cys Arg Ser Gly Asn Gly Gly Cys Gly Asn Gly Gly Arg Thr Arg Pro
                20                  25                  30

Asp Ser Lys His Cys
            35
```

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:5:

```
Asp Arg Arg Val Ser Lys Thr Cys Gln Ser Gly
 1               5                  10
```

(2) INFORMATION FOR SEQ ID NO:6:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:6:

```
Glu Asp Ile Trp Lys Val Asn Lys Lys Xaa Thr Ser Gly Gly Lys Asn
 1               5                  10                  15

Gln Asp Arg Lys Leu Asp Gln Ile Ile Gln Lys Gly Gln Gln Val Xaa
            20                  25                  30

Xaa Gln Asn Xaa Xaa Lys
            35
```

(2) INFORMATION FOR SEQ ID NO:7:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:7:

```
Asn Ser His Glu Pro Gly Asn Thr Arg Lys Ile Arg Glu Val Met Asp
 1               5                  10                  15

Lys Leu Arg Lys Gln His Pro
            20
```

(2) INFORMATION FOR SEQ ID NO:8:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:8:

```
Glu Ile Lys Arg Asn Ser His Glu Pro Gly Asn Thr Arg Lys Ile Arg
 1               5                  10                  15

Glu Val Met Asp Lys Leu Arg Lys Gln His Pro
            20                  25
```

(2) INFORMATION FOR SEQ ID NO:9:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO:9:

Asn Asp Lys Glu Pro Gly Asn Thr Arg Lys Ile Arg Glu Val Met Asp
       1               5                  10                  15

Lys Leu Arg Lys Gln Ala Gln Pro Arg Thr Asp Gly Gln Arg Pro Lys
                    20                  25                  30

Thr Xaa Ile Met
                    35

(2) INFORMATION FOR SEQ ID NO:10:

(i) SEQUENCE CHARACTERISTICS:
            (A) LENGTH: 21 amino acids
            (B) TYPE: amino acid
            (D) TOPOLOGY: linear (ii) MOLECULE TYPE: protein (xi) SEQUENCE DESCRIPTION: SEQ ID NO:10:

Xaa Leu Xaa Arg Asn Asp Lys Glu Pro Gly Asn Thr Arg Lys Ile Arg
       1               5                  10                  15

Glu Val Met Asp Lys
                    20

(2) INFORMATION FOR SEQ ID NO:11:

(i) SEQUENCE CHARACTERISTICS:
            (A) LENGTH: 12 amino acids
            (B) TYPE: amino acid
            (D) TOPOLOGY: linear (ii) MOLECULE TYPE:

(xi) SEQUENCE DESCRIPTION: SEQ ID NO:11:

Asn Asp Glu Leu Lys Phe Val Phe Val Met Ala Lys
       1               5                  10

(2) INFORMATION FOR SEQ ID NO:12:

(i) SEQUENCE CHARACTERISTICS:
            (A) LENGTH: 23 amino acids
            (B) TYPE: amino acid
            (D) TOPOLOGY: linear (ii) MOLECULE TYPE: protein (xi) SEQUENCE DESCRIPTION: SEQ ID NO:12:

Xaa Asp Glu Leu Lys Phe Val Phe Val Met Ala Lys Gly Pro Ser Xaa
       1               5                  10                  15

Gln Ala Xaa Asp Tyr Pro Cys
                    20

(2) INFORMATION FOR SEQ ID NO:13:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO:13:

Glu Leu Lys Phe Val Phe Ala Thr Ala Arg Gly Met Ser His Thr Pro
       1               5                  10                  15

```
        Cys Asp Tyr Pro
                 20

(2) INFORMATION FOR SEQ ID NO:14:

(i) SEQUENCE CHARACTERISTICS:
          (A) LENGTH: 37 amino acids
          (B) TYPE: amino acid
          (D) TOPOLOGY: linear (ii) MOLECULE TYPE: protein (ix) FEATURE:
          (A) NAME/KEY: Xaa = His or Tyr
          (B) LOCATION: 27

(xi) SEQUENCE DESCRIPTION: SEQ ID NO:14:

Asp Arg Arg Val Ser Lys Thr Xaa Gln Ser Gly Lys Ile Gln Ser
    1               5                  10                  15

Glu Xaa Gln Val Val Ile Lys Ser Gly Gln Xaa Ile Leu Glu Asn Tyr
                 20                  25                  30

Xaa Ser Asp Gly Arg
             35

(2) INFORMATION FOR SEQ ID NO:15:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (primer)

(xi) SEQUENCE DESCRIPTION: SEQ ID NO:15:

AAYAAYAAYA AYCCNTGYCA                                                        20

(2) INFORMATION FOR SEQ ID NO:16:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (primer)

(xi) SEQUENCE DESCRIPTION: SEQ ID NO:16:

CAYTCNCKCA TRCARAA                                                           17

(2) INFORMATION FOR SEQ ID NO:17:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (primer)

(xi) SEQUENCE DESCRIPTION: SEQ ID NO:17:

TGYCAYYTNT TYTGYATG                                                          18

(2) INFORMATION FOR SEQ ID NO:18:

(i) SEQUENCE CHARACTERISTICS:
          (A) LENGTH: 23 base pairs
          (B) TYPE: nucleic acid
          (C) STRANDEDNESS: single
```

(D) TOPOLOGY: linear (ii) MOLECULE TYPE: DNA (primer)

(xi) SEQUENCE DESCRIPTION: SEQ ID NO:18:

GGNGCYTCRC ARTARCARTG YTT                                        23

(2) INFORMATION FOR SEQ ID NO:19:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (primer)

(xi) SEQUENCE DESCRIPTION: SEQ ID NO:19:

GTAAAACGAC GGCCAGT                                               17

(2) INFORMATION FOR SEQ ID NO:20:

(i) SEQUENCE CHARACTERISTICS:
          (A) LENGTH: 93 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:20:

TTGTCACTTT TTTTGTATGA GAGAATGCAG GTCAGGAAAC GGCGGTTGCG GAAACGGAGG   60

AAGGACAAGA CCTGATTCGA AGCACTGCTA TGC                               93

(2) INFORMATION FOR SEQ ID NO:21:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (primer)

(xi) SEQUENCE DESCRIPTION: SEQ ID NO:21:

GARGAYATHT GGAARGTNAA YAA                                        23

(2) INFORMATION FOR SEQ ID NO:22:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (primer)

(xi) SEQUENCE DESCRIPTION: SEQ ID NO:22:

ACNTCNGGNG GNAARAAYCA RGA                                        23

(2) INFORMATION FOR SEQ ID NO:23:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (primer)

(xi) SEQUENCE DESCRIPTION: SEQ ID NO:23:

| TTGGGTACCG GGCCCCCCCT | 20 |

(2) INFORMATION FOR SEQ ID NO:24:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

| CTTACGTCCG GGGGTAAGAA TCAGGATAGA AAACTCGATC AAATAATTCA AAAAGGCCAA | 60 |
| CAAGTTAAAA TCCAAAATAT TTGCAAATTA ATACGAGATA AACCACATAC AAATCAAGAG | 120 |
| AAAGAAAAAT GTATGAAATT TGCACAAAA AACGTTTGCA AAGGTTATAG AGGAGCTTGT | 180 |
| GATGGCAATA TTTGCTACTG CAGCAGGCCA AGTAATTTAG GTCCTGATTG GAAAGTCAAC | 240 |
| GAAAGAATCG AAAGACTCCC AATAACAAAG ATTCTCGTCT CAGGAAATAG TTCCATATCG | 300 |
| ACAACAATTA CGAATTCCAA ATATTTCGAA ACTAAAAATT CAGAGACCAA TGAAGATTCC | 360 |
| AAATCGAAAA AACATTCGAA AGAAAAATGT CGTGGTGGAA ATGATGCTGG ATGTGATGGA | 420 |
| AACGTTTTGT TATTGTCGAC CAAAAAATAA ATAATAATTA TAATAAATAA ATTGTTATAG | 480 |
| TTATTAGTTA TCCCGTCACA TATTAGAAAA GTGGCTTATA ATTTATGAAC AATATAACAC | 540 |
| ATAAATTAGT TGTGTAAAAA AAAAAAAAAA AAA | 573 |

(2) INFORMATION FOR SEQ ID NO:25:

(i) SEQUENCE CHARACTERISTICS:
        (A) LENGTH: 149 amino acids
        (B) TYPE: amino acid
        (D) TOPOLOGY: linear (ii) MOLECULE TYPE: protein (xi) SEQUENCE DESCRIPTION: SEQ ID NO:25:

```
Leu Thr Ser Gly Gly Lys Asn Gln Asp Arg Lys Leu Asp Gln Ile Ile
 1               5                  10                  15

Gln Lys Gly Gln Gln Val Lys Ile Gln Asn Ile Cys Lys Leu Ile Arg
            20                  25                  30

Asp Lys Pro His Thr Asn Gln Glu Lys Glu Lys Cys Met Lys Phe Cys
        35                  40                  45

Thr Lys Asn Val Cys Lys Gly Tyr Arg Gly Ala Cys Asp Gly Asn Ile
    50                  55                  60

Cys Tyr Cys Ser Arg Pro Ser Asn Leu Gly Pro Asp Trp Lys Val Asn
65                  70                  75                  80

Glu Arg Ile Glu Arg Leu Pro Ile Thr Lys Ile Leu Val Ser Gly Asn
                85                  90                  95

Ser Ser Ile Ser Thr Thr Ile Thr Asn Ser Lys Tyr Phe Glu Thr Lys
            100                 105                 110

Asn Ser Glu Thr Asn Glu Asp Ser Lys Ser Lys Lys His Ser Lys Glu
        115                 120                 125

Lys Cys Arg Gly Gly Asn Asp Arg Gly Cys Asp Gly Asn Val Leu Leu
    130                 135                 140

Leu Ser Thr Lys Lys
145
```

(2) INFORMATION FOR SEQ ID NO:26:

(i) SEQUENCE CHARACTERISTICS:
      (A) LENGTH: 158 amino acids
      (B) TYPE: amino acid
      (D) TOPOLOGY: linear (ii) MOLECULE TYPE: protein (xi) SEQUENCE DESCRIPTION: SEQ ID NO:26:

```
Glu Asp Ile Trp Lys Val Asn Lys Lys Leu Thr Ser Gly Gly Lys Asn
1               5                   10                  15

Gln Asp Arg Lys Leu Asp Gln Ile Ile Gln Lys Gly Gln Gln Val Lys
            20                  25                  30

Ile Gln Asn Ile Cys Lys Leu Ile Arg Asp Lys Pro His Thr Asn Gln
            35                  40                  45

Glu Lys Glu Lys Cys Met Lys Phe Cys Thr Lys Asn Val Cys Lys Gly
        50                  55                  60

Tyr Arg Gly Ala Cys Asp Gly Asn Ile Cys Tyr Cys Ser Arg Pro Ser
65                  70                  75                  80

Asn Leu Gly Pro Asp Trp Lys Val Asn Glu Arg Ile Glu Arg Leu Pro
                85                  90                  95

Ile Thr Lys Ile Leu Val Ser Gly Asn Ser Ser Ile Ser Thr Thr Ile
                100                 105                 110

Thr Asn Ser Lys Tyr Phe Glu Thr Lys Asn Ser Glu Thr Asn Glu Asp
            115                 120                 125

Ser Lys Ser Lys Lys His Ser Lys Glu Lys Cys Arg Gly Gly Asn Asp
    130                 135                 140

Arg Gly Cys Asp Gly Asn Val Leu Leu Leu Ser Thr Lys Lys
145                 150                 155
```